United States Patent [19]

Cywin et al.

[11] Patent Number: 5,705,499

[45] Date of Patent: Jan. 6, 1998

[54] 8-ARYLALKYL- AND 8-ARYLHETEROALKYL-5,11-DIHYDRO-6H-DIPYRIDO[3,2-B:2',3'-E][1,4]DIAZEPINES AND THEIR USE IN THE TREATMENT OF HIV-1 INFECTION

[75] Inventors: Charles L. Cywin, Bethel, Conn.; MaryAnn Hoermann, Holmes, N.Y.; Janice M. Klunder, Needham, Mass.

[73] Assignee: Boehringer Ingelheim Pharmaceuticals, Inc., Ridgefield, Conn.

[21] Appl. No.: 710,996

[22] Filed: Sep. 25, 1996

[51] Int. Cl.$^6$ .................. A61K 31/55; C07D 471/14
[52] U.S. Cl. .................. 514/220; 514/495; 514/557
[58] Field of Search .................. 540/495, 557; 514/220

[56] References Cited

U.S. PATENT DOCUMENTS 5,366,972  11/1994  Hargrave .

FOREIGN PATENT DOCUMENTS

WO 95/22545  8/1995  WIPO .

OTHER PUBLICATIONS

Hargrave, K. et al; "Novel Non–Nucleoside Inhibitors of HIV–1 Reverse Transcriptase. 1. Tricyclic Pyridobenzo–Dipyridodiazepinones" Journal of Medicinal Chemistry vol. 34 No. 7, 1991 pp. 2231–2241 XP002020340.

*Primary Examiner*—Robert T. Bond
*Attorney, Agent, or Firm*—Robert P. Raymond; Alan R. Stempel; Wendy E. Rieder

[57] ABSTRACT

Disclosed are novel 8-arylalkyl-5,11-dihydro-6H-dipyrido [3,2-b:2',3'-e][1,4]diazepines. These are useful in the treatment of HIV-1 infection.

10 Claims, No Drawings

8-ARYLALKYL- AND 8-ARYLHETEROALKYL-5,11-DIHYDRO-6H-DIPYRIDO[3,2-B:2',3'-E][1,4]DIAZEPINES AND THEIR USE IN THE TREATMENT OF HIV-1 INFECTION

RELATED APPLICATIONS

The benefit of provisional application Ser. No. 60/004,806, filed Oct. 6, 1995, and Ser. No. 60/008,695, filed Dec. 15, 1995, is hereby claimed.

FIELD OF THE INVENTION

The invention relates to novel 8-arylalkyl-5,11-dihydro-6H-dipyrido[3,2-b:2',3'-e][1,4]diazepines and pharmaceutically acceptable salts thereof, methods for preparing these compounds, the use of these compounds either alone or in combination with other anti-virals, immunomodulators, antibiotics, anti-infectives, or vaccines in the treatment of HIV infection, and to pharmaceutical compositions containing these compounds.

BACKGROUND OF THE INVENTION

The human disease, acquired immunodeficiency syndrome (AIDS), is caused by the human immunodeficiency virus (HIV), particularly the strain known as HIV-1.

Like other viruses, HIV-1 cannot replicate without commandeering the biosynthetic apparatus of the host cell it infects. It causes this apparatus to produce the structural proteins that make up the viral progeny. These proteins are encoded by the genetic material contained within the infecting virus particle, or virion. Being a retrovirus, however, the genetic material of HIV is RNA, and not DNA as in the host cell's genome. Accordingly, the viral RNA must first be converted into DNA, and then integrated into the host cell's genome, in order for the host cell to produce the required viral proteins. The conversion of the RNA to DNA is accomplished through the use of the enzyme reverse transcriptase (RT), which is included within the infecting virion along with the RNA. Reverse transcriptase has three known enzymatic functions; it acts as an RNA-dependent DNA polymerase, as a ribonuclease, and as a DNA-dependent DNA polymerase. Acting first as an RNA-dependent DNA polymerase, RT makes a single-stranded DNA copy of the viral RNA. Acting as a ribonuclease, RT frees the DNA just produced from the original viral RNA and destroys the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds that inhibit the enzymatic functions of HIV-1 reverse transcriptase will inhibit replication of HIV-1 in infected cells. Such compounds are useful in the prevention or treatment of HIV-1 infection in human subjects, as demonstrated by the known RT inhibitors 3'-azido-3'-deoxythymidine (AZT), 2',3'-dideoxyinosine (ddI), and 2',3'-dideoxycytidine (ddC), the only drugs thus far approved for use in the treatment of AIDS and AIDS-related complex (ARC).

As with any antiviral therapy, use of RT inhibitors in the treatment of AIDS eventually leads to virus that is less sensitive to the given drug. Resistance (reduced sensitivity) to these drugs is the result of mutations that occur in the reverse transcriptase segment of the pol gene. The compounds of the present invention are not only highly potent inhibitors of the wild-type (non-mutated) viral RT enzyme, but are also effective against the reverse transcriptase of many of the mutant viruses that have been observed in patients who have been treated with RT inhibitors.

Specifically, the compounds of the present invention are effective in inhibiting the Y181C mutant [in which the tyrosine (Y) at codon 181 has been mutated to a cysteine (C) residue], which has been the most commonly observed mutant in clinical studies following therapy with many non-nucleoside reverse transcriptase inhibitors. The compounds are also effective against other observed mutant enzymes that contain a single point mutation, such as K103N, V106A, G190A, Y188C, or P236L.

Compounds having related tricyclic structures which are inhibitors of HIV-1 are described in U.S. Pat. No. 5,366,972. Other inhibitors of HIV-1 reverse transcriptase are described in Hargrave et al., *J. Med Chem.*, 34, 2231 (1991).

SUMMARY OF THE INVENTION

A first aspect of the invention comprises novel 8-arylalkyl- and 8-arylheteroalkyldipyridodiazepines. These possess inhibitory activity against both wild-type and mutant HIV-1 RT. A second aspect of the invention comprises methods for making these novel compounds. A third aspect of the invention is a method for treating HIV-1 infection which comprises administering, to a human being infected by HIV-1, a therapeutically effective amount of one of the above-mentioned novel compounds, either alone or in combination with other antiviral agents. A final aspect of the invention comprises pharmaceutical compositions suitable for the treatment of HIV-1 infection comprising the above-mentioned compounds.

DESCRIPTION OF THE INVENTION

In one of its composition of matter aspects, the invention comprises 8-arylalkyl- and 8-arylheteroalkyl-5,11-dihydro-6H-dipyrido[3,2-b:2',3'-e][1,4]diazepines of the formula 1,

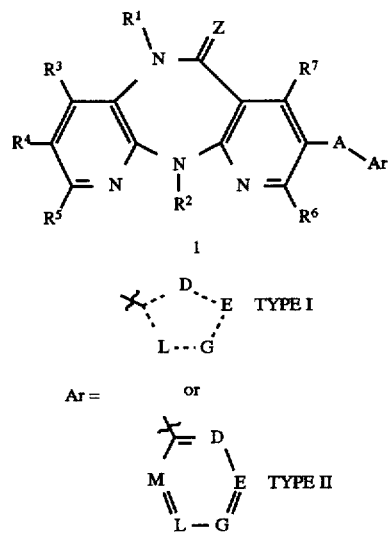

wherein,

A is a connecting chain of 1 to 3 atoms, wherein one of the atoms is oxygen, phosphorous or sulfur (optionally oxidized or unoxidized), or nitrogen (unsubstituted or substituted with methyl or acetyl), and the remaining atoms are carbon; or, all of the atoms are carbon atoms, wherein two of the atoms form an unsaturated alkynyl or cis- or trans-alkenyl bond, or all of the atoms are connected by single bonds and one of the atoms is optionally unsubstituted or substituted with oxo, methyl, hydroxy, amino, or halogen wherein halogen is defined as fluoro, chloro, bromo or iodo; or, A is a connecting chain of 2 atoms, wherein one of the atoms is nitrogen (unsubstituted or substituted with methyl) or oxygen, and the adjacent position is carbonyl; or, A is a 1,2-disubstituted cyclopropyl or oxiranyl ring;

D, E, G, and L form a five-membered heteroaromatic ring of type I, wherein the dotted bonds represent either double or single bonds depending on the valency of the atoms, either D or E is nitrogen (unsubstituted or substituted with methyl, ethyl, or acetyl), oxygen, or sulfur, and the three remaining positions are carbon, wherein one or two of these carbon atoms are optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, one of D, E, G, and L is nitrogen, one is oxygen or sulfur, and the two remaining positions are carbon optionally unsubstituted or substituted with alkyl, alkyloxy, or alkylmercapto of 1 to 4 carbon atoms, trifluoromethyl, hydroxymethyl, hydroxyethyl, halogen, acetyl, methoxy or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, two of D, E, G, and L are nitrogen (wherein one of the nitrogen atoms is unsubstituted or substituted with methyl, ethyl, acetyl, mono- or dimethylaminosulfonyl, methoxy- or ethoxycarbonyl, aminocarbonyl, alkylaminocarbonyl, or phenylaminocarbonyl), and the two remaining positions are carbon optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, two of D, E, G, and L are nitrogen, one is oxygen or sulfur, and the remaining position is carbon optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, three of D, E, G, and L are nitrogen (wherein one of the nitrogen atoms is unsubstituted or substituted with methyl, ethyl, acetyl, mono- or dimethylaminosulfonyl, methoxy- or ethoxycarbonyl, aminocarbonyl, alkylaminocarbonyl, or phenylaminocarbonyl), and the remaining position is carbon optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, D, E, G, and L are nitrogen, wherein one of the nitrogen atoms is unsubstituted or substituted with methyl, ethyl, acetyl, mono- or dimethylaminosulfonyl, methoxy- or ethoxycarbonyl, aminocarbonyl, alkylaminocarbonyl, or phenylaminocarbonyl; or, D is nitrogen (wherein the nitrogen atom is unsubstituted or substituted with methyl, ethyl, acetyl, mono- or dimethylaminosulfonyl, methoxy- or ethoxycarbonyl, aminocarbonyl, alkylaminocarbonyl, or phenylaminocarbonyl), oxygen, or sulfur, L is carbon (optionally unsubstituted or substituted with methyl or ethyl) or nitrogen, and E and G together form one side of a fused phenyl or pyridyl ring (which is either unsubstituted or substituted by alkyl, alkyloxy, or alkylmercapto of 1 to 4 carbon atoms, amino, hydroxy, carboxy, or aminocarbonyl); or, D is carbon (optionally unsubstituted or substituted with methyl or ethyl) or nitrogen, E is nitrogen (wherein the nitrogen atom is unsubstituted or substituted with methyl, ethyl, acetyl, mono- or dimethylaminosulfonyl, methoxy- or ethoxycarbonyl, aminocarbonyl, alkylaminocarbonyl, or phenylaminocarbonyl), oxygen, or sulfur, G and L together form one side of a fused phenyl or pyridyl ring (which is either unsubstituted or substituted by alkyl, alkyloxy, or alkylmercapto of 1 to 4 carbon atoms, amino, hydroxy, carboxy, or aminocarbonyl); or, D, E, G, L and M form a six-membered aromatic ring of type II, wherein D, E, G, L, and M are carbon, of which one or two of these carbon atoms are optionally unsubstituted or substituted with methyl, ethyl, trifluoromethyl, hydroxymethyl, hydroxyethyl, halogen, acetyl, acetyloxy, methoxy- or ethoxycarbonyl, carboxy, hydroxy, amino, methyl- or ethylamino, acetamido, ureido, methylsulfonamido, alkyloxy of 1 to 4 carbon atoms, methyl- or ethylmercapto, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, D, E, G, L and M are carbon, wherein D and E form one side of a fused phenyl, pyridyl, pyrrolyl, thienyl, or furanyl ring (which is either unsubstituted or substituted by alkyl, alkyloxy, or alkylmercapto of 1 to 4 carbon atoms, amino, hydroxy, carboxy, or aminocarbonyl) and one of G, L, or M is optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, D, E, G, L and M are carbon, wherein E and G form one side of a fused phenyl, pyridyl, pyrrolyl, thienyl, or furanyl ring (which is either unsubstituted or substituted by alkyl, alkyloxy, or alkylmercapto of 1 to 4 carbon atoms, amino, hydroxy, carboxy, or aminocarbonyl) and one of D, L, or M is optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, D, E, G, L and M form a six-membered heteroaromatic ring of type II, wherein one of D, E, or G is nitrogen (optionally unoxidized or oxidized to the corresponding N-oxide), and the four remaining positions are carbon, of which one of these carbon atoms is optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro, and of which a second of these carbon atoms is optionally unsubstituted or substituted with methyl, ethyl, hydroxy, or amino; or, one of D, E, or G is nitrogen, L and M form one side of a fused phenyl, pyridyl, pyrrolyl, thienyl, or furanyl ring (which is either unsubstituted or substituted by alkyl, alkyloxy, or alkylmercapto of 1 to 4 carbon atoms, amino, hydroxy, carboxy, or aminocarbonyl), and the remaining two positions are carbon, of which one of these carbon atoms is optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, one of D, E or M is nitrogen, G and L form one side of a fused phenyl, pyridyl, pyrrolyl, thienyl, or furanyl ring (which is either unsubstituted or substituted by alkyl, alkyloxy, or alkylmercapto of 1 to 4 carbon atoms, amino, hydroxy, carboxy, or aminocarbonyl), and the remaining two positions are carbon, of which one of these carbon atoms is optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, D is nitrogen, E and G form one side of a fused phenyl, pyridyl, pyrrolyl, thienyl, or furanyl ring (which is either unsubstituted or substituted by alkyl, alkyloxy, or alkylmercapto of 1 to 4 carbon atoms, amino, hydroxy, carboxy, or aminocarbonyl), and the remaining two positions are carbon, of which one of these carbon atoms is optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, two of D, E, G, L, and M are nitrogen, and the three remaining positions are carbon, of which one of these carbon atoms is optionally unsubstituted or substituted with methyl, ethyl, trifluoromethyl, hydroxy, acetoxy, hydroxymethyl, hydroxyethyl, halogen, acetyl, methoxy- or ethoxycarbonyl, carboxy, hydroxy, amino, methyl- or ethylamino, acetamido, ureido, methylsulfonamido, alkyloxy of 1 to 4 carbon atoms, methyl- or ethylmercapto, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro, and of which a second of these carbon atoms is optionally unsubstituted or substituted with methyl, ethyl, hydroxy, or amino; or, two of D, E, and G are nitrogen, and L and M together form one side of a fused phenyl, pyridyl, imidazolyl, pyrazolyl, or triazolyl ring (the carbon atoms of which are either unsubstituted or substituted by alkyl, alkyloxy, or alkylmercapto of 1 to 4 carbon atoms, amino, hydroxy, carboxy, or aminocarbonyl); or, two of D, L, and M are nitrogen, and E and G together form one side of a fused phenyl, pyridyl, imidazolyl, pyrazolyl, or triazolyl ring (the carbon atoms of which are either unsubstituted or substituted by alkyl, alkyloxy, or alkylmercapto of 1 to 4 carbon atoms, amino, hydroxy, carboxy, or aminocarbonyl);

$R^1$ is hydrogen, alkyl of 1 to 6 carbon atoms, fluoroalkyl of 1 to 6 carbon atoms and 1 to 3 fluorine atoms, alkenylmethyl or alkynylmethyl of 3 to 6 carbon atoms, aryl or arylmethyl (wherein the aryl moiety is phenyl, thienyl or furanyl, which is either unsubstituted or substituted by methyl, methoxy or halogen), alkanoyl or thioalkanoyl of 2 to 4 carbon atoms, alkylsulfonyl of 1 to 4 carbon atoms, mono- or dimethylaminosulfonyl, aminosulfonyl, aminocarbonyl, mono- or di-alkylaminocarbonyl wherein each alkyl moiety contains 1 to 2 carbon atoms, aminoethyl, mono- or di-alkylaminoethyl wherein each alkyl moiety contains 1 to 2 carbon atoms, alkyloxyalkyl or alkylthioalkyl of 2 to 4 carbon atoms, alkyloxycarbonyl wherein the alkyl moiety contains 1 to 4 carbon atoms, alkenyloxycarbonyl wherein the alkenyl moiety contains 2 to 4 carbon atoms, hydroxy, alkyloxy of 1 to 4 carbon atoms, cyano, amino, mono- or di-alkylamino wherein each alkyl moiety contains 1 to 4 carbon atoms, aminocarbonylmethyl, mono- or di-alkylaminocarbonylmethyl wherein the alkyl moiety contains 1 to 2 carbon atoms;

Z is oxygen, sulfur, =NCN or a group of the formula =$NOR^8$ wherein $R^8$ is alkyl of 1 to 3 carbon atoms;

$R^2$ is hydrogen, alkyl of 1 to 6 carbon atoms, fluoroalkyl of 1 to 6 carbon atoms and 1 to 3 fluorine atoms, cycloalkyl of 3 to 6 carbon atoms, oxetanyl, thietanyl, tetrahydrofuranyl, tetrahydrothienyl, tetrahydropyranyl, tetrahydrothiopyranyl, alkenylmethyl or alkynylmethyl of 3 to 6 carbon atoms, alkyloxyalkyl or alkylthioalkyl of 2 to 5 carbon atoms, alkanoyl or thioalkanoyl of 2 to 5 carbon atoms, cyano, cyanoalkyl of 2 to 5 carbon atoms, hydroxyalkyl or acyloxyalkyl wherein the alkyl moiety contains 2 to 6 carbon atoms and the acyl moiety contains 2 to 3 carbon atoms, oxazolyl, isoxazolyl, thiazolyl, aryl or arylmethyl (wherein the aryl moiety is phenyl, thienyl or furanyl, which is either unsubstituted or substituted by alkyl or alkyloxy of 1 to 3 carbon atoms, hydroxy or halogen), or alkyloxycarbonylmethyl wherein the alkyl moiety contains 1 to 5 carbon atoms;

$R^3$ is alkyl of 1 to 6 carbon atoms, alkenyl or alkynyl of 2 to 6 carbon atoms, trihalomethyl, hydroxyalkyl of 1 to 6 carbon atoms, alkyloxyalkyl or alkylthioalkyl of 2 to 6 carbon atoms, or halogen;

$R^4$ is hydrogen, methyl, or halogen, and $R^5$ is hydrogen; or, $R^3$ and $R^5$ are each hydrogen and $R^4$ is methyl or halogen; or $R^3$ and $R^4$ are each hydrogen and $R^5$ is alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxyalkyl or alkylthioalkyl of 2 to 6 carbon atoms, aryloxy(or thio)methyl (wherein the aryl moiety is phenyl, thienyl or furanyl, which is either unsubstituted or substituted by alkyl or alkyloxy of 1 to 3 carbon atoms, hydroxy or halogen), arylmethyloxy(or thio) methyl or arylethyloxy(or thio)methyl (wherein the aryl moiety is phenyl, thienyl or furanyl, which is either unsubstituted or substituted by alkyl or alkyloxy of 1 to 3 carbon atoms, hydroxy or halogen), alkyloxycarbonylalkyl wherein the alkyl moieties each contain 1 to 2 carbon atoms, carboxyalkyl or cyanoalkyl wherein the alkyl moieties each contain 1 to 5 carbon atoms, mono- or di-alkylaminocarbonylalkyl wherein the alkyl moieties each contain 1 to 2 carbon atoms, hydroxy, mercapto, alkyloxy or alkylthio of 1 to 5 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkyloxycarbonyl wherein the alkyl moiety contains 1 to 3 carbon atoms, mono- or dialkylaminocarbonyl wherein each alkyl moiety contains 1 to 3 carbon atoms, aminoalkyl of 1 to 4 carbon atoms, mono- or di-alkylamino wherein each alkyl moiety contains 1 to 3 carbon atoms mono- or di-alkylaminoalkyl wherein each alkyl moiety contains 1 to 3 carbon atoms, N-pyrrolidino, N-piperidino, N-morpholino, aryl or arylalkyl (wherein the aryl moiety is phenyl, pyridyl, or a 5-membered heteroaromatic ring which is either unsubstituted or substituted by alkyl or alkyloxy of 1 to 3 carbon atoms, hydroxy, amino, or halogen, and the alkyl moiety contains 1 to 3 carbon atoms which may be unsubstituted or substituted with a methyl, hydroxy, or amino groups), halogen, cyano, nitro, azido or carboxy; or, $R^5$ is hydrogen and $R^3$ and $R^4$ are joined to form a cycloalkyl with a 3 or 4 carbon bridge; or, $R^3$ is hydrogen and $R^4$ and $R^5$ are joined to form a cycloalkyl with a 3 or 4 carbon bridge; or, $R^3$, $R^4$, and $R^5$ are each hydrogen;

$R^6$ and $R^7$ are each hydrogen.

A subgeneric aspect of the invention comprises compounds of formula 1, wherein,

A is a connecting chain of 1 to 3 atoms, wherein one of the atoms is oxygen, nitrogen (unsubstituted or substituted with methyl or acetyl), or sulfur (optionally oxidized or unoxidized), and the remaining atoms are carbon; or, all of the atoms are carbon atoms, wherein two of the atoms form a cis-alkenyl bond or all of the atoms are connected by single bonds and one of the atoms is optionally unsubstituted or substituted with oxo, methyl, hydroxy, halogen, or amino; or, A is an amide, wherein the nitrogen atom (unsubstituted or substituted with methyl) is attached to the tricyclic skeleton and the carbonyl is attached to the 5- or 6-membered aromatic ring; or, A is a cis-1,2-disubstituted cyclopropyl or oxiranyl ring;

D, E, G, and L form a five-membered heteroaromatic ring of type I, wherein the dotted bonds represent either double or single bonds depending on the valency of the atoms, either D or E is nitrogen (unsubstituted or substituted with methyl, ethyl, or acetyl), and the three remaining positions are carbon, wherein one or two of these carbon atoms are optionally unsubstituted or substituted with alkyl, alkyloxy, or alkylmercapto of 1 to 3 carbon atoms, amino, hydroxy, carboxy, or aminocarbonyl; or, one of D, E, G, and L is nitrogen, one is oxygen or sulfur, and the two remaining positions are carbon, wherein one of the carbon atoms is optionally unsubstituted or substituted with alkyl, alkyloxy, or alkylmercapto of 1 to 3 carbon atoms, amino, hydroxy, carboxy, or aminocarbonyl; or, two of D, E, G, and L are nitrogen (wherein one of the nitrogen atoms is unsubstituted or substituted with methyl, ethyl, or acetyl), and the two remaining positions are carbon, wherein one of the carbon atoms is optionally unsubstituted or substituted with alkyl, alkyloxy, or alkylmercapto of 1 to 3 carbon atoms, amino, hydroxy, carboxy, or aminocarbonyl; or, two of D, E, G, and L are nitrogen, one is oxygen or sulfur, and the remaining position is carbon, optionally unsubstituted or substituted with alkyl, alkyloxy, or alkylmercapto of 1 to 3 carbon atoms, amino, hydroxy, carboxy, or aminocarbonyl; or, three of D, E, G, and L are nitrogen (wherein one of the nitrogen atoms is unsubstituted or substituted with methyl, ethyl, or acetyl), and the remaining position is carbon, optionally unsubstituted or substituted with alkyl, alkyloxy, or alkylmercapto of 1 to 3 carbon atoms, amino, hydroxy, carboxy, or aminocarbonyl; or, D, E, G, and L are nitrogen, wherein one of the nitrogen atoms is unsubstituted or substituted with methyl, ethyl, acetyl; or, D is nitrogen (wherein the nitrogen atom is unsubstituted or substituted with methyl, ethyl, or acetyl), oxygen, or sulfur, L is carbon or nitrogen, and E and G together form one side of a fused phenyl or pyridyl ring (which is optionally unsubstituted or substituted with alkyl, alkyloxy, or alkylmercapto of 1 to 3 carbon atoms, amino, hydroxy, carboxy, or aminocarbonyl; or, D is carbon or nitrogen, E is nitrogen (wherein the nitrogen atom is unsubstituted or substituted with methyl, ethyl, or acetyl), oxygen, or sulfur, G and L together form one side of a fused phenyl or pyridyl ring (which is optionally unsubstituted or substituted with alkyl, alkyloxy, or alkylmercapto of 1 to 3 carbon atoms, amino, hydroxy, carboxy, or aminocarbonyl; or, D, E, G, L and M form a six-membered aromatic ring of type II, wherein D, E, G, L, and M are carbon, of which one of these carbon atoms is optionally unsubstituted or substituted with methyl, ethyl, amino, methyl- or ethylamino, acetamido, acetyl, acetyloxy, hydroxy, halogen, trifluoromethyl, hydroxymethyl, methoxy, ethoxy, methyl- or ethylmercapto, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, or cyano, and of which a second of these carbon atoms is optionally unsubstituted or substituted with methyl or ethyl; or, D, E, G, L and M are carbon, wherein D and E form one side of a fused phenyl, pyridyl, pyrrolyl, thienyl, or furanyl ring (which is either unsubstituted or substituted by alkyl, alkyloxy, or alkylmercapto of 1 to 3 carbon atoms, amino, hydroxy, carboxy, or aminocarbonyl) and one of G, L, or M is optionally unsubstituted or substituted with alkyl, alkyloxy, or alkylmercapto of 1 to 3 carbon atoms, amino, methyl- or ethylamino, hydroxy, halogen, trifluoromethyl, hydroxymethyl, methoxy- or ethoxycarbonyl, or aminocarbonyl; or, D, E, G, L and M are carbon, wherein E and G form one side of a fused phenyl, pyridyl, pyrrolyl, thienyl, or furanyl ring (which is either unsubstituted or substituted by alkyl, alkyloxy, or alkylmercapto of 1 to 3 carbon atoms, amino, hydroxy, carboxy, or aminocarbonyl) and one of D, L, or M is optionally unsubstituted or substituted with alkyl, alkyloxy, or alkylmercapto of 1 to 3 carbon atoms, amino, methyl- or ethylamino, hydroxy, halogen, trifluoromethyl, hydroxymethyl, methoxy- or ethoxycarbonyl, or aminocarbonyl; or, D, E, G, L and M form a six-membered heteroaromatic ring of type II, wherein one of D, E, or G is nitrogen (optionally unoxidized or oxidized to the corresponding N-oxide), and the four remaining positions are carbon, of which one of these carbon atoms is optionally unsubstituted or substituted with methyl, ethyl, amino, methyl- or ethylamino, acetamido, acetyl, acetyloxy, hydroxy, halogen, trifluoromethyl, hydroxymethyl, methoxy, ethoxy, methyl- or ethylthio, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, or cyano, and of which a second of these carbon atoms is optionally unsubstituted or substituted with methyl or ethyl; or, one of D, E, or G is nitrogen, L and M form one side of a fused phenyl, pyridyl, pyrrolyl, thienyl, or furanyl ring (which is either unsubstituted or substituted by alkyl, alkyloxy, or alkylmercapto of 1 to 3 carbon atoms, amino, hydroxy, carboxy, or aminocarbonyl), and the remaining two positions are carbon, of which one of these carbon atoms is optionally unsubstituted or substituted with alkyl, alkyloxy, or alkylmercapto of 1 to 3 carbon atoms, amino, methyl- or ethylamino, hydroxy, halogen, trifluoromethyl, hydroxymethyl, methoxy- or ethoxycarbonyl, or aminocarbonyl; or, one of D, E or M is nitrogen, G and L form one side of a fused phenyl, pyridyl, pyrrolyl, thienyl, or furanyl ring (which is either unsubstituted or substituted by alkyl, alkyloxy, or alkylmercapto of 1 to 3 carbon atoms, amino, hydroxy, carboxy, or aminocarbonyl), and the remaining two positions are carbon, of which one of these carbon atoms is optionally unsubstituted or substituted with alkyl, alkyloxy, or alkylmercapto of 1 to 3 carbon atoms, amino, methyl- or ethylamino, hydroxy, halogen, trifluoromethyl, hydroxymethyl, methoxy- or ethoxycarbonyl, or aminocarbonyl; or, D is nitrogen, E and G form one side of a fused phenyl, pyridyl, pyrrolyl, thienyl, or furanyl ring (which is either unsubstituted or substituted by alkyl, alkyloxy, or alkylmercapto of 1 to 3 carbon atoms, amino, hydroxy, carboxy, or aminocarbonyl), and the remaining two positions are carbon, of which one of these carbon atoms is optionally unsubstituted or substituted with alkyl, alkyloxy, or alkylmercapto of 1 to 3 carbon atoms, amino, methyl- or ethylamino, hydroxy, halogen, trifluoromethyl, hydroxymethyl, methoxy- or ethoxycarbonyl, or aminocarbonyl; or, two of D, E, G, L, and M are nitrogen, and the three remaining positions are carbon, of which one of these carbon atoms is optionally unsubstituted or substituted with methyl, ethyl, amino, methyl- or ethylamino, acetamido, acetyl, acetyloxy, hydroxy, halogen, trifluoromethyl, hydroxymethyl, methoxy, ethoxy, methyl- or ethylthio, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, or cyano, and of which a second of these carbon atoms is optionally unsubstituted or substituted with methyl or ethyl; or, two of D, E, and G are nitrogen, and L and M together form one side of a fused phenyl, pyridyl, imidazolyl, pyrazolyl, or triazolyl ring (the carbon atoms of which are either unsubstituted or substituted by alkyl, alkyloxy, or alkylmercapto of 1 to 3 carbon atoms, amino, hydroxy, carboxy, or aminocarbonyl); or, two of D, L, and M are nitrogen, and E and G together form one side of a fused phenyl, pyridyl, imidazolyl, pyrazolyl, or triazolyl ring (the carbon atoms of which are either unsubstituted or substituted by alkyl, alkyloxy, or alkylmercapto of 1 to 3 carbon atoms, amino, hydroxy, carboxy, or aminocarbonyl);

$R^1$ is hydrogen, alkyl of 1 to 4 carbon atoms, fluoroalkyl of 1 to 4 carbon atoms and 1 to 3 fluorine atoms, cyclopropyl, alkenylmethyl or alkynylmethyl of 3 to 4 carbon atoms, 2-halo-2-propen-1-yl, alkanoyl of 2 to 3 carbon atoms, alkyloxyalkyl or alkylthioalkyl of 2 to 3 carbon atoms, or cyanoalkyl wherein the alkyl moiety contains 1 to 3 carbon atoms;

Z is oxygen, sulfur or a group of the formula $=NOR^9$ wherein $R^9$ is methyl or ethyl;

$R^2$ is hydrogen, alkyl of 1 to 5 carbon atoms, fluoroalkyl of 1 to 5 carbon atoms, cycloalkyl of 3 to 5 carbon atoms, oxetanyl, thietanyl, alkenylmethyl or alkynylmethyl of 3 to 5 carbon atoms, alkyloxyalkyl or alkylthioalkyl of 2 to 4 carbon atoms, alkanoyl of 2 to 4 carbon atoms, hydroxyalkyl of 2 to 5 carbon atoms, aryl or arylmethyl (wherein the aryl moiety is phenyl, thienyl or furanyl, which is either unsubstituted or substituted by alkyl or alkyloxy of 1 to 3 carbon atoms, hydroxy or halogen), or alkyloxycarbonylmethyl wherein the alkyl moiety contains 1 to 4 carbon atoms;

$R^3$ is alkyl of 1 to 6 carbon atoms, alkenyl or alkynyl of 2 to 6 carbon atoms, trihalomethyl, hydroxyalkyl of 1 to 6 carbon atoms, alkyloxyalkyl or alkylthioalkyl of 2 to 6 carbon atoms, or halogen;

$R^4$ is hydrogen, methyl, or halogen, and $R^5$ is hydrogen; or, $R^3$ and $R^5$ are each hydrogen and $R^4$ is methyl or halogen; or $R^3$ and $R^4$ are each hydrogen and $R^5$ is alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxyalkyl or alkylthioalkyl of 2 to 6 carbon atoms, aryloxy(or thio)methyl (wherein the aryl moiety is phenyl, thienyl or furanyl, which is either unsubstituted or substituted by alkyl or alkyloxy of 1 to 3 carbon atoms, hydroxy or halogen), arylmethyloxy(or thio)methyl or arylethyloxy(or thio)methyl (wherein the aryl moiety is phenyl, thienyl or furanyl, which is either unsubstituted or substituted by alkyl or alkyloxy of 1 to 3 carbon atoms, hydroxy or halogen), alkyloxycarbonylalkyl wherein the alkyl moieties each contain 1 to 2 carbon atoms, carboxyalkyl or cyanoalkyl wherein the alkyl moieties each contain 1 to 5 carbon atoms, mono- or di-alkylaminocarbonylalkyl wherein the alkyl moieties each contain 1 to 2 carbon atoms, hydroxy, mercapto, alkyloxy or alkylthio of 1 to 5 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkyloxycarbonyl wherein the alkyl moiety contains 1 to 3 carbon atoms, mono- or di-alkylaminocarbonyl wherein each alkyl moiety contains 1 to 3 carbon atoms, aminoalkyl of 1 to 4 carbon atoms, mono- or di-alkylamino wherein each alkyl moiety contains 1 to 3 carbon atoms mono- or di-alkylaminoalkyl wherein each alkyl moiety contains 1 to 3 carbon atoms, N-pyrrolidino, N-piperidino, N-morpholino, aryl or arylalkyl (wherein the aryl moiety is phenyl, pyridyl, or a 5-membered heteroaromatic ring which is either unsubstituted or substituted by alkyl or alkyloxy of 1 to 3 carbon atoms, hydroxy, amino, or halogen, and the alkyl moiety contains 1 to 3 carbon atoms which may be unsubstituted or substituted with a methyl, hydroxy, or amino groups), halogen, cyano, nitro, azido or carboxy; or, $R^5$ is hydrogen and $R^3$ and $R^4$ are joined to form a cycloalkyl with a 3 or 4 carbon bridge; or, $R^3$ is hydrogen and $R^4$ and $R^5$ are joined to form a cycloalkyl with a 3 or 4 carbon bridge; or, $R^3$, $R^4$, and $R^5$ are each hydrogen;

$R^6$ and $R^7$ are each hydrogen.

A particular subgeneric aspect of the invention comprises compounds of formula 1, wherein, A is a connecting chain of 1 to 3 atoms, wherein one of the atoms is oxygen, nitrogen as —NH— or —NCH$_3$—, or sulfur as —S—, —SO—, or —SO$_2$—, and the remaining atoms are carbon as —CH$_2$—, with the proviso that any of the oxygen, nitrogen or sulfur atoms are not attached directly to the tricyclic nucleus; or A is —CH=CH— wherein the alkene is of cis stereochemistry; or —CH$_2$—, —CH$_2$CH$_2$—, —CH$_2$CH$_2$CH$_2$—, wherein one of the carbon atoms is optionally substituted by oxo, hydroxy, halogen or amino; or A is a 1,2-cis-disubstituted cyclopropyl or oxiranyl ring;

D, E, G, L and M form a six-membered aromatic ring of type II, wherein D, E, G, L, and M are carbon, of which one of these carbon atoms is optionally unsubstituted or substituted with methyl, ethyl, amino, methyl- or ethylamino, acetamido, acetamidomethyl, acetyl, acetyloxy, hydroxy, halogen, trifluoromethyl, hydroxymethyl, methoxy, ethoxy, methyl- or ethylthio, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, or cyano, and of which a second of these carbon atoms is optionally unsubstituted or substituted with methyl or ethyl; or, D, E, G, L and M form a six-membered heteroaromatic ring of type II, wherein one of D, E, or G is nitrogen (optionally unoxidized or oxidized to the corresponding N-oxide), and the four remaining positions are carbon, of which one of these carbon atoms is optionally unsubstituted or substituted with methyl or amino; and, $R^1$ is hydrogen, alkyl of 1 to 3 carbon atoms or allyl;

Z is oxygen;

$R^2$ is alkyl of 2 to 3 carbon atoms, or cycloalkyl of 3 to 4 carbon atoms;

$R^4$ is hydrogen, methyl, or chloro;

$R^3$ is hydrogen, methyl, trifluoromethyl, or chloro, with the proviso that $R^3$ is not trifluoromethyl or chloro when $R^4$ is chloro;

$R^5$ is hydrogen, fluoro, or chloro;

$R^6$ and $R^7$ are hydrogen.

Preferred compounds of formula I are:

2-Chloro-5,11-dihydro-11-ethyl-5-methyl-8-[2-(pyrid-4-yl)ethyl]-6H-dipyrido[3,2-b:2',3'-e][1,4]diazepin-6-one;

5,11-Dihydro-11-ethyl-2-fluoro-5-methyl-8-[2-(pyrid-4-yl)ethyl]-6H-dipyrido[3,2-b:2',3'-e][1,4]diazepin-6-one;

2-Chloro-5,11-dihydro-11-ethyl-8-[2-hydroxy-2-(pyrid-4-yl)ethyl]-5-methyl-6H-dipyrido[3,2-b:2',3'-e][1,4]diazepin-6-one;

2-Chloro-5,11-dihydro-11-ethyl-8-[2-hydroxy-2-(N-oxo-pyrid-4-yl)ethyl]-5-methyl-6H-dipyrido[3,2-b:2',3'-e][1,4]diazepin-6-one;

5,11-Dihydro-11-ethyl-2-fluoro-8-[2-(N-oxo-pyrid-4-yl)ethyl]-5-methyl-6H-dipyrido[3,2-b:2',3'-e][1,4]diazepin-6-one;

5,11-Dihydro-11-ethyl-2-fluoro-8-[2-hydroxy-2-(pyrid-4-yl)ethyl]-5-methyl-6H-dipyrido[3,2-b:2',3'-e][1,4]diazepin-6-one;

5,11-dihydro-11-ethyl-2-fluoro-5-methyl-8-((N-oxo-pyrid-4-yl)oxy)methyl-6H-dipyrido[3,2-b:2',3'-e][1,4]diazepin-6-one;

2-chloro-5,11-dihydro-11-ethyl-5-methyl-8-[2-(N-oxo-pyrid-4-yloxy)ethyl]-6H-dipyrido[3,2-b:2',3'-e][1,4]diazepin-6-one;

8-(3-aminophenyloxy)methyl-2-chloro-5,11-dihydro-11-ethyl-5-methyl-6H-dipyrido[3,2-b:2',3'-e][1,4]diazepin-6-one;

2-chloro-5,11-dihydro-11-ethyl-5-methyl-8-(phenylthio)methyl-6H-dipyrido[3,2-b:2',3'-e][1,4]diazepin-6-one;

2-chloro-5,11-dihydro-11-ethyl-5-methyl-8-(pyrid-4-ylthio)methyl-6H-dipyrido[3,2-b:2',3'-e][1,4]diazepin-6-one;

2-chloro-5,11-dihydro-11-ethyl-5-methyl-8-(pyrid-4-yloxy)methyl-6H-dipyrido[3,2-b:2',3'-e][1,4]diazepin-6-one;

5,11-dihydro-11-ethyl-2-fluoro-5-methyl-8-(pyrid-4-yloxy)methyl-6H-dipyrido[3,2-b:2',3'-e][1,4]diazepin-6-one;

2-chloro-5,11-dihydro-11-ethyl-5-methyl-8-[2-(pyrid-4-yloxy)ethyl]-6H-dipyrido[3,2-b:2',340 -e][1,4]diazepin-6-one;

2-chloro-5,11-dihydro-11-ethyl-5-methyl-8-((N-oxo-pyrid-4-yl)methoxy)methyl-6H-dipyrido[3,2-b:2',3'-e][1,4]diazepin-6-one;

2-chloro-5,11-dihydro-11-ethyl-5-methyl-8-(pyrid-4-ylmethoxy)methyl-6H-dipyrido[3,2-b:2',3'-e][1,4]diazepin-6-one;

5,11-dihydro-11-ethyl-2-fluoro-5-methyl-8-[2-(N-oxo-pyrid-4-yloxy)ethyl]-6H-dipyrido[3,2-b:2',3'-e][1,4]diazepin-6-one;

8-(3-aminophenyloxy)methyl-5,11-dihydro-11-ethyl-2-fluoro-5-methyl-6H-dipyrido[3,2-b:2',3'-e][1,4]diazepin-6-one;

5,11-dihydro-11-ethyl-2-fluoro-5-methyl-8-(phenylthio)methyl-6H-dipyrido[3,2-b:2',3'-e][1,4]diazepin-6-one;

5,11-dihydro-11-ethyl-2-fluoro-5-methyl-8-(pyrid-4-ylthio)methyl-6H-dipyrido[3,2-b:2',3'-e][1,4]diazepin-6-one;

5,11-dihydro-11-ethyl-2-fluoro-5-methyl-8-[2-(pyrid-4-yloxy)ethyl]-6H-dipyrido[3,2-b:2',3'-e][1,4]diazepin-6-one;

5,11-dihydro-11-ethyl-2-fluoro-5-methyl-8-((N-oxo-pyrid-4-yl)methoxy)methyl-6H-dipyrido[3,2-b:2',3'-e][1,4]diazepin-6-one; and 5,11-dihydro-11-ethyl-2-fluoro-5-methyl-8-(pyrid-4-ylmethoxy)methyl-6H-dipyrido[3,2-b:2',3'-e][1,4]diazepin-6-one.

Synthesis Of Compounds Of Formula 1 And Their Salts

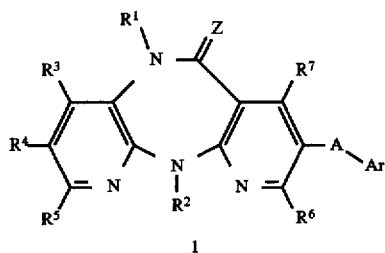

1

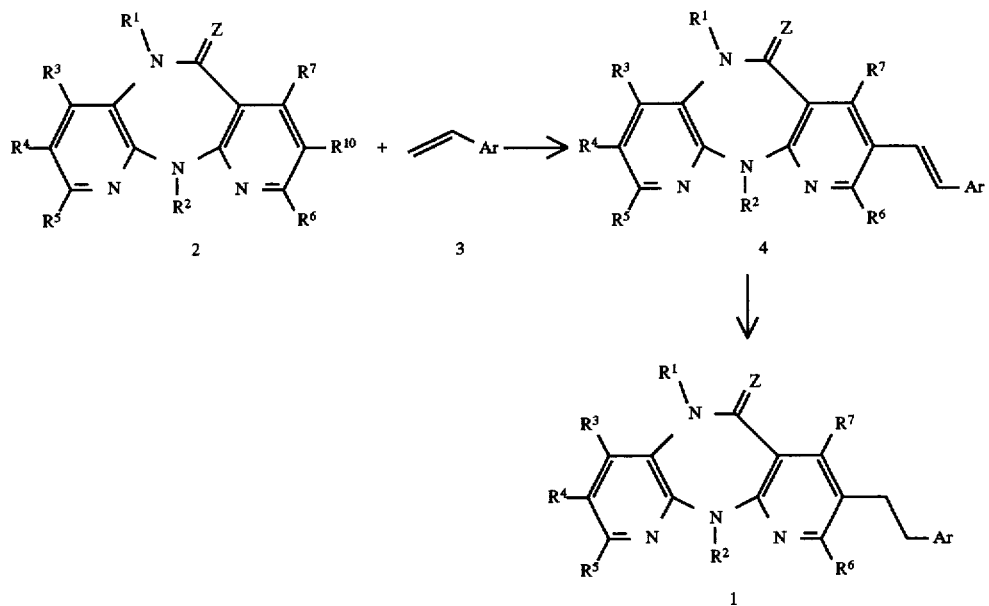

The compounds of Formula 1 and their salts can be prepared by known methods or obvious modifications thereof. Methods A–J, described below, are illustrative of the methods for preparing the compounds. Other applications of the coupling reactions described below are known; examples are contained in R. F. Heck, *Organic Reactions*, 1982, 27, 345; K. Sonogashira, in 'Comprehensive Organic Synthesis', ed. B. M. Trost, I. Fleming, and G. Pattenden, Pergamon, Oxford, 1991, vol. 3, p. 521; and K. Tamao, in 'Comprehensive Organic Synthesis', ed. B. M. Trost, I. Fleming, and G. Pattenden, Pergamon, Oxford, 1991, vol. 3, p. 435.

Method A

Compounds of formula 1, wherein A is an alkyl chain of 2 carbon atoms and Ar, Z, and $R^1$ through $R^7$ are as defined above, may be obtained by coupling compounds of formula 2, wherein Z, and $R^1$ through $R^7$ are as defined above and $R^{10}$ is bromo or iodo, with vinyl aromatic compounds of formula 3, wherein Ar is as defined above, to provide olefins of formula 4. The preparation of compounds 1 from the olefins 4 may be accomplished by standard methods of catalytic hydrogenation, such as will be familiar to those skilled in the art.

The coupling reaction is generally achieved by condensing compounds 2 and 3 in the presence of a palladium catalyst, such as tetrakis(triphenylphosphine)palladium(0), tetrakis(triphenylarsine)palladium(0), tetrakis(tri-2-furylphosphine)palladium(0), palladium(II) acetate, or bis(triphenylphosphine)palladium(II) chloride, and a base, such as triethylamine, N,N-diisopropylethylamine, sodium acetate, sodium bicarbonate, or the like. In some cases, a phase-transfer agent, such as a tetraalkylammonium salt, may also be present in the reaction mixture. These reactions are generally carried out in inert solvents such as 1,4-dioxane, tetrahydrofuran, N,N-dimethylformamide, N-methylpyrrolidinone, and the like, at temperatures generally between room temperature and the boiling point of the solvent. The reaction may be carried out in a sealed tube or under an inert atmosphere such as nitrogen or argon.

The reduction step is generally carried out by the method of transfer hydrogenation over a heterogeneous palladium or platinum catalyst at atmospheric pressure in the presence of a hydrogen donor, such as cyclohexene, sodium hypophosphite, ammonium formate, or the like. The reaction is generally carried out in an inert solvent such as tetrahydrofuran, 1,4-dioxane, ethyl acetate, methanol, ethanol, or the like, and reaction temperatures are generally between 40° C. and the boiling point of the solvent. Alternatively, the reduction step may be accomplished over a heterogeneous palladium or platinum catalyst in a solvent such as ethanol, methanol, ethyl acetate, acetic acid or the like and under an atmosphere of hydrogen. The reaction temperatures are generally between 25° C. and 100° C. and reaction pressures are generally between 50 p.s.i. and 150 p.s.i.

Method B

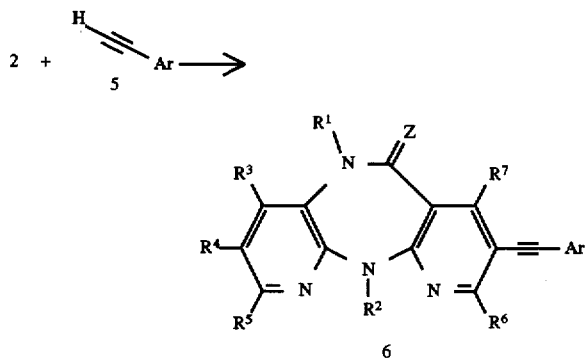

In an alternative method, compounds of formula 1, wherein A is an alkyl chain of 2 carbon atoms and Ar, Z, and $R^1$ through $R^7$ are as defined above, may be obtained from compounds of formula 2, which are as defined above, and compounds of formula 5, wherein Ar is as defined above, in a manner analogous to that of Method A. The coupling reaction is generally carried out in the presence of a palladium catalyst and a base, as described for Method A. Inert solvents such as 1,4-dioxane, tetrahydrofuran, N,N-dimethylformamide, N-methylpyrrolidinone, and the like, are generally used, and the reaction temperatures are generally between 50° C. and 150° C. In some cases, copper(I) iodide may be added to the reaction mixture, in which case the reaction temperature is generally between 25° C. and 100° C. The reduction of an acetylene of formula 6 is generally carried out in a manner analogous to reduction of the olefins of formula 4, as described for Method A.

Method C

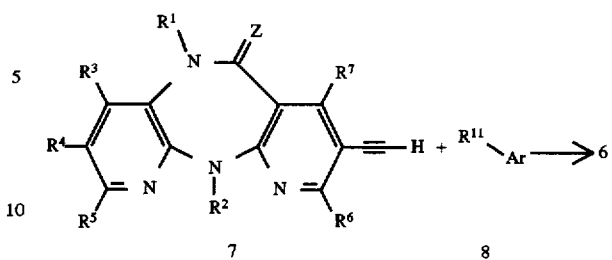

In an alternative method, intermediates of formula 6, which are as defined above, may be obtained by coupling acetylenes of formula 7 wherein Z and $R^1$ through $R^7$ are as defined above, with an aryl halide of formula 8, wherein Ar is as defined above and $R^{11}$ is bromo or iodo, or $R^{11}$ is chloro with the proviso that at least one of B and G is nitrogen. The coupling reaction is carried out as in Method B. The acetylenes of formula 7 may be obtained by coupling compounds of formula 2, which are as defined above, with trimethylsilylacetylene in the presence of a palladium catalyst such as tetrakis(triphenylphosphine)palladium(0), tetrakis(triphenylarsine)palladium(0), tetrakis(tri-2-furylphosphine)palladium(0), or bis(triphenylphosphine) palladium(II) chloride and a base, such as triethylamine, N,N-diisopropylethylamine, diethylamine, ethylamine, butylamine, and the like. The reactions may be performed in the presence or absence of copper(I) iodide and are generally carried out in inert solvents such as 1,4-dioxane, tetrahydrofuran, N,N-dimethylformamide, N-methylpyrrolidinone, and the like, at temperatures between 25° C. and 100° C. The trimethylsilyl group of the coupled product can be cleaved by treatment with a fluoride reagent, such as tetrabutylammonium fluoride, in an inert solvent, such as tetrahydrofuran.

Method D

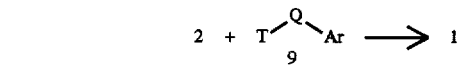

In an alternative method, compounds of formula 1, in which A is an alkyl chain of 1 to 4 carbon atoms may be obtained by coupling compounds of formula 2, which are as defined above, with organometallic reagents of formula 9, wherein Ar is as defined above, Q is an alkyl chain of 1 to 4 carbon atoms, or alkenyl or alkynyl of 2 to 4 carbon atoms, and T is a metal atom such as boron, zinc, tin, magnesium, or the like. It will be obvious to those skilled in the art that the metal may also bear additional ligands, such as alkyl, alkoxide, or halide groups, or the like. The coupling reaction is carried out in the presence of a palladium catalyst, such as tetrakis(triphenylphosphine)palladium(0), tetrakis (triphenylarsine)palladium(0), tetrakis(tri-2-furylphosphine) palladium(0), bis(triphenylphosphine)palladium(II) chloride, or [1,1'-bis(diphenylphosphino)ferrocene] palladium(II) chloride, in an inert solvent such as 1,4-dioxane, tetrahydrofuran, N,N-dimethylformamide, N-methylpyrrolidinone, and the like. The reactions are generally carried out under an inert atmosphere of nitrogen or argon and at temperatures between 25° C. and the boiling point of the solvent.

Method E

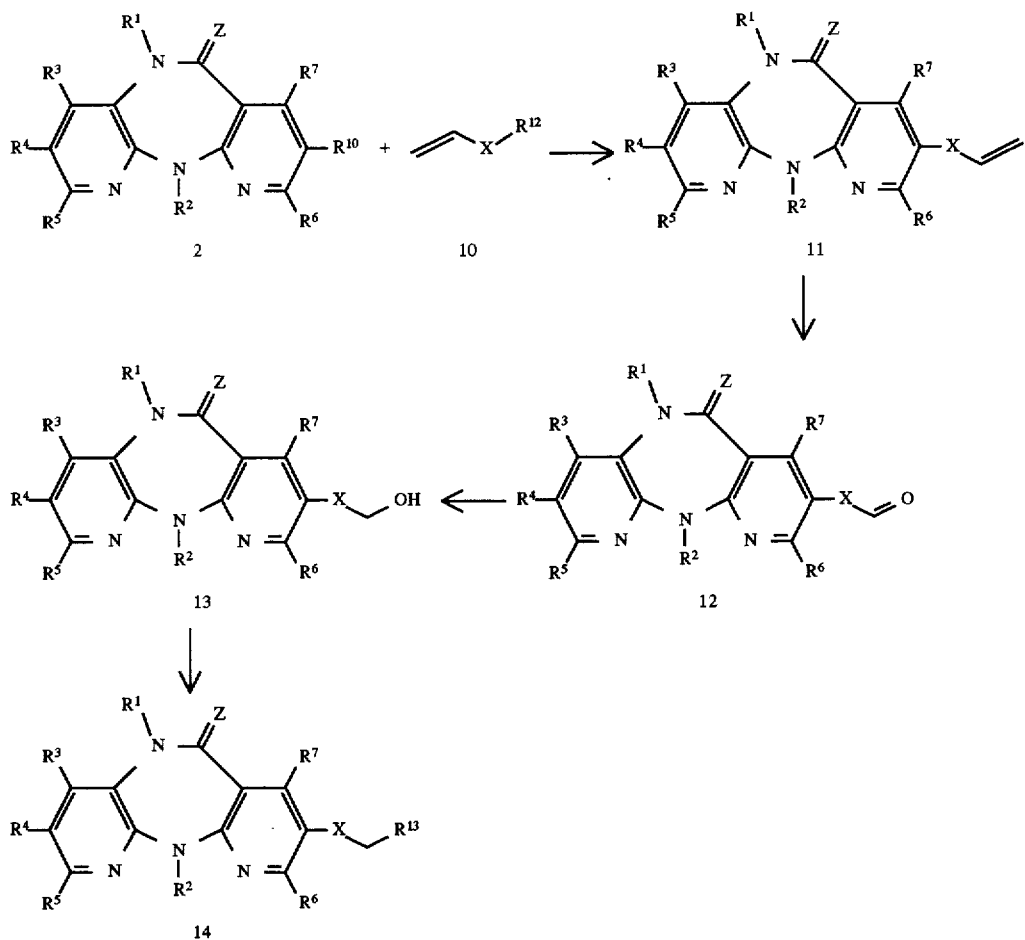

In an alternative method, intermediates of formulas 12, 13, 14 wherein X is defined as either a carbon atom or a bond may be obtained from the coupling of compounds of formula 2, which are as defined above, with alkenylorganotin or alkenylorganoboron compounds of formula 10, wherein X is defined as either a carbon atom or a bond and $R^{12}$ is defined as trialkyltin (i.e. $(CH_3CH_2CH_2CH_2)_3Sn$) or boronic acid (i.e. $(HO)_2BCHCH_2$), to provide olefins of formula 11. Preparation of aldehydes of formula 12 can be accomplished by standard oxidative cleavage of olefins of formula 11. Standard methods of carbonyl reduction will provide alcohols of formula 13 from aldehydes of formula 12. The hydroxy compounds 13 can be converted to alkyl halides of formula 14, wherein $R^{13}$ is chloro, bromo, iodo, through standard methods, such as will be familiar to those skilled in the art.

The coupling reaction is generally achieved by condensing compounds of formula 2 and of formula 10 in the presence of a palladium catalyst, such as tetrakis(triphenylphosphine)palladium(0), tetrakis(triphenylarsine)palladium(0), tetrakis(tri-2-furylphosphine)palladium(0), palladium(II) acetate, or bis(triphenylphosphine)palladium (II) chloride, and when $R^{12}$ is defined as boronic acid (i.e. $(HO)_2BCHCH_2$) the addition of a base, such as sodium carbonate, sodium bicarbonate, sodium hydroxide, potassium fluoride, potassium phosphate or the like. These reactions are generally carried out in inert solvents such as 1,4-dioxane, tetrahydrofuran, N,N-dimethylformamide, N-methylpyrrolidinone, and the like, at temperatures generally between room temperature and the boiling point of the solvent. The reaction may be carried out under an inert atmosphere such as nitrogen or argon.

The oxidative cleavage step is generally carried out by ozonolysis of compounds of formula 11 in a solvent such as dichloromethane or methanol or mixture thereof or the like. The reaction temperatures are generally between −78° C. and −25° C. followed by a warming to ambient temperature. The resulting ozonide and excess ozone are reduced by dimethylsulfide to produce compounds of formula 12. Alternatively, the oxidative cleavage may be accomplished through an oxidative cleavage as outlined by R. Pappo et al, *J. Org. Chem.* 1956, 21, 478. This entails treatment of compounds of formula 11 with osmium tetroxide usually in the presence of a cooxidant such as a triaklylamine N-oxide (i.e. N-methylmorpholine N-oxide), and sodium periodate.

The reduction of compounds of formula 12 is generally accomplished with a hydride reagent such as sodium borohydride, lithium aluminum hydride, diisobutylaluminum hydride or the like to provide hydroxy compounds of formula 13. The reactions are carried out in an inert solvent such as tetrahydrofuran, diethyl ether, toluene or the like at temperatures ranging from −78° to 0° C. and under an inert atmosphere such as nitrogen or argon.

The synthesis of compounds of formula 14 is generally achieved by the treatment of compounds of formula 13 with halogenating reagents such as thionyl chloride, sulfuryl chloride or the like. The reactions are generally carried out in solvents such as chloroform, dichloromethane at temperatures ranging from −20° to 0° C. and under an inert atmosphere such as nitrogen or argon. Other methods of conversion of hydroxy compounds to leaving group could be employed, such as will be familiar to those skilled in the art.

Method F

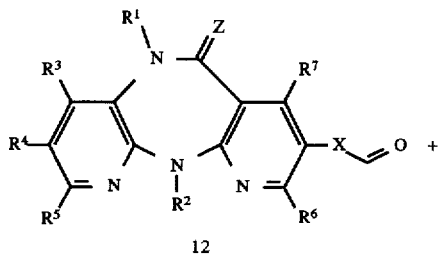

12

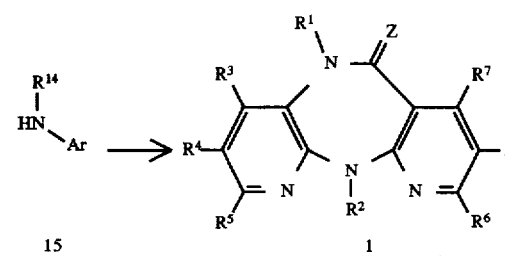

15  1

In an alternative method, compounds of formula 1 wherein A is a connecting chain of 2 to 3 atoms, wherein one atom is a nitrogen (unsubstituted or substituted with methyl or acetyl) and Ar, Z and $R^1$ through $R^7$ are as defined above, may be obtained from compounds of formula 12, which are as defined above and compounds of formula 15, wherein Ar are as defined above and $R^{14}$ is defined as hydrogen or methyl, via reductive amination.

The reductive aminations are generally accomplished by reacting aldehydes of formula 12 with an amines of formula 15, in an alcoholic solvent, such as ethanol, methanol or the like, in the presence of a reducing agent, such as sodium cyanoborohydride, sodium triacetoxyborohydride or the like, and catalytic acid, such as acetic acid, trifluoroacetic acid or the like. When $R^{14}$ is defined as hydrogen then the product 1 obtained may be alkylated or acylated through standard methods, such as will be familiar to those skilled in the art.

Method G

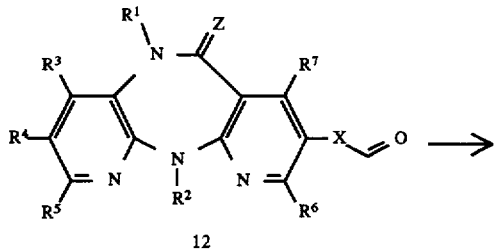

12

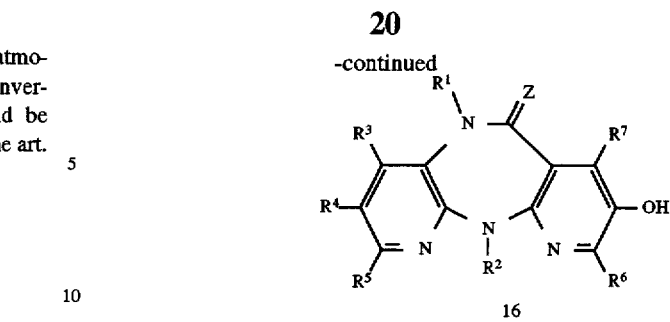

16

In an alternative method, intermediates of formula 16, wherein $R^1$ through $R^7$ and Z are as defined above, may be obtained by a standard Baeyer-Villiger reaction of intermediates of formula 12, wherein X is defined as a bond, $R^1$ through $R^7$ and Z are as defined above, followed by hydrolysis.

Compounds of formula 12 are treated with a peracid such as m-chloroperbenzoic acid, peracetic acid or the like in an inert solvent such as dichloromethane, chloroform, at temperatures ranging from −20° C. to room temperature. The reactions are generally carried out under an inert atmosphere such as nitrogen or argon.

Method H

In an alternative method, compounds of formula 1, wherein A is a connecting chain of 1 to 3 atoms, wherein one of the atoms is oxygen and the remaining atoms are carbon and B, D, E, F, G, Z and $R^1$ through $R^7$ are as defined above, may be obtained by functionalization of compounds of formula 13, as defined above, or 16, as defined above.

Compounds of formulas 13 or 16 are generally alkylated, arylated, or acetylated by known per se methods, such as will be familiar to those skilled in the art. The reactions are generally performed in solvents such as tetrahydrofuran, N,N-dimethylformamide, dimethyl sulfoxide or the like. Alcohols of formulas 13 or 16 in these solvents are treated with a base such as sodium hydride, potassium hydride, lithium, potassium or sodium bis(trimethylsilyl)amide, lithium diisopropylamide or the like followed by alkylating reagents, such as benzyl bromide, or arylating reagents such as 4-nitropyridine N-oxide, 4-nitro-2-picoline and the like, or acylating agents such as benzoyl chloride or the like. The reactions are generally carried out at temperatures ranging from −20° C. to the boiling point of the solvent and under an inert atmosphere such as nitrogen or argon.

Method I

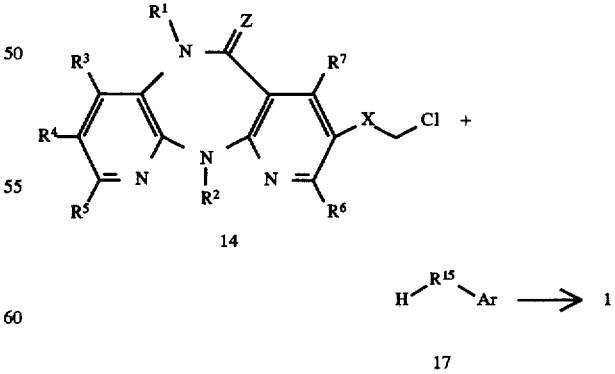

17

In an alternative method, compounds of formula 1, wherein A is a connecting chain of 1 to 3 atoms, wherein one of the atoms is oxygen, phosphorous or sulfur (optionally oxidized or unoxidized), or nitrogen (unsubstituted or substituted with methyl or acetyl), and the remaining atoms are carbon, may be obtained from compounds of formula 14, as defined above and compounds of the general formula 17 wherein Ar is defined as above, $R^{15}$ is defined as oxygen, phosphorous or sulfur (optionally oxidized or unoxidized), or nitrogen (unsubstituted or substituted with methyl or acetyl) by known per se methods.

Compounds of formula 17, wherein Ar is defined as above, and $R^{15}$ is defined as oxygen or sulfur, are treated with a base, such as sodium hydride, potassium hydride, lithium, potassium or sodium bis(trimethylsilyl)amide, lithium diisopropylamide or the like, followed by the addition of compounds of formula 14, as defined above. The reactions are generally performed in solvents such as tetrahydrofuran, N,N-dimethylformamide, dimethyl sulfoxide or the like. The reactions are generally carried out at temperatures ranging from room temperature to the boiling point of the solvent and under an inert atmosphere such as nitrogen or argon.

Compounds of formula 17, wherein Ar is defined as above, and $R^{15}$ is defined as nitrogen (unsubstituted or substituted with methyl or acetyl) are treated directly with compounds of formula 14, as defined above. The reactions are generally run with 17 as the solvent when possible or in solvents such as tetrahydrofuran, N,N-dimethylformamide, dimethyl sulfoxide or the like. The reactions are generally carried out at temperatures ranging from room temperature to the boiling point of the solvent and under an inert atmosphere such as nitrogen or argon.

Method J

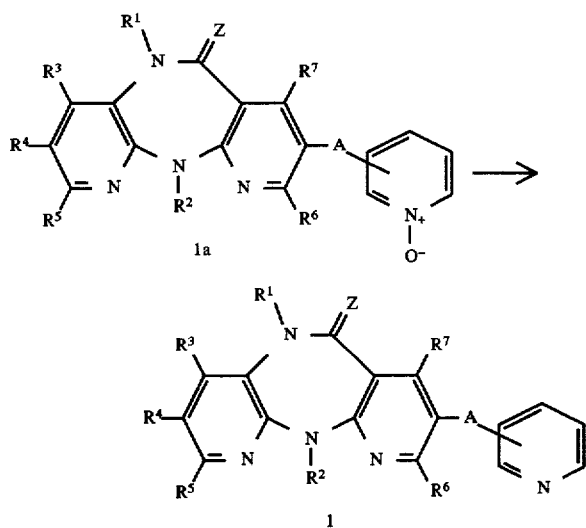

In an alternative method, compounds of formula 1, wherein A, Z and $R^1$ through $R^7$ are as defined above, by reduction of compounds of the formula 1 a with known per se methods, such as will be familiar to those skilled in the art.

The compounds of formula 1a are generally reduced with reagents, such as phosphorus trichloride, phosphorus tribromide, 2,4-bis(4-methoxyphenyl)-1,3-ditia-2,4-diphosphetane-2,4-disulfide (Lawesson's reagent), or the like, in solvents, such as chloroform, dichloromethane, benzene or the like, at room temperature and under an inert atmosphere such as nitrogen or argon.

It will be obvious to those skilled in the art that in some instances the reactions described in Methods A–J cannot be effected in the presence of reactive intermediates incompatible with the reaction conditions. In such cases, the reactive substituent must first be derivatized via known per se methods to contain a suitable protective group, which can then be subsequently removed.

Biological Properties

The above described compounds of formula 1 possess inhibitory activity against HIV-1 reverse transcriptase. When administered in suitable dosage forms, they are useful in the treatment of AIDS, ARC and related disorders associated with HIV-1 infection. Another aspect of the invention, therefore, is a method for treating HIV-1 infection which comprises administering to a human being, infected by HIV-1, a therapeutically effective amount of a novel compound of formula 1, as described above. Whether it be termed treatment or prophylaxis, the compounds may also be used to prevent perinatal transmission of HIV-1 from mother to baby, by administration to the mother prior to birth.

The compounds of formula 1 may be administered in single or divided doses by the oral, parenteral or topical routes. A suitable oral dosage for a compound of formula 1 would be in the range of about 0.5 mg to 1 g per day. A preferred oral dosage for a compound of formula 1 would be in the range of about 100 mg to 800 mg per day for a patient weighing 70 kg. In parenteral formulations, a suitable dosage unit may contain from 0.1 to 250 mg of said compounds, preferably 1 mg to 200 mg, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula 1 can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered by suppository.

As stated before, the compounds provided by the invention inhibit the enzymatic activity of HIV-1 RT. Based upon testing of these compounds, as described below, it is known that they inhibit the RNA-dependent DNA polymerase activity of HIV-1 RT. It is known (data not shown) that they also inhibit the DNA-dependent DNA polymerase activity of HIV-1 RT. Utilizing the Reverse Transcriptase (RT) Assay described below, compounds can be tested for their ability to inhibit the RNA-dependent DNA polymerase activity of HIV-1 RT. Certain specific compounds described in the Examples which appear below, were so tested. The results of this testing appear in Table I, below.

The compounds of the invention are structurally related to the compounds of U.S. Pat. No. 5,366,972 which include the compound 11-cyclopropyl-5,11-dihydro-4-methyl-6H-dipyrido[3,2-b;2',3', -e][1,4]diazepine-6-one. That compound has been shown to be active in the same in vitro tests that have been used to illustrate the activity of the compounds of the present invention and has also shown to be active in the treatment of AIDS in human tests.

REVERSE TRANSCRIPT (RT) ASSAYS

Assay Theory:

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay, which has been previously described (2), and is based upon the observation that reverse transcriptase is able to use a synthetic template [poly r(C) primed with oligo d(G)] to transcribe a radio-labelled, acid-precipitable DNA strand utilizing $^3$H-dGTP as a substrate. The assay described below utilizes the wild type (WT) enzyme, which is the predominant form of the enzyme observed in patients infected with HIV-1. Utilization of the mutant RT enzyme (Y181C, prepared by site-directed mutagenesis in which the tyrosine residue at codon 181 has been replaced by a cysteine residue) and analogous assay conditions allows compounds to be evaluated for their effectiveness at inhibiting this mutant enzyme.

Materials:

a) Preparation of the enzyme

The HIV-1 RT expression clone, pKRT2, was obtained from Yale University (3). An overnight culture, grown in 2×YT medium (37° C., 225 rpm) (4), supplemented with 100 µg/mL ampicillin for positive selection was used to inoculate the 2×YT medium. The culture is incubated (37° C., 225 rpm) until it reaches an $OD_{600}$ of 0.6–0.9. At that time the repressor inhibitor IPTG (isopropyl β-D-thiogalactopyranoside) is added to 0.5 mM, and the mixture is incubated for 2 additional hours.

b) Purification of Enzyme

Purification of recombinant reverse transcriptase was performed using a combination of methods previously described (5). This procedure is summarized briefly as follows: Bacteria were pelleted E. Coli containing RT-1 wt or RT-1 (Y181 C) were suspended in 50 mM MES, pH 6.0 containing 10% glycerol, lysed in a french press, centrifuged, and the supernates discarded. Lysate pellets were extracted with buffer A (50 mM MES, pH 6.0, 100 mM KCl, 50 mM KPi, 10% glycerol, 0.02% hexyl β-glucoside), and re-centrifuged; nucleic acid in supernates was precipitated with 0.1% polyethylenimine. Clarified extracts were chromatographed on hydroxylapatite (BioRad BioGel HT) using a gradient of 0–0.25M KPi in buffer A. Fractions containing RT were pooled, diluted with an equal volume of buffer B (50 mM Bis-tris propane, pH 7.0, 100 mM $(NH_4)_2SO_4$, 10% glycerol), and loaded onto a Heparin-Sepharose CL-6B (Pharmacia) column. Bound RT was eluted with a gradient of 0 to 1.0M $(NH_4)_2SO_4$ in buffer B. Heparin-Sepharose fractions containing RT were concentrated (Amicon YM-30 membrane), combined with equal volumes of 2.0M $(NH_4)_2SO_4$ in buffer B and injected onto a 21.5×150 mm TSK Phenyl-5PW HIC HPLC column (Phenomenex). Heterodimeric RT was eluted using a descending gradient of 1.0M to 0M $(NH_4)_2SO_4$ in buffer B, concentrated, and stored at 4° C.

The products were 98% pure by SDS-PAGE and had near equivalent specific activities of ~20 nmol dGTP mg$^{-1}$ min$^{-1}$ at 25° C.

b) Composition of stock and reaction mixture

| Stock Reagent Concentrations | 2.4x Mix Concentration | Final Assay |
|---|---|---|
| 1M Tris pH 7.8 | 120 mM | 50 mM |
| 1M Dithiothrietol | 9.6 mM | 4 mM |
| 1M NaCl | 144 mM | 60 mM |
| 1M $MgCl_2$ | 4.8 mM | 2.0 mM |
| [poly r(C)$_{500}$/oligo d(G)$_{10}$] (27:1) | 11.6 µg/mL | 4.8 µg/mL |
| $^3$H-dGTP (93 [2M, 10.7 Ci/mmol) | 1.1 µM | 0.45 µM |
| Chaps | — | 0.02% |
| RT enzyme | — | 0.02% |
| RT enzyme | — | 0.63 nM |
| Test compound | — | 10 µg/mL |

Assay Procedure:

The 2.4× concentrated stock reaction mixture is aliquoted and stored at −20° C. The mixture is stable and thawed for use in each assay. This enzyme assay has been adapted to a 96 well microtiter plate system, and has been previously described (6). Tris buffer (50 mM, pH 7.8), vehicle (solvent diluted to match the compound dilution), or compounds in vehicle are dispensed into 96-well microtiter plates (10 µL/well; 3 wells/compound). The HIV-1 RT enzyme is thawed, diluted in 50 mM Tris pH 7.8 containing 0.05% Chaps to give 1.5 nM enzyme and 25 µL are dispensed per well. Ten µL of 0.5M EDTA are added to the first three wells of the microtiter plate. EDTA chelates the Mg$^{++}$ present and prevents reverse transcription. This group serves as background polymerization which is subtracted from all other groups. Twenty-five µl of the 2.4× reaction mixture are added to all wells and the assay is allowed to incubate at room temperature for 30 minutes. The assay is terminated by precipitating the DNA in each well with 60µL of sodium pyrophosphate (2% w/v) in 10% trichloracetic acid (TCA)

(10% w/v). The microtiter plate is incubated for 15 minutes at 4° C. and the precipitate is harvested onto #30 glass fiber paper (Schleicher & Schuell) using a Tomtech 96-well harvester. The filters are then dried, placed into plastic bags with Betaplate scintillation cocktail (Pharmacia/LKB) and counted in the Betaplate counter (Pharmacia/LKB).

The calculation for percent inhibition is as follows:

$$\% \text{ inhibition} = \frac{[\text{CPM Mean Test Value} - \text{CPM Mean Control Value}]}{\text{CPM Mean Control Value}} \times 100$$

REFERENCES

1. Benn, S., et al. *Science* 230:949, 1985.
2. Farmerie, W. G. et. al. *Science* 236:305, 1987.
3. D'Aquila, R. T. and Summers, W. C. *J. Acq. Imm. Def. Syn.* 2:579, 1989.
4. Maniatis, T, Fritsch, E. F., and J. Sambrook, eds. *Molecular Cloning: A Laboratory Manual*, Cold Spring Harbor Laboratory, 1982.
5. a) Warren, T. C. et al. *Protein Expression & Purification* 3:479, 1992; b) Kohlstaedt, L. A. *Science* 256(5065): 1783, 1992.
6. Spira, T., et. al. *J. Clinical Microbiology*, 25:97, 1987.

In order to confirm that compounds which are active in the RT Assay also have the ability to inhibit HIV replication in a living system, compounds according to the invention were also tested in the human T-Cell Culture (Syncytia) Assay described below. The results of this testing appear in Table I.

SYNCYTIA (HUMAN T-CELL CULTURE) ASSAY

Assay Theory:

Formation of syncytia is a feature of in vitro cultures of CD4+ T-cells infected with HIV-1. In this assay (1), T-cells are treated with a putative replication inhibiting compound and then infected with HIV-1. After incubation, the culture is checked for the formation of syncytia. The absence or reduction in the number of syncytia is used as a measure of the test compound's ability to inhibit HIV replication.

Assay Method:

The target cells, designated C8166-45, are a fusion of umbilical blood lymphocytes and T-cells from leukemia-lymphoma patients and are established at an initial density of $5 \times 10^4$ per 90 µl in RPMI 1640 (+10% fetal bovine serum) culture medium in 96 well flat bottom plates. A selected amount of test compound, dissolved in DMSO, is included. 50 $TCID_{50}$'s (the dose that results in induced effect in 50% of test cultures) of the HTLV-IIIB strain of HIV-1 (3) are inoculated into each culture. Control cultures receive compound or virus only.

The cultures are incubated for 72 hours (4), at 37° C. with 5% carbon dioxide, and then visually examined for the frequency and distribution of virus-induced giant cell syncytia. The percent inhibition by the test compound is determined by comparison with control values.

REFERENCES

1. Koup, R. A., et al. *J. I. D.*, 163:966, 1991.
2. Salahuddin, S. Z., et al. *Virology*, 129:51, 1983.
3. Shaw, G. M., Hahn, R. H., Arya, S. K., Groopman, J. E., Gallo R. C., and Wong-Staal, F. *Science* 226:1165, 1984.
4. Somasundaran, M. and Robinson, H. L. *Science* 242:1554, 1988.

In order to assess the specificity of the enzyme inhibitory activity of the compounds provided by the invention, a few were tested, using known per se assay methods, for their ability to inhibit Feline Leukemia Virus-derived reverse transcriptase and Calf Thymus-derived DNA alpha-polymerase. None of the compounds so tested was observed to possess any inhibitory activity against these enzymes. These results indicate that the enzyme inhibitory activity of the compounds provided by the invention is directed rather specifically against HIV-1 RT.

In order to roughly assess the cytotoxicity of the compounds provided by the invention, several such compounds were tested in the MTT Assay described below. The results of this testing are reported in Table I, below. Compounds having a relatively high $CC_{30}$ are preferred.

MTT ASSAY

Assay Theory:

The MTT [3-(4,5-dimethylthiazol-2-yl)-2,5-diphenyltetrazolium bromide] assay is based on cleavage of tetrazolium bromide by metabolically active cells, resulting in a highly quantitative blue color. This assay has been previously described (1) but has been optimized for the purposes of the testing reported herein.

Assay Method:

The C8166-45 cell line (2), a fusion of umbilical blood lymphocytes and T-cells from leukemia-lymphoma patients grown in RPMI 1640 supplemented with 10% fetal bovine serum, is used as the target cell line in the assay. Cells (100 µL) are plated in microtest plate wells at a concentration of $10^5$ cells per mL in the presence of varying concentrations of inhibitor in 50 µL of RPMI 1640. The cells are incubated at 37° C. in a humidified $CO_2$ incubator. Five days later, 20 µL of MTT (5 mg/mL in RPMI 1640, warmed, 0.2 micron filtered, and stored at 4° C.) is added to each well. After 4 hours additional incubation at 37° C., 60 µL of 0.01N HCl in 10% Triton X-100 is added to each well and thoroughly mixed to aid the solubilization of the crystals. A bunsen burner is briefly run across the top of the plate to disrupt bubbles and the plate is read at 600 nm after 10 minutes.

Analysis: The average blank reading is subtracted from all wells and inhibition is calculated according to the following formula:

$$\% \text{ inhibition} = 1 - \frac{\text{average compound value}}{\text{average control value}} \times 100$$

REFERENCES

1. Mosmann, T., *J. Immunol. Methods*, 65:55, 1983.
2. Salahuddin, S. Z., et al. *Virology*, 129:51, 1983.

TABLE I

| Ex. No. | RT (WT) Assay % inh. (1 µM) | RT (Y181C) Assay % inh. (1 µM) | Syncytia Assay $IC_{50}$ (µM) | MTT Assay $CC_{30}$ (µM) |
| --- | --- | --- | --- | --- |
| 1 | 32 | 39 | NT | NT |
| 2 | 95 | 82 | 0.02 | >60 |
| 3 | 95 | 87 | 0.01 | 70 |
| 4 | 82 | 82 | NT | NT |
| 5 | 68 | 53 | NT | NT |
| 6 | 21 | 2 | NT | >256 |
| 7 | 87 | 76 | NT | NT |
| 8 | 80 | 71 | NT | >256 |
| 9 | 87 | 77 | NT | 150 |

TABLE I-continued

| Ex. No. | RT (WT) Assay % inh. (1 µM) | RT (Y181C) Assay % inh. (1 µM) | Syncytia Assay IC$_{50}$ (µM) | MTT Assay CC$_{30}$ (µM) |
|---|---|---|---|---|
| 10 | 24 | 9 | NT | NT |
| 11 | 78 | 73 | NT | 150 |
| 12 | 94 | 90 | NT | 250 |
| 13 | 75 | 73 | NT | >128 |
| 14 | 72 | 23 | NT | NT |
| 15 | 77 | 55 | NT | NT |
| 16 | 41 | 22 | NT | NT |
| 17 | 91 | 83 | NT | NT |
| 18 | 92 | 71 | NT | NT |
| 19 | 89 | 73 | NT | NT |
| 20 | 65 | 17 | NT | NT |
| 21 | 98 | 91 | NT | NT |
| 22 | 90 | 86 | NT | 60 |
| 23 | 91 | 85 | NT | NT |
| 24 | 62 | 90 | NT | NT |
| 25 | 59 | 70 | NT | NT |
| 26 | 92 | 86 | NT | 35 |
| 27 | 24 | 17 | NT | NT |
| 28 | 58 | 57 | NT | NT |
| 29 | 90 | 73 | NT | >60 |
| 30 | 87 | 73 | NT | NT |
| 31 | 94 | 85 | NT | NT |
| 32 | 66 | 60 | NT | NT |
| 33 | 89 | 74 | NT | NT |
| 34 | 94 | 75 | NT | NT |
| 35 | 81 | 84 | NT | NT |
| 36 | 48 | 56 | NT | NT |
| 37 | 84 | 66 | NT | >60 |
| 38 | 96 | 95 | NT | 150–175 |
| 39 | 89 | 71 | NT | NT |
| 40 | 93 | 69 | NT | >20 |
| 41 | 97 | 87 | NT | 20 |
| 42 | 94 | 79 | 0.03 | NT |
| 43 | 80 | 56 | NT | NT |
| 44 | 79 | 13 | NT | NT |
| 45 | 96 | 86 | 0.01 | >60 |
| 46 | 76 | 76 | NT | >30 |
| 47 | 63 | 50 | NT | NT |
| 48 | 13 | 17 | NT | NT |
| 49 | 91 | 82 | NT | NT |
| 50 | 96 | 74 | NT | NT |
| 51 | 86 | 63 | NT | NT |
| 52 | 72 | 7 | NT | NT |
| 53 | 89 | 40 | NT | NT |
| 54 | 98 | 80 | NT | NT |
| 55 | 90 | 54 | NT | NT |
| 56 | 57 | 28 | NT | NT |
| 57 | 88 | 70 | NT | NT |
| 58 | 64 | 53 | NT | NT |
| 59 | 81 | 64 | NT | NT |
| 60 | 86 | 67 | NT | NT |
| 61 | 20 | 28 | NT | NT |
| 62 | 81 | 31 | NT | >130 |
| 63 | 97 | 86 | NT | NT |
| 64 | 94 | 36 | NT | >200 |
| 65 | 96 | 89 | NT | 230 |
| 66 | 88 | 89 | NT | 100 |
| 67 | 86 | 80 | NT | 128 |
| 68 | 88 | 66 | NT | NT |
| 69 | 95 | 81 | NT | >128 |
| 70 | 40 | 24 | NT | NT |
| 71 | 99 | 97 | NT | NT |
| 72 | 76 | 63 | NT | NT |
| 73 | 98 | 88 | NT | NT |
| 74 | 84 | 68 | NT | NT |
| 75 | 36 | 57 | NT | >130 |
| 76 | 98 | 57 | NT | >130 |
| 77 | 79 | 27 | NT | NT |
| 78 | 87 | 46 | NT | NT |
| 79 | 89 | 41 | NT | NT |
| 80 | 39 | 52 | NT | 65 |
| 81 | 85 | 75 | NT | NT |
| 82 | 65 | 60 | NT | >>256 |
| 83 | 47 | 30 | NT | NT |
| 84 | 85 | 67 | NT | NT |
| 85 | 73 | 70 | NT | >>256 |
| 86 | 80 | 74 | NT | 256 |
| 87 | 92 | 70 | NT | >>60 |
| 88 | 90 | 74 | NT | 60 |
| 89 | 38 | 31 | NT | 130 |
| 90 | 20 | 0 | NT | >60 |
| 91 | 94 | 67 | NT | >256 |
| 92 | 82 | 39 | NT | NT |
| 93 | 96 | 86 | NT | >256 |
| 94 | 95 | 86 | NT | 200 |
| 95 | 74 | 69 | NT | 100 |
| 96 | 97 | 97 | 0.03 | >256 |
| 97 | 84 | 45 | NT | >130 |
| 98 | 86 | 72 | NT | >>60 |
| 99 | 98 | 94 | 0.02 | 55 |
| 100 | 94 | 83 | 0.05 | >>60 |
| 101 | 24 | 11 | NT | >>60 |
| 102 | 69 | 61 | NT | >>60 |
| 103 | 71 | 53 | NT | >>60 |
| 104 | 97 | 86 | NT | 50 |
| 105 | 81 | 27 | NT | 40 |
| 106 | 83 | 66 | NT | >60 |
| 107 | 91 | 76 | NT | >>256 |
| 108 | 93 | 80 | NT | >>120 |
| 109 | 52 | 33 | NT | >60 |
| 110 | 25 | 2 | NT | >>250 |
| 111 | 59 | 23 | NT | >60 |
| 112 | 67 | 66 | NT | 250 |
| 113 | 87 | 79 | NT | 130 |
| 114 | 77 | 70 | NT | 30 |
| 115 | 91 | 87 | NT | 22 |
| 116 | 70 | 18 | NT | >>60 |
| 117 | 97 | 99 | 0.005 | 60 |
| 118 | 73 | 72 | NT | 45 |
| 119 | 83 | 86 | NT | NT |
| 120 | 98 | 97 | NT | NT |
| 121 | 96 | 89 | NT | 50 |
| 122 | 99 | 96 | nt | 25 |
| 123 | 96 | 93 | NT | 40 |
| 124 | 94 | 77 | 0.006 | >120 |
| 125 | 97 | 79 | NT | 160 |
| 126 | 85 | 82 | NT | 64 |
| 127 | 98 | 98 | 0.003 | 55 |
| 128 | 99 | 88 | NT | >256 |

EXAMPLES

The following examples further illustrate the present invention and will enable others skilled in the art to understand it more completely. It should be understood, however, that the invention is not limited to the particular examples given below. Procedures for preparing starting materials not described below may be found in U.S. Pat. No. 5,366,972.

Examples illustrating synthetic Method A

Example 1

5,11-Dihydro-11-ethyl-5-methyl-8-[trans-2-(pyrid-4-yl)ethen-1-yl]-6H H-dipyridol[3,2-b:2',3'-e][1,4]diazepin-6-one a) 2-Ethylamino-3-nitropyridine A stirred mixture of 2-chloro-3-nitropyridine (50.0 g, 0.32 mol), ethylamine (33.5 g, 0.74 mol), and xylenes (85 mL) was heated at 105° C. in a sealed vessel for three hours. After cooling, the solvent was removed in vacuo, and water was added to the residue. The product was extracted with methylene chloride, dried (sodium sulfate), and concentrated in vacuo to give 56.8 g of the title compound as a brown oil, suitable for use in the next reaction.

b) 3-Amino-2-ethylaminopyridine

A solution of 160 g (1.05 mol) of stannic chloride dihydrate in 200 mL of concentrated hydrochloric acid was added to 2-ethylamino-3-nitropyridine (52.7 g, 0.32 mol) in 650 mL of acetic acid, and the resultant mixture was stirred overnight at room temperature. The white precipitate was collected and washed with acetic acid. The collected solid was dissolved in 300 mL of water and the mixture was basified with 12N sodium hydroxide. The product was extracted with methylene chloride and the organic layer was washed with saturated aqueous sodium chloride, dried (sodium sulfate), and concentrated to give 34 g of solid. Recrystallization (ethyl acetate) afforded 28 g of 3-amino-2-ethylaminopyridine, suitable for use in the next reaction.

c) 2-Chloro-N-(2-ethylamino-3-pyridinyl)-5-nitro-3-pyridinecarboxamide

A solution of 2.21 g of 2-chloro-5-nitronicotinoyl chloride (obtained by nitration of 2-hydroxynicotinic acid, followed by conversion to 2-chloro-5-nitronicotinic acid, which was then treated with thionyl chloride) in 10 mL of tetrahydrofuran was slowly added over 15 minutes to a cooled, stirred mixture of 1.34 g of 3-amino-2-ethylaminopyridine, 1.29 g of diisopropylethylamine, and 40 mL of tetrahydrofuran. The resulting mixture was allowed to stir overnight at room temperature, and then was concentrated in vacuo. The title compound (2.30 g, m.p. 185°–186° C.), which precipitated out when the residue was treated with methylene chloride, was suitable for use in the next reaction.

d) 5,11-Dihydro-11-ethyl-8-nitro-6H-dipyrido[3,2-b:2',3'-e][1,4]diazepin-6-one A solution of 1.80 g of 2-chloro-N-(2-ethylamino-3-pyridinyl)-5-nitro-3-pyridinecarboxamide in 25 mL of xylenes was heated at reflux for four hours. After concentration in vacuo, the residue was purified on a silical gel column, eluting with 50% ethyl acetate/hexane, to give 0.93 g of the title compound.

e) 5,11-Dihydro-11-ethyl-5-methyl-8-nitro-6H-dipyrido[3,2-b:2',3'-e][1,4]diazapen-6-one Sodium hydride (60% oil dispersion, 1.0 g, 0.025 mol) was added to a solution of 5,11-dihydro-11-ethyl-8-nitro-6H-dipyrido[3,2-b:2',3'-e][1,4]diazepin-6-one (7.0 g, 0.025 mol) in 120 mL of N,N-dimethylformamide. After 1 hour, iodomethane (1.6 mL, 0.026 mol) was added, and the reaction mixture was stirred at room temperature overnight. The reaction mixture was diluted with water and extracted with ethyl acetate. The crude product was purified by flash chromatography, eluting with ethyl acetate/dichloromethane, to give 6.4 g of the title compound.

f) 8-Amino-5,11-dihydro-11-ethyl-5-methyl6H-dipyrido[3,2-b:2',3'-e][1,4]diazepin-6-one Following a procedure analogous to that described in Example 1b, 6.2 g of 5,11-dihydro-11-ethyl-5-methyl-8-nitro-6H-dipyrido[3,2-b:2',3'-e][1,4]diazepin-6-one was reduced to give, after recrystallization from 1,2-dichloroethane/hexane, 4.4 g of the title compound as a yellow powder, m.p. 189°–191° C.

g) 5,11-Dihydro-11-ethyl-8-iodo-5-methyl-6H-dipyrido[3,2-b:2',3'-e][1,4]diazepen-6-one A solution of sodium nitrite (0.14 g, 2.0 mmol) was added at 0° C. to 0.5 g (1.9 mmol) of 8-amino-5,11-dihydro-11-ethyl-5-methyl-6H-dipyrido[3,2-b:2',3'-e][1,4]diazepin-6-one in 4 mL of 10% sulfuric acid. After 20 min, sodium iodide (0.39 g, 2.6 mmol) was added and the mixture was warmed to room temperature. Extraction with dichloromethane and purification of the crude product by flash chromatography, eluting with ethyl acetate/dichloromethane, afforded 0.45 g of the title compound, m.p. 166°–168° C.

h) 5,11-Dihydro-11-ethyl-5-methyl-8-[trans-2-(4-pyridyl)ethen-1-yl]-6H-dipyrido[3,2-b:2',3'-e][1,4]diazepin-6-one A mixture containing 5,11-dihydro-11-ethyl-8-iodo-5-methyl-6H-dipyrido[3,2-b:2',3'-e][1,4]-diazepin-6-one (0.7 g, 1.9 mmol), 4-vinylpyridine (0.3 mL, 2.9 mmol), bis(triphenylphosphine)palladium(II) chloride (60 mg, 0.09 mmol), triethylamine (1.8 mL, 12.8 mmol), and 1 crystal of 2,6-di-tert-butyl-4-methylphenol in 4 mL of N,N-dimethylformamide was heated at 125° C. under argon for 3 hours. The reaction mixture was then cooled to room temperature, diluted with water, and extracted with ethyl acetate. The organic layer was washed with saturated aqueous sodium chloride, dried (magnesium sulfate), and concentrated to give a yellow oil. Purification by flash chromatography, eluting with ethyl acetate/hexanes, and recrystallization (ethyl acetate/hexanes) provided the 0.5 g of the title compound as yellow crystals, m.p. 150° C.

Example 2

5,11-Dihydro-11-ethyl-5-methyl-8-[2-(pyrid-4-yl)ethyl]-6H-dipyrido[3,2-b:2',3'-e][1,4]diazepin-6-one The title compound was prepared from 5,11-Dihydro-11-ethyl-5-methyl-8-[trans-2-(4-pyridyl)ethen-1-yl]-6H-dipyrido[3,2-b:2',3'-e][1,4]diazepin-6-one (0.38 g, 1.0 mmol) by catalytic hydrogenation over platinum oxide in ethyl acetate at 150 p.s.i. and 60° C. Recrystallization from ethyl acetate/hexanes afforded 0.18 g of the product as off-white crystals, m.p. 109°–110° C.

Example 3

2-Chloro-5,11-dihydro-11ethyl-5methyl-8-[2-(pyrid-4-yl)ethyl]-6H-dipyrido-[3,2-b:2',3'-e][1,4]diazepin-6-one a) 2-Chloro-5,11-dihydro-11-ethyl-8-[trans-2-(4-pyridyl)ethen-1-yl]-5-methyl-6H -dipyrido[3,2-b:2',3'-e][1,4]diazepin-6-one 2-Chloro-5,11-dihydro-11-ethyl-8-iodo-5-methyl-6H-dipyrido[3,2-b:2',3'-e][1,4]diazepin-6-one (prepared by procedures analogous to those described in Example 1a–g) (0.5 g, 1.2 mmol) was coupled with 4-vinylpyridine in the presence of bis(triphenylphosphine)palladium(II) chloride and triethylamine as described in example 1h to give 0.28 g of the title compound as brown crystals, m.p. 150°–152° C.

b) 2-Chloro-5,11-dihydro-11-ethyl-8-[2-(4-pyridyl)ethyl]-5-methyl-6H-dipyrido[3,2-b:2',3'-e][1,4]diazepin-6-one To a mixture of 2-chloro-5,11-dihydro-11-ethyl-8-[trans-2-(4-pyridyl)ethen-1-yl]-5-methyl-6H-dipyrido[3,2-b:2',3'-e][1,4]diazepin-6-one (2.3 g, 5.9 mmol) and palladium black (0.25 g) in 30 mL of 1,4-dioxane was added a solution of sodium hypophosphite (0.82 g 7.7 mmol) in 15 mL of water. The reaction mixture was heated at 80°–90° C. for 3 hours. The reaction mixture was then filtered through Celite and extracted with ethyl acetate. The product was purified by chromatography over silica gel, eluting with methanol/dichloromethane, and recrystallized from ethyl acetate/hexanes to give 1.75 g of the title compound as colorless crystals, m.p. 158°–159° C.

Example 4

2-Cyano-5,11-dihydro-11-ethyl-8-[2-(4-pyridyl)ethyl]-5-methyl-6H-dipyrido-[3,2-b:2',3'-e][1,4]diazepin-6-one A solution of 2-chloro-5,11-dihydro-11-ethyl-8-[2-(4-pyridyl)ethyl]-5-methyl-6H-dipyrido[3,2-b:2',3'-e][1,4]

diazepin-6-one (78 mg, 0.2 mmol), Sodium cyanide impregnated alumina (2 g/4 g, 0.44 g, 4.5 mmol), and tetrakis (triphenylphosphine)palladium(0) (45 mg, 0.04 mmol) in 5 mL of toluene was heated at 100° C. under argon for 8 hours. The reaction mixture was filtered, and the collected solid was washed with ethyl acetate. The filtrate was concentrated to give a yellow oil, which was purified by flash chromatography (elution with isopropannol-hexanes) and recrystallization (ethyl acetate-hexanes) to afford 11.5 mg (15%) of the title compound, m.p. 149°–150° C.

Example 5

2-Amino-5,11-dihydro-11-ethyl-8-[2-(4-pyridil) ethyl]-5-methyl-6H -dipyrido[3,2-b:2',3'-e][1,4] diazepin-6-one a) 2-(4-methoxybenzylamino)-5,11-dihydro-11-ethyl-8-[2-(4-pyridyl)ethyl]-5-methyl-6-H-dipyrido[3,2-b:2',3'-e][1,4]diazepin-6-one A mixture of 2-chloro-5,11-dihydro-11-ethyl-8-[2-(4-pyridyl)ethyl]-5-methyl-6H-dipyrido[3,2-b:2',3'-e][1,4] diazepin-6-one (0.285 g, 0.7 mmol) and 4-methoxybenzylamine (0.23 mL, 1.8 mmol) in 4 mL of xylenes was heated at 150° C. in a sealed tube. After 24 hours, additional amine (0.23 mL, 1.8 mmol) was added and the reaction temperature was increased to 250° C. Heat was removed after 2d, and the reaction mixture was washed with saturated aqueous ammonium chloride to remove excess amine. The organic layer was dried (magnesium sulfate) and concentrated. Purification by flash chromatography (elution with methanol-dichloromethane) afforded the title compound (0.09 g, 26%).

b) 2-Amino-5,11-dihydro-11-ethyl-8-[2-(4-pyridyl)ethyl]-5-methyl-6H-dipyrido[3,2-b:2',3'-e][1,4]diazepin-6-one 2-(4-methoxybenzylamino)-5,11-dihydro-11-ethyl-8-[2-(4-pyridyl)ethyl]-5-methyl-6H-dipyrido[3,2-b:2',3'-e][1,4] diazepin-6-one (0.09 g, 0.18 mmol) was treated for 20 h with trifluoroacetic acid (1 mL) under argon. After removal of excess TFA, the residue was stirred in dilute ammonium hydroxide for 5 hours. The product was extracted with ethyl acetate and purified by flash chromatography (elution with methanol-dichloromethane) to give the title compound (48 mg, 71%), m.p. 94°–97° C.

Example 6

5,11-Dihydro-11-ethyl-2-hydroxy-8-[2-(4-pyridil) ethyl]5-methyl-6H-dipyrido[3,2-b:2',3'-e][1,4] diazepin-6-one 2-Amino-5,11-dihydro-11-ethyl-8-[2-(4-pyridyl)ethyl]-5-methyl-6H-dipyrido[3,2-b:2',3'-e][1,4]diazepin-6-one (17 mg, 0.04 mmol) was dissolved in 1 mL of 35% sulfuric acid and the mixture was cooled to 0° C. An aqueous solution of sodium nitrite (3 mg, 0.04 mmol) was added slowly dropwise, and the reaction mixture was allowed to stir at room temperature. After 1½ hours, the reaction mixture was neutralized with sodium carbonate, and the product was extracted with ethyl acetate. Purification by flash chromatography (elution with methanol-dichloromethane) and recrystallization (diethyl ether-petroleum ether) afforded the title compound (8 mg, 53%), m.p. 200°–201° C.

Example 7

5,11-Dihydro-11-ethyl-2-iodo-8-[2-(4-pyridyl)ethyl]-5-methyl-6H-dipyrido[3,2-b:2',3'-e][1,4]diazepin-6-one a) 5,11-Dihydro-11-ethyl-8-[2-(4-pyridyl)ethyl]-2-trimethylstannyl-5-methyl-6H-dipyrido[3,2-b:2',3'-e][1,4] diazepin-6-one To a solution of 2-chloro-5,11-dihydro-11-ethyl-8-[2-(4-pyridyl)ethyl]-5-methyl-6H-dipyrido[3,2-b:2',3'-e][1,4] diazepin-6-one (60 mg, 0.15 mmol) in 3.5 mL of tetrahydrofuran under argon was added hexamethylditin (45 µL, 0.15 mmol) and tetrakis(triphenylphosphine)palladium(0) (10 mg, 0.0085 mmol), and the resultant mixture was heated at 85° C. in a sealed tube. After 22 hours, additional catalyst (10 mg) was added. Bis(triphenylphosphine)palladium(II) chloride (10 mg) was added after an additional 7 hours, and the temperature was increased to 100° C. After 40 h total reaction time, the reaction mixture was diluted with water and extracted with ethyl acetate. Purification by flash chromatography (elution with methanol-dichloromethane) afforded 47 mg of the title compound.

b) 5,11-Dihydro-11-ethyl-2-iodo-8-[2-(4-pyridyl)ethyl]-5-methyl-6H-dipyrido[3,2-b:2',3'-e][1,4]diazepin-6-one To a solution of 5,11-dihydro-11-ethyl-8-[2-(4-pyridyl) ethyl]-2-trimethylstannyl-5-methyl-6H-dipyrido[3,2-b:2',3'-e][1,4]diazepin-6-one (47 mg, 0.09 mmol) in chloroform was added a solution of iodine in chloroform (0.1M, 4 mL, 0.4 mmol). After 24 hours, the reaction mixture was washed with saturated aqueous KF, 5% NaHSO₃, and saturated aq. sodium chloride. Purification by flash chromatography (elution with methanol-dichloromethane) and recrystallization (ethyl acetate-hexanes) afforded 15 mg (21%) of the title compound, m.p. 174° C.

Example 8

2-Chloro-5,11-dihydro-11-ethyl-8-[2-(4-(N-oxopyridyl))ethyl]-5-methyl-6H-dipyrido[3,2-b:2',3'-e][1,4]diazepin-6-one To a solution of 2-chloro-5,11-dihydro-11-ethyl-5-methyl-8-[2-(4-pyridyl)ethyl]-6H-dipyrido[3,2-b:2',3'-e][1,4]diazepin-6-one (0.42 g, 11.07 mmol) in 8 mL of dichloromethane at 0° C. was added m-chloroperbenzoic acid (55%, 0.42 g, 1.34 mmol). The reaction mixture was stirred for 45 min at 0° C. and for 45 min at room temperature. The reaction mixture was then washed with saturated aq. sodium bicarbonate and 5% aq. NaHSO₃, dried (magnesium sulfate), and concentrated. Purification by flash chromatography (elution with methanol-dichloromethane) and recrystallization (ethanol-hexanes) afforded 0.29 g (66%) of the title compound, m.p. 205°–206° C.

Example 9

2-Chloro-5,11-dihydro-11-ethyl-8-[2-hydroxy-2-(pyrid-4yl)ethyl-]5methyl-6H-dipyridol[3,2-b:2',3'-e] [1,4]diazepin-6-one a) 2-Chloro-5,11-dihydro-11-ethyl-5-methyl-8-[2-acetoxy-2-(4-pyridyl)ethyl]-6H-dipyrido[3,2-b:2',3'-e][1,4 ]diazepin-6-one A solution of 2-chloro-5,11-dihydro-11-ethyl-5-methyl-8-[2-(4-N-oxopyridyl)ethyl]-6H-dipyrido[3,2-b:2',3'-e][1,4] diazepin-6-one (1.47 g, 3.59 mmol) and acetic anhydride (1.7 mL, 18.0 mmol) in 50 mL of acetic acid was heated at 100° C. for 11 hours. Solvents were removed by rotary evaporation, and the residue was dissolved in ethyl acetate. The resultant solution was washed with water, saturated aq. sodium bicarbonate, and saturated aq. sodium chloride, dried (magnesium sulfate), and concentrated. Purification by flash chromatography (elution with methanol-dichloromethane) and recrystallization (ethyl acetate-hexanes) afforded the title compound (0.89 g, 55%) as yellow crystals, m.p. 157°–158° C.

b) 2-Chloro-5,11-dihydro-11-ethyl-5-methyl-8-[2-hydroxy-2-(4-pyridyl)ethyl]-6H-dipyrido[3,2-b:2',3'-e][1,4]diazepin-6-one The product of example 9a (1.26 g, 2.8 mmol) was dissolved in 50 mL of methanol and 2 mL of water. Potassium carbonate (0.72 g, 5.2 mmol) was added, and the mixture was stirred at room temperature for 1.5 hours. The reaction mixture was diluted with water and the product was extracted with ethyl acetate. Purification by flash chromatography (elution with methanol-dichloromethane) and recrystallization (ethyl acetate-diethyl ether-petroleum ether) afforded the title compound (0.61 g, 53%), m.p. 153°–154° C.

Example 10

5,11-Dihydro-11-ethyl-8-[2-hydroxy-2-(4-pyridyl)ethyl]-5-methyl-6H-dipyrido[3,2-b:2',3'-e][1,4]diazepin-6-one By procedures analogous to those described in Examples 8 and 9, the title compound (12 mg), m.p. 96° C. (dec), was prepared from 5,11-dihydro-11-ethyl-5-methyl-8-[2-(4-pyridyl)ethyl]-6H-dipyrido[3,2-b:2',3'-e][1,4]diazepin-6-one

Example 11

2-Chloro-5,11-dihydro-11-ethyl-8-[2-fluoro-2-(4-pyridyl)ethyl]-5-methyl-6H-dipyrido-[3,2-b:2',3'-e][1,4]diazepin-6-one The product of Example 9b (60 mg, 0.15 mmol) was dissolved in 5 mL of dichloromethane. The resultant solution was cooled to −65° C. under argon, and diethylaminosulfur trifluoride (19 µL, 0.14 mmol) was added. After 1 hour, the reaction mixture was diluted with water. The product was extracted with dichloromethane, washed with saturated aq. sodium bicarbonate and saturated aq. sodium chloride, dried (magnesium sulfate), and concentrated. Purification by flash chromatography (elution with methanol-dichloromethane) and recrystallization (ethyl acetate-hexanes) afforded the title compound (12 mg, 19%), m.p. 180° C.

Example 12

2-Chloro-5,11-dihydro-11-ethyl-8-[2-oxo-2-(4-pyridyl)ethyl]-5-methyl-6H-dipyrido[3,2-b:2',3'-e][1,4]diazepin-6-one The product of Example 9b (0.16 g, 0.39 mmol) was dissolved in 5 mL of dichloromethane at room temperature under argon, and Dess-Martin periodinane (0.19 g, 0.45 mmol) was added. After 2 hours, the reaction mixture was diluted with water. The product was extracted with dichloromethane, washed with saturated aq. sodium bicarbonate and saturated aq. sodium chloride, dried (magnesium sulfate), and concentrated. Purification by flash chromatography (elution with methanol-dichloromethane) and recrystallization (ethyl acetate-hexanes) afforded the title compound (13 mg, 8%), m.p. 154° C.

Example 13

2-Chloro-5,11-dihydro-11-ethyl-8-[2-hydroxy-2-(N-oxo-pyrid-4-yl)ethyl]-5-methyl-6H-dipyrido[3,2-b:2',3'-e][1,4]diazepin-6-one By a procedure analogous to that described in Example 8, the title compound (37 mg, 70%) was prepared by oxidation of the product of Example 9b (50 mg, 0.12 mmol) with m-chloroperbenzoic acid (55%, 0.18 g, 0.57 mmol). Following recrystallization (ethanol-hexanes), the product was obtained as white crystals, m.p. 242°–243° C. (dec).

Example 14

2,8-Bis[2-(pyrid-4-yl)ethyl]-5,11-dihydro-11-ethyl-5-methyl-6H-dipyrido[3,2-b:2',3'-e][1,4]diazepin-6-one By a procedure analogous to that described in Example 3b, 13 mg of the title compound was prepared from 40 mg of 2,8-bis[2-(4-pyridyl)ethen-1-yl]-5,11-dihydro-11-ethyl-5-methyl-6H-dipyrido[3,2-b:2',3'-e][1,4]diazepin-6-one (obtained as a byproduct from the reaction described in Example 3a). The product was obtained as a yellow oil.

Example 15

2-Chloro-5,11-dihydro-11-ethyl-8-[2-(pyrid-4-yl)ethyl]-6H-dipyrido[3,2-b:2',3'-e][1,4]diazepin-6-one To a mixture of 2-chloro-5,11-dihydro-11-ethyl-8-[trans-2-pyridyl)ethen-1-yl]-6-H-dipyrido[3,2-b:2',3'-e][1,4]diazepin-6-one (obtained from 2-chloro-5,11-dihydro-11-ethyl-8-iodo-6H-dipyrido[3,2-b:2',3'-e][1,4]diazepin-6-one by a procedure analogous to that described in Example 1h) (0.11 g, 0.28 mmol) and 10% palladium on carbon (40 mg) in 2 mL of tetrahydrofuran was added a solution of sodium hypophosphite (33 mg, 0.31 mmol) in 1 mL of water. The reaction mixture was heated in a sealed tube at 80°–85° C. overnight. Workup and purification as described for Example 3b provided 6 mg of the title compound, m.p. 194°–196° C. (chloroform/petroleum ether).

Example 16

2-Chloro-5,11-dihydro-11-ethyl-5-methyl-8-[2-(2-naphthyl)ethyl]-6H-dipyrido[3,2-b:2',3'-e][1,4]diazepin-6-one

Example 17

5,11-Dihydro-11-ethyl-5-methyl-8-[2-(2-naphthyl)ethyl]-6H-dipyrido[3,2-b:2',3'-e][1,4]diazepin-6-one By a procedure analogous to that described in Example 1h, 2-chloro-5,11-dihydro-11-ethyl-8-iodo-5-methyl-6H-dipyrido[3,2-b:2',3'-e][1,4]diazepin-6-one was coupled with 2-vinylnaphthalene in the presence of bis (triphenylphosphine)palladium(II) chloride and triethylamine. The product was hydrogenated as described in Example 15 to give 16 mg of the compound of Example 16, m.p. 115°–117° C. (ether/hexanes), and 32 mg of the compound of Example 17, m.p. 136°–137° C. (ethyl acetate/hexanes).

Example 18

5,11-Dihydro-11-ethyl-8-[2-(3-fluorophenyl)ethyl]-5methyl-6H-dipyrido[3,2-b:2',3'-e][1,4]diazepin-6-one a) 2-Chloro-5,11-dihydro-11-ethyl-8-[2-(3-fluorophenyl)ethen-1-yl]-5-methyl-6H-dipyrido[3,2-b:2',3'-e][1,4]diazepin-6-one By a procedure analogous to that described in Example 1h, 2-chloro-5,11-dihydro-11-ethyl-8-iodo-5-methyl-6H-dipyrido[3,2-b:2',3'-e][1,4]diazepin-6-one was coupled with 3-fluorostyrene in the presence of bis(triphenylphosphine) palladium(II) chloride and triethylamine. The product was hydrogenated by a procedure analogous to that described in Example 15 to give 16 mg of the title compound, m.p. 130°–131° C. (ethyl acetate/hexanes).

Example 19

5,11-Dihydro-11-ethyl-5-methyl-8-[2-(3-tolyl)ethyl]-6H-dipyrido[3,2-b:2',3'-e][1,4]diazepin-6-one a) 5,11-Dihydro-11-ethyl-5-methyl-8-[2-(3-tolyl)ethen-1-yl]-6H-dipyrido[3,2-b:2',3'-e][1,4]diazepin-6-one A mixture of 5,11-dihydro-11-ethyl-8-iodo-5-methyl-6H-dipyrido[3,2-b:2',3'-e][1,4]diazepin-6-one (0.15 g, 0.4 mmol), 3-methylstyrene (0.05 mL, 0.4 mmol), palladium acetate (29 mg, 0.13 mmol), sodium bicarbonate (83 mg, 1.0 mmol), tetrabutylammonium chloride (0.11 g, 0.47 mmol), and 1 crystal of BHT in 2 mL of N,N-dimethylformamide was heated at 90° C. under argon for 4.5 hours. The reaction mixture was diluted with water and extracted with ethyl acetate. The organic layer was washed with saturated aqueous sodium chloride, dried (magnesium sulfate), and concentrated. Purification by flash chromatography, eluting with ethyl acetate/hexanes, afforded 0.13 g of the title compound, m.p. 207°–208° C. (ethyl acetate/hexanes).

b) 5,11-Dihydro-11-ethyl-5-methyl-8-[2-(3-tolyl)ethyl]-6H-dipyrido[3,2-b:2',3'-e][1,4]diazepin-6-one Hydrogenation of 5,11-dihydro-11-ethyl-5-methyl-8-[trans-2-(3-tolyl)ethen-1-yl]-6H -dipyrido[3,2-b:2',3'-e][1,4]diazepin-6-one (0.13 g, 0.35 mmol), by a procedure analogous to that described in Example 15, afforded 0.08 g of the title compound as white crystals, m.p. 103°–104° C. (ethyl acetate/ether/petroleum ether).

Example 20

5,11-Dihydro-11-ethyl-5-methyl-8-[2-(3-mathyloxadiazol-5-yl)ethyl]-6H-dipyrido[3,2-b:2',3'-e][1,4]diazepin-6-one a) 8-(trans-2-Carboethoxyethen-1-yl)-2-chloro-5,11-dihydro-11-ethyl-5-methyl-6H-dipyrido[3,2-b:2',3'-e][1,4] diazepin-6-one 2-Chloro-5,11-dihydro-11-ethyl-8-iodo-5-methyl-6H-dipyrido[3,2-b:2',3'-e][1,4]diazepin-6-one (0.6 g, 1.45 mmol) was coupled with ethyl acrylate (0.19 mL, 1.75 mmol) by a procedure analogous to that described in Example 1h to give 0.42 g of the title compound as beige crystals, m.p. 192°–193° C. (ethyl acetate/hexanes). Hydrogenation, as described in Example 15, gave 0.22 g of a mixture of reduction products, which was used directly in the next step.

b) 5,11-Dihydro-11-ethyl-5-methyl-8-[2-(3-methyloxadiazol-5-yl)ethyl]-6H-dipyrido[3,2-b:2',3'-e][1,4]diazepin-6-one To a suspension of sodium hydride (50% oil dispersion, 81 mg, 1.7 mmol) in tetrahydrofuran (10 mL) was added N-hydroxyacetimidine (55 mg, 0.74 mmol). After 5 min, a solution of the ester mixture in 5 mL of tetrahydrofuran was added, and the reaction mixture was heated to reflux. After 4.5 hours, the reaction mixture was poured onto ice. Extraction with ethyl acetate and purification of the crude product by flash chromatography, eluting with ethyl acetate/hexanes, afforded 28 mg of the title compound, m.p. 40° C. (ethyl acetate/hexanes).

Example 21

8-[2-(3Aminophenyl)ethyl]-5,11-dihydro-11-ethyl-5-methyl-6H-dipyrido[3,2-b:2',3'-e][1,4]diazepin-6-one a) 5,11-Dihydro-11-ethyl-5-methyl-8-[2-(3-nitrophenyl)ethen-1-yl]-6H-dipyrido[3,2b:-2',3'-1,4]diazepin-6-one The coupling reaction of 5,11-dihydro-11-ethyl-8-iodo-5-methyl-6H-dipyrido[3,2-b:2',3'-e][1,4]diazepin-6-one (0.1 g, 0.26 mmol) with 3-nitrostyrene, as described in Example 1h, afforded 0.07 g of the title compound as a yellow powder.

b) 8-[2-(3-Aminophenyl)ethyl]-5,11-dihydro-11-ethyl-5-methyl-6H-dipyrido[3,2-b:2',3'-e][1,4]diazepin-6-one Hydrogenation of 5,11-dihydro-11-ethyl-5-methyl-8-[2-(3-nitrophenyl)ethen-1-yl]-6H-dipyrido[3,2-b:2',3'-e][1,4] diazepin-6-one (0.07 g, 0.17 mmol), by a procedure analogous to that described in Example 15, afforded 49 mg of the title compound, m.p. 129°–131° C. (ethyl acetate/hexanes).

Example 22

8-[2-(3-Aminophenyl)ethyl]-2-chloro-5,11-dihydro-11-ethyl-5-methyl-6H-dipyrido[3,2-b:2',3'-e][1,4] diazepin-6-one a) 3-Amino-2,6-dichloropyridine By a procedure analogous to that described in Example 1b, 55.7 g of the title compound was prepared from 70 g of 2,6-dichloro-3-nitropyridine.

b) N-(2,6-Dichloro-3-pyridinyl)-2-chloro-3-pyridinecarboxamide

By a procedure analogous to that described in Example 1c, 92 g of the title compound was prepared by condensing 55.7 g of 3-amino-2,6-dichloropyridine with 2-chloronicotinoyl chloride (from 54 g of 2-chloronicotinic acid).

c) N-(2,6-Dichloro-3-pyridinyl)-2-ethylamino-3-pyridinecarboxamide

A mixture of N-(2,6-dichloro-3-pyridinyl)-2-chloro-3-pyridinecarboxamide (12.0 g, 39.8 mmol), ethylamine (3.6 g, 80.7 mmol), and 30 mL of xylenes in a sealed vessel was heated at 165° C. for 6 hours. The reaction mixture was cooled to room temperature and extracted with ethyl acetate to give 7.4 g of the title compound, suitable for use in the next reaction.

d) N-(2,6-Dichloro-3-pyridinyl)-5-bromo-2-ethylamino-3-pyridinecarboxamide

To a solution of N-(2,6-dichloro-3-pyridinyl)-2-ethylamino-3-pyridinecarboxamide (7.4 g, 24 mmol) and potassium acetate (2.8 g, 28 mmol) in 90 mL of acetic acid was added bromine (1.2 mL, 23 mmol). After 15 min, the reaction mixture was diluted with water and the precipitate was collected by suction filtration to give 8.2 g of the title compound, suitable for use in the next reaction.

e) 8-Bromo-2-chloro-5,11-dihydro-11-ethyl-6H-dipyrido[3,2-b:2',3'-e][1,4]diazepin-6-one To a solution of N-(2,6-dichloro-3-pyridinyl)-5-bromo-2-ethylamino-3-pyridinecarboxamide (5.9 g, 15 mmol) in 30 mL of pyridine at 50° C. under argon was added by syringe a 1.0M solution of sodium hexamethyldisilazide in tetrahydrofuran (31.5 mL, 31.5 mmol). After 10 min, the reaction mixture was diluted with ice water and allowed to stir for 2 hours. The resultant orange-yellow precipitate was collected by suction filtration and air-dried to give 4.9 g of the title compound.

f) 8-Bromo-2-chloro-5,11-dihydro-11-ethyl-5-methyl-6H-dipyrido[3,2-b:2',3'-e][1,4]-diazepin-6-one By a procedure analogous to that described in Example 1e, 4.5 g of the title compound was prepared from 4.9 g of 8-bromo-2-chloro-5,11-dihydro-11-ethyl-6H-dipyrido[3,2-b:2',3'-e][1,4]-diazepin-6-one. g) 2-Chloro-5,11-dihydro-11- ethyl-5-methyl-8-[trans-2-(3-nitrophenyl)ethen-1-yl]-6H-dipyrido[3,2-b:2',3'-e][1,4]diazepin-6-one By a procedure analogous to that described in Example 1h, 0.97 g of the title compound was prepared by coupling 1.0 g of 8-bromo-2-chloro-5,11-dihydro-11-ethyl-5-methyl-6H-dipyrido[3,2-b:2',3'-e][1,4]diazepin-6-one with 3-nitrostyrene in the presence of bis(triphenylphosphine)palladium(II) chloride and N,N-diisopropylethylamine.

h) 8-[2-(3-Aminophenyl)ethyl]-2-chloro-5,11-dihydro-11-ethyl-5-methyl-6H-dipyrido[3,2-b:2',3'-e][1,4]diazepin-6-one By a procedure analogous to that described in Example 3b, 0.42 g of the title compound was prepared from 0.51 g of 2-chloro-5,11-dihydro-11-ethyl-5-methyl-8-[trans-2-(3-nitrophenyl)ethen-1-yl]-6H-dipyrido[3,2-b:2',3'-e][1,4]diazepin-6-one. The compound crystallized from ethanol/petroleum ether, m.p. 121°–123° C.

Example 23

8-[2-(3-Azidophenyl)ethyl]-2chloro-5,11-dihydro-11ethyl-5methyl-6H-dipyrido[3,2-b:2',3'-e][1,4]diazepin-6-one 8-[2-(3-Aminophenyl)ethyl]-2-chloro-5,11-dihydro-11-ethyl-5-methyl-6H-dipyrido[3,2-b:2',3'-e][1,4]diazepin-6-one (0.22 g, 0.54 mmol) was dissolved in 0.55 mL of concentrated hydrochloric acid. Water (2.8 mL) was added and the solution was cooled to 0° C. producing a precipitate. A solution of sodium nitrite (0.19 g, 2.75 mmol) in 8 mL of water was added dropwise. After 20 min, a solution of sodium azide (0.27 g, 4.15 mmol) in 3 mL of water was added in the dark. After 15 min, the product was extracted with ethyl acetate. Purification by flash chromatography, eluting with ethyl acetate/hexanes, and recrystallization (ether/petroleum ether) afforded 0.17 g of the title compound, m.p. 104°–105° C.

Example 24

2-Chloro-5,11-dihydro-11-ethyl-8-[2-(3-iodophenyl)ethyl]-5methyl-6H-dipyrido[3,2-b:2',3'-e][1,4]diazepin-6-one In a manner analogous to the procedure described for Example 23, 8-[2-(3-aminophenyl)ethyl]-2-chloro-5,11-dihydro-11-ethyl-5-methyl-6H-dipyrido[3,2-b:2',3'-e][1,4]diazepin-6-one (0.15 g, 0.37 mmol) was diazotized and treated with sodium iodide to provide 9 mg of the pure product, m.p. 143°–145° C. (petroleum ether).

Example 25

2-Chloro-5,11-dihydro-11-ethyl-8-[2-(3-methylsulfonamidophenyl)ethyl]-6H-dipyrido[3,2-b:2',3'-e][1,4]diazepin-6-one By a procedure analogous to that described in Example 35, 15 mg of the title compound was prepared by reaction of 8-[2-(3-aminophenyl)ethyl]-2-chloro-5,11-dihydro-11-ethyl-5-methyl-6H-dipyrido[3,2-b:2',3'-e][1,4]diazepin-6-one with methanesulfonyl chloride. The product crystallized from ethyl acetate/hexanes, m.p. 131°–132° C.

Example 26

2Chloro-5,11-dihydro-11-ethyl-5-methyl-8-2-[(3-ureidophenyl)ethyl]-6H-dipyrido[3,2-b:2',3'-e][1,4]diazepin-6-one To an aqueous solution of potassium cyanate (27 mg, 0.33 mmol) was added dropwise a solution of 8-[2-(3-aminophenyl)ethyl]-2-chloro-5,11-dihydro-11-ethyl-5-methyl-6H-dipyrido[3,2-b:2',3'-e][1,4]diazepin-6-one (68 mg, 0.17 mmol) in a mixture of acetic acid and water. After 5 hours, the reaction mixture was diluted with ethyl acetate. The organic layer was washed with saturated aq. sodium bicarbonate and saturated aq. sodium chloride, dried (magnesium sulfate), and concentrated. Purification by flash chromatography (elution with methanol-dichloromethane) and recrystallization (ethyl acetate-petroleum ether) afforded the title compound (31 mg, 41%), m.p. 121°–123° C.

Example 27

2-Chloro-5,11-dihydro-11-ethyl-5-methyl-8-[2-(3-methylthio-4-indolyl)ethyl]-6H-dipyrido[3,2-b:2',3'-e][1,4]diazepin-6-one; and

Example 28

2-Chloro-5,11-dihydro-11-ethyl-5-methyl-8-[2-(3-methylthio-6-indolyl)ethyl]-6H-dipyrido[3,2-b:2',3'-e][1,4]diazepin-6-one to a solution of 8-[2-(3-aminophenyl)ethyl]-2-chloro-5,11-dihydro-11-ethyl-5-methyl-6H-dipyrido[3,2-b:2',3'-e][1,4]diazepin-6-one (0.40 g, 0.98 mmol) in 6 mL of dichloromethane at −25° C. under argon was added N-chlorosuccinimide (0.14 g, 1.0 mmol). After 15 min, methylthioacetaldehyde dimethyl acetal (0.13 mL, 0.98 mmol) was added. The reaction mixture was stoppered and placed in the freezer (−15° C.) overnight. Additional N-chlorosuccinimide (54 mg, 0.4 mmol) was added. After 6 hours, Et₃N (0.15 mL, 1.0 mmol) was added, and the reaction mixture was allowed to warm to room temperature. The reaction mixture was diluted with water and the product was extracted with dichloromethane. The brown oil obtained upon concentration was dissolved in 12 mL of toluene. Et₃N (0.15 mL, 1.0 mmol) was added, and the reaction mixture was heated at reflux for 12 h under argon. Solvents were removed, and the residue was dissolved in 10 mL of methanol. 2N hydrochloric acid (1.2 mL) was added, and the mixture was heated at reflux for 2 hours. The reaction mixture was diluted with water and the product was extracted with ethyl acetate. Purification by flash chromatography (elution with ethyl acetate-dichloromethane) and crystallization (diethyl ether-petroleum ether) afforded 11 mg of the product of Example 27, m.p. 228°–229° C., and 19 mg of the product of Example 28, m.p. 209°–210° C.

Example 29

5,11-Dihydro-11-ethyl-5methyl-8-[2-(4-indolyl)ethyl]-6H-dipyrido[3,2-b:2',3'-e][1,4]diazepin-6-one; and

Example 30

2-Chloro-5,11-dihydro-11-ethyl-5methyl-8-[2-(4-indolyl)ethyl]-6H-dipyrido[3,2-b:2',3'-e][1,4]diazepin-6-one Raney nickel was added to a solution of the product of Example 27 (71 mg, 0.15 mmol) in absolute ethanol (4 mL). The reaction mixture was heated at 100° C. under argon for 44 hours. The reaction mixture was filtered through Celite and concentrated. Purification by flash chromatography (elution with ethyl acetate-hexanes), followed by preparative TLC (elution with ethyl acetate-hexanes), and recrystallization (diethyl ether-petroleum ether) afforded 22 mg of the product of Example 29, m.p. 186°–188° C., and 9 mg of the product of Example 30, m.p. 196°–198° C.

Example 31

5,11-Dihydro-11-ethyl-5methyl-8-[2-(6-indolyl) ethyl]-6H-dipyrido[3,2-b:2',3'-e][1,4]diazepin-6-one

Example 32

2-Chloro-5,11-dihydro-11-ethyl-5methyl-8-[2-(6-indolyl)ethyl]-6H-dipyrido[3,2-b:2',3'-e][1,4]diazepin-6-one As described in Examples 29 and 30, 100 mg (0.21 mmol) of the product from Example 28 was treated with Raney nickel. Purification by flash chromatography (elution with ethyl acetate-hexanes), radial chromatography (elution with ethyl acetate-hexanes), and recrystallization provided 4 mg of the product of Example 31, m.p. 164–°166° C. (diethyl ether-petroleum ether), and 3 mg of the product of Example 32, m.p. 92° C. (dec) (ethyl acetate-petroleum ether).

Example 33

8-[2-(4-Aminophenyl)ethyl]-2-chloro-5,11-dihydro-11-ethyl-5-methyl-6H-dipyrido[3,2-b:2',3'-e][1,4]diazepin-6-one; and

Example 34

8-[2-(4-Aminophenyl)ethyl]-5,11-dihydro-11-ethyl-5methyl-6H-dipyrido[3,2-b:2',3'-e][1,4]diazepin-6-one To a mixture of 8-[2-(4-nitrophenyl)ethen-1-yl]-2-chloro-5,11-dihydro-11-ethyl-5-6H-dipyrido[3,2-b:2',3'-e][1,4]diazepin-6-one (obtained from 8-bromo-2-chloro-5,11-dihydro-11-ethyl-5-methyl-6H-dipyrido[3,2-b:2',3'-e][1,4]diazepin-6-one by a procedure analogous to that described in Example 22g) and 10% palladium on carbon (40 mg) in 4 mL of tetrahydrofuran was added a solution of sodium hypophosphite (0.15 g, 1.4 mmol) in 2 mL of water. The reaction mixture was heated in a sealed tube at 70° C. overnight. Workup and purification as described for Example 3b provided 67 mg of the compound of Example 33, m.p. 191°–192° C. (ethanol/hexanes), and 53 mg of the compound of Example 34, m.p. 157°–158° C. (ethanol/hexanes).

Example 35

2Chloro-5,11-dihydro-11-ethyl-5-methyl-8-[2-(4-methylsulfonamidophenyl)ethyl]-6H-dipyrido[3,2-b:2',3'-e][1,4]diazepin-6-one To a solution of 8-[2-(4-aminophenyl)ethyl]-2-chloro-5,11-dihydro-11-ethyl-5-methyl-6H-dipyrido[3,2-b:2',3'-e][1,4]diazepin-6-one (16 mg, 0.04 mmol) and 6 μL of pyridine in dichloromethane at 0° C. was added 5 μL of methanesulfonyl chloride. The reaction mixture was allowed to stir at room temperature overnight. The orange reaction mixture was then concentrated to dryness and the product was purified by flash chromatography, eluting with methanol/dichloromethane, and recrystallization from ethanol/hexanes to give 6 mg of the title compound, m.p. 199°–204° C.

Example 36

2Chloro-5,11-dihydro-11-ethyl-5-methyl-8-[2-(4-dimethylsulfonamidophenyl)ethyl]-6H-dipyrido[3,2-b:2',3'-e][1,4]diazepin-6-one In a manner analogous to that described in Example 35, 11 mg of the title compound, m.p. 196°–198° C. (ethyl acetate/hexanes), was prepared from 16 mg of 8-[2-(4-aminophenyl)ethyl]-2-chloro-5,11-dihydro-11-ethyl-5-methyl-6H-dipyrido[3,2-b:2',3'-e][1,4]diazepin-6-one and 10 μL of methanesulfonyl chloride.

Example 37

2Chloro-11-cyclopropyl-5,11-dihydro-5-methyl-8-[2-(pyrid-4-yl)ethyl]-6H-dipyrido[3,2-b:2',3'-e][1,4]diazepin-6-one By procedures analogous to those described in Example 3, 30 mg of the title compound, m.p. 218°–219° C. (ethyl acetate-hexanes), was prepared from 8-bromo-2-chloro-5,11-dihydro-11-ethyl-5-methyl-6H-dipyrido[3,2-b:2',3'-e][1,4]diazepin-6-one (prepared by procedures analogous to those described in Example 22a–f).

Example 38

5,11-Dihydro-11-ethyl-2-fluoro-5-methyl-8-[2-(pyrid-4-yl)ethyl]-6H-dipyrido[3,2-b:2',3'-e][1,4]diazepin-6-one a) 8-bromo-2-fluoro-5,11-dihydro-11-ethyl-5-methyl-6H-dipyrido[3,2-b:2',3'-e][1,4]diazepin-6-one A plastic centrifuge tube was charged with 2-amino-8-bromo-5,11-dihydro-11-ethyl-5-methyl-6H-dipyrido[3,2-b:2',3'-e][1,4]diazepin-6-one (prepared from 8-bromo-2-chloro-5,11-dihydro-11-ethyl-5-methyl-6H-dipyrido[3,2-b:2',3'-e][1,4]diazepin-6-one by procedures analogous to those described in Example 5; 0.10 g, 0.3 mmol) and flushed with argon. HF-pyridine (2 mL) was added, and the resultant yellow-brown suspension was cooled in an ice-bath. Sodium nitrite (29 mg, 0.42 mmol) was added in several portions over 10 min to produce a purple solution. The tube was capped, and the reaction mixture was allowed to stir at room temperature overnight. The reaction mixture was poured into ice-6N sodium hydroxide, and the product was extracted with ethyl acetate. Purification by flash chromatography (elution with ethyl acetate-hexanes) afforded the title compound (99 mg, 98%) as white crystals, m.p. 154°–156° C.

b) 5,11-Dihydro-11-ethyl-2-fluoro-8-[2-(pyrid-4-yl)ethyl]-5-methyl-6H-dipyrido[3,2-b:2',3'-e][1,4]diazepin-6-one 8-Bromo-2-fluoro-5,11-dihydro-11-ethyl-5-methyl-6H-dipyrido[3,2-b:2',3'-e][1,4]diazepin-6-one (70 mg, 0.2 mmol) was coupled with 4-vinylpyridine in the presence of bis(triphenylphosphine)palladium(II) chloride and (i-Pr)$_2$NEt as described in example 1h. The product was hydrogenated as described in example 3b. Purification by flash chromatography (elution with methanol-dichloromethane) and recrystallization (diethyl ether-petroleum ether) afforded 26 mg of the title compound as white crystals, m.p. 109°–111° C.

Example 39

5,11-Dihydro-11-ethyl-2-fluoro-8-[2-(N-oxo-pyrid-4-yl)ethyl]-5-methyl-6H-dipyrido[3,2-b:2',3'-e][1,4]diazepin-6-one By a procedure analogous to that described in Example 8, the title compound (55 mg, 82%) was prepared by oxidation of the product of Example 38 (65 mg, 0.17 mmol) with m-chloroperbenzoic acid (50%, 70 mg, 0.20 mmol). Following recrystallization (ethyl acetate-hexanes), the product was obtained as white crystals, m.p. 173°–174° C.

Example 40

5,11-Dihydro-11-ethyl-2-fluoro-8-[2-hydroxy-2-(pyrid-4-yl)ethyl]-5-methyl-6H-dipyrido[3,2-b:2',3'-e][1,4]diazepin-6-one By procedures analogous to those described in Example 9, the title compound (26 mg, 58%) was prepared from the product of Example 39 (45 mg, 0.12 mmol). Following recrystallization (ethyl acetate-hexanes), the product was obtained as white crystals, m.p. 174°–176° C.

Example 41

5,11-Dihydro-11-ethyl-2-fluoro-5-methyl-8-[2-(2-naphthyl)ethyl]-6H-dipyrido[3,2-b:2',3'-e][1,4]diazepin-6-one 8-Bromo-2-fluoro-5,11-dihydro-11-ethyl-5-methyl-6H-dipyrido[3,2-b:2',3'-e][1,4]diazepin-6-one (35 mg, 0.10 mmol) was coupled with 2-vinylnaphthalene in the presence of bis(triphenylphosphine)palladium(II) chloride and (i-Pr)$_2$NEt as described in example 1h. The product was hydrogenated as described in example 3b. Purification by flash chromatography (elution with ethyl acetate-hexanes) and recrystallization (diethyl ether-hexanes) afforded 20 mg of the title compound as white crystals, m.p. 112°–114° C.

Examples illustrating synthetic Method B

Example 42

5,11-Dihydro-11-ethyl-5methyl-8-(2-phenylethyl)-6H-dipyrido[3,2-b:2',3'-e][1,4]diazepin-6-one a) 5,11-Dihydro-11-ethyl-5-methyl-8-phenylethynyl-6H-dipyrido[3,2-b:2',3'-e][1,4]diazepin-6-one A mixture of 5,11-dihydro-11-ethyl-8-iodo-5-methyl-6H-dipyrido[3,2-b:2',3'-e][1,4]diazepin-6-one (0.20 g, 0.53 mmol), phenylacetylene (0.06 mL, 0.55 mmol), bis(triphenylphosphine)palladium(II) chloride (25 mg, 0.04 mmol), and triethylamine (0.16 mL, 1.14 mmol) in 3 mL of N,N-dimethylformamide was heated at 95° C. under argon for 19 hours. Workup as described in Example 1h and purification by flash chromatography, eluting with ethyl acetate/dichloromethane, afforded 0.1 g of the title compound.

b) 5,11-Dihydro-11-ethyl-5-methyl-8-(2-phenethyl)-6H-dipyrido[3,2-b:2',3'-e][1,4]diazepin-6-one 5,11-Dihydro-11-ethyl-5-methyl-8-(2-phenylethen-1-yl)-6H-dipyrido[3,2-b:2',3'-e][1,4]diazepin-6-one (70 mg, 0.2 mmol) was hydrogenated over platinum oxide in ethyl acetate under 50 p.s.i. of hydrogen. The reaction mixture was filtered through Celite and concentrated. Purification by flash chromatography and preparative TLC, eluting with ethyl acetate/dichloromethane, afforded 31 mg of the title compound as yellow crystals, m.p. 129°–131° C.

Example 43

5,11-Dihydro-11-ethyl-5-methyl-8-(cis-2-phenylethen-1-yl)-6H-dipyrido[3,2-b:2',3'-e][1,4]diazepin-6-one 5,11-Dihydro-11-ethyl-5-methyl-8-phenylethynyl-6H-dipyrido[3,2-b:2',3'-e][1,4]diazepin-6-one (0.12 g, 0.34 mmol) was hydrogenated over Lindlar catalyst in ethanol under 50 p.s.i. of hydrogen. Workup and purification as described in Example 42 afforded 20 mg of the title compound as a yellow-orange oil.

Example 44

5,11-Dihydro-11-ethyl-5-methyl-8-[2-(pyrid-2-yl)ethyl]-6H-dipyrido[3,2-b:2',3'-e][1,4]diazepin-6-one 5,11-Dihydro-11-ethyl-5-methyl-8-(pyrid-2-yl)ethynyl-6H-dipyrido[3,2-b:2',3'-e][1,4]diazepin-6-one (0.15 g) was prepared by coupling 5,11-dihydro-11-ethyl-8-iodo-5-methyl-6H-dipyrido[3,2-b:2',3'-e][1,4]diazepin-6-one with 2-ethynylpyridine by a procedure analogous to that described in Example 42a. Hydrogenation as described in Example 42b afforded 24 mg of the title compound, m.p. 70°–72° C. (ethyl acetate/hexanes).

Example 45

2Chloro-5,11-dihydro-11-ethyl-5-methyl-8-(2-phenylethyl)-6H-dipyrido[3,2-b:2',3'-e][1,4]diazepin-6-one 2-Chloro-5,11-dihydro-11-ethyl-5-methyl-8-phenylethynyl-6H-dipyrido[3,2-b:2',3'-e][1,4]diazepin-6-one (0.33 g) was prepared from 2-chloro-5,11-dihydro-11-ethyl-8-iodo-5-methyl-6H-dipyrido[3,2-b:2',3'-e][1,4]diazepin-6-one and phenylacetylene by a procedure analogous to that described in Example 42a. Hydrogenation as described in Example 42b afforded 0.18 g of the title compound as white needles, m.p. 128°–129.5° C.

Example 46

2Chloro-5,11-dihydro-11-ethyl-5-methyl-8-(2-phenyloxiranyl)-6H-dipyrido[3,2-b:2',3'-e][1,4]diazepin-6-one 2-Chloro-5,11-dihydro-11-ethyl-5-methyl-8-(cis-2-phenylethen-1-yl)-6H-dipyrido[3,2-b:2',3'-e][1,4]diazepin-6-one (prepared by procedures analogous to those described in Example 43) (51 mg, 0.13 mmol) was dissolved in 3 mL of dichloromethane and treated with m-chloroperbenzoic acid (50%, 45 mg, 0.13 mmol) at room temperature. Solid Ca(OH)$_2$ was added, and the reaction mixture was filtered and concentrated. Purification by flash chromatography (elution with ethyl acetate-hexanes) and recrystallization (diethyl ether-hexanes) afforded the title compound (11 mg, 21%), m.p. 105°–107° C.

Example 47

5,11-Dihydro-11-ethyl-5-methyl-8-(2-phenylethyl)-2-(2-pyrrolyl)-6H-dipyrido[3,2-b:2',3'-e][1,4]diazepin-6-one A mixture containing 2-chloro-5,11-dihydro-11-ethyl-5-methyl-8-(2-phenylethyl)-6H-dipyrido[3,2-b:2',3'-e][1,4]diazepin-6-one (0.10 g, 0.26 mmol), potassium acetate (0.05 g, 0.51 mmol), N-(tert-butyloxycarbonyl)pyrrole (0.078 g, 0.47 mmol), and tetrakis(triphenylphosphine)palladium(0) (20 mg, 0.02 mmol) in 2 mL of N,N-dimethylformamide was heated in a sealed tube at 125° C. for 10 hours. Additional potassium acetate (50 mg), N-(tert-butyloxycarbonyl)pyrrole (0.08 g), and tetrakis(triphenylphosphine)palladium(0) (15 mg) were added, and the reaction mixture was heated at 140° C. for an additional 8 hours. The reaction mixture was diluted with water and extracted with ethyl acetate. The organic layer was washed with saturated aqueous sodium chloride, dried over magnesium sulfate, and concentrated. Purification by flash chromatography, eluting with ethyl acetate/hexanes, provided 20 mg of the title compound, as a foam.

Example 48

5,11-Dihydro-11-ethyl-5-methyl-8-phenylethynyl-6H-dipyrido[3,2-b:2',3'-e][1,4]diazepin-6-one To a solution of 8-bromo-5,11-dihydro-3,4-dimethyl-11-ethyl-5-methyl-6H-dipyrido[3,2-b:2',3'-e][1,4]diazepin-6-one (0.05 g, 0.14 mmol), phenylacetylene (0.03 g, 0.28 mmol), and triethylamine (3.5 mL) in 1.5 mL of acetonitrile was added tetrakis(triphenylphosphine)palladium(0) (10 mg) and copper(I) iodide (5 mg). The resultant mixture was heated at reflux for 2 hours. The solvent was removed at reduced pressure, and the residue was purified by preparative thin layer chromatography, eluting with ethyl acetate/hexanes. The product was recrystallized from ethyl acetate/petroleum ether to provide 60 mg of the title compound, m.p. 228°–229° C.

Example 49

5,11-Dihydro-3,4-dimethyl-11-ethyl-5-methyl-8-(2-phenylethyl)-6H-dipyrido[3,2-b:2',3'-e][1,4]diazepin-6-one The title compound was prepared by hydrogenation of 5,11-dihydro-3,4-dimethyl-11-ethyl-5-methyl-8-(phenylethynyl)-6H-dipyrido[3,2-b:2',3'-e][1,4]diazepin-6-one over platinum oxide, as described in Example 42b. The product crystallized from ether/petroleum ether, m.p. 187°–188° C.

Example 50

5,11-Dihydro-11-ethyl-5-methyl-8-[2-(3-hydroxyphenyl)ethyl]-6H-dipyrido[3,2-b:2',3'-e][1,4]diazepin-6-one 5,11-Dihydro-11-ethyl-5-methyl-8-(3-hydroxyphenyl)ethynyl-6H-dipyrido[3,2-b:2',3'-e][1,4]diazepin-6-one (0.10 g) was prepared by coupling 5,11-dihydro-11-ethyl-8-iodo-5-methyl-6H-dipyrido[3,2-b:2',3'-e][1,4]diazepin-6-one with 3-hydroxyphenylacetylene by a procedure analogous to that described in Example 42a. Hydrogenation as described in Example 42b afforded 7 mg of the title compound, m.p. 177°–179° C. (ethyl acetate/ether).

Examples illustrating synthetic Method C

Example 51

5,11-Dihydro-11-ethyl-5-methyl-8-[2-(pyrid-3-yl)ethyl]-6H-dipyrido[3,2-b:2',3'-e][1,4]diazepin-6-one a) 5,11-Dihydro-11-ethyl-8-ethynyl-5-methyl-6H-dipyrido[3,2-b:2',3'-e][1,4]diazepin-6-one A mixture containing 5,11-dihydro-11-ethyl-8-iodo-5-methyl-6H-dipyrido[3,2-b:2',3'-e][1,4]diazepin-6-one (3.0 g, 7.9 mmol), trimethylsilylacetylene (1.12 mL, 7.9 mmol), bis(triphenylphosphine)palladium(II) chloride (0.46 g, 0.66 mmol), triethylamine (2.4 mL, 17 mmol), and 1–2 crystals of BHT in 15 mL of N,N-dimethylformamide was heated at 80° C. under argon for 2 hours. The reaction mixture was cooled to room temperature, diluted with water, and extracted with ethyl acetate. The organic layer was washed with saturated aqueous sodium chloride, dried over magnesium sulfate, and concentrated. Purification by flash chromatography, eluting with ethyl acetate/hexanes, provided 2.5 g of the coupled product, which was then dissolved in tetrahydrofuran (30 mL) and treated at room temperature with a 1.1M solution of tetrabutylammonium fluoride in tetrahydrofuran (14.0 mL, 15.4 mmol). After 30 min, solvent was removed at reduced pressure and the residue was purified by flash chromatography, eluting with ethyl acetate/hexanes, to give 1.4 g of the title compound as a beige solid, m.p. 117°–118° C.

b) 5,11-Dihydro-11-ethyl-5-methyl-8-(pyrid-3-yl)ethynyl-6H-dipyrido[3,2-b:2',3'-e][1,4]diazepin-6-one A mixture containing 5,11-dihydro-11-ethyl-8-ethynyl-5-methyl-6H-dipyrido[3,2-b:2',3'-e][1,4]diazepin-6-one (0.19 g, 0.68 mmol), 3-bromopyridine (0.07 mL, 0.73 mmol), tetrakis(triphenylphosphine)palladium(0), triethylamine (2 mL), and 1 crystal of BHT was heated at 85° C. in a sealed tube for 7 hours. Solvent was removed, and the residue was purified by flash chromatography, eluting with ethyl acetate/hexanes, and recrystallization from ethanol/hexanes to give 0.16 g of the title compound as yellow crystals, m.p. 178°–180° C.

c) 5,11-Dihydro-11-ethyl-5-methyl-8-(3-pyridyl)ethyl-6H-dipyrido[3,2-b:2',3'-e][1,4]diazepin-6-one Hydrogenation of 5,11-dihydro-11-ethyl-5-methyl-8-(3-pyridyl)ethynyl-6H-dipyrido[3,2-b:2',3'-e][1,4]diazepin-6-one (0.16 g, 0.45 mmol), as described in Example 42b, afforded 50 mg of the title compound, m.p. 79°–80° C. (ether/petroleum ether).

Example 52

5,11-Dihydro-11-ethyl-4-methyl-8-[cis-2-(4-pyrazolyl)ethen-1-yl]-6H-dipyrido[3,2-b:2',3'-e][1,4]diazepin-6-one; and

Example 53

5,11-Dihydro-11-ethyl-4-methyl-8-[2-(4-pyrazolyl)ethyl]-6H-dipyrido[3,2-b:2',3'-e][1,4]diazepin-6-one A mixture of 5,11-dihydro-11-ethyl-8-ethynyl-4-methyl-(-6H-dipyrido[3,2-b:2',3'-e][1,4]diazepin-6-one (obtained by procedures analogous to those described in Example 51) (147 mg), 4-iodopyrazole (199 mg), bis(triphenylphosphine)palladium(II) chloride (22 mg), copper(I) iodide (21 mg), and triethylamine (2 mL) in 4 mL of N,N-dimethylformamide was heated at 100° C. in a sealed tube for 40 min. The reaction mixture was diluted with ethyl acetate and washed with water. The organic layer was dried over sodium sulfate and concentrated. The crude residue was dissolved in 60 mL of methanol and hydrogenated at 50 p.s.i. over 10% palladium on carbon (70 mg). After 24 hours, the reaction mixture was filtered and concentrated. The residue was purified by flash chromatography, eluting with methanol/ethyl acetate, to afford the compound of Example 52, m.p. 184°–187° C. (ethyl acetate/isopropyl ether), and the compound of Example 53, m.p. 199°–201° C. (ethyl acetate/hexanes).

Example 54

5,11-Dihydro-11-ethyl-4-methyl-8-[2-(4-pyridyl)ethyl]-6H-dipyrido[3,2-b:2',3'-e][1,4]diazepin-6-one By procedures analogous to those described in Example 52, the title compound was prepared from 5,11-dihydro-11-ethyl-8-ethynyl-4-methyl-(-6H-dipyrido[3,2-b:2',3'-e][1,4]diazepin-6-one and 4-bromopyridine. The product crystallized from ethyl acetate/isopropyl ether, m.p. 176°–178° C.

Example 55

5,11-Dihydro-11-ethyl-5-methyl-8-[2-(2-thiazolyl)ethyl]-6H-dipyrido[3,2-b:2',3'-e][1,4]diazepin-6-one 5,11-Dihydro-11-ethyl-5-methyl-8-(2-thiazolyl)ethynyl-(-6H-dipyrido[3,2-b:2',3'-e][1,4]diazepin-6-one (0.15 g)

was prepared from 5,11-dihydro-11-ethyl-8-ethynyl-5-methyl-6H-dipyrido[3,2-b:2',3'-e][1,4]diazepin-6-one and 2-bromothiazole by a procedure analogous to that described in Example 51b. Hydrogenation as described in Example 42b afforded 26 mg of the title compound as an oil.

Example 56

5,11-Dihydro-11-ethyl-5-methyl-8-[2-(5-pyrimidyl) ethyl]-6H-dipyrido[3,2-b:2',3'-e][1,4]diazepin-6-one By a procedure analogous to that described in Example 51b, 5,11-dihydro-11-ethyl-8-ethynyl-5-methyl-6H-dipyrido[3,2-b:2',3'-e][1,4]diazepin-6-one (0.1 g, 0.36 mmol) was coupled with 5-bromopyrimidine (59 mg, 0.37 mmol) to give 65 mg of 5,11-Dihydro-11-ethyl-5-methyl-8-(5-pyrimidyl)ethynyl-(-6H-dipyrido[3,2-b:2',3'-e][1,4]diazepin-6-one (65 mg). A mixture containing this coupled product (65 mg), cyclohexene (0.07 mL), and 10% palladium on carbon (60 mg) in 2 mL of ethanol was heated in a sealed tube at 95° C. for 5 hours. The reaction mixture was filtered through Celite and concentrated. Purification of the residue by flash chromatography, eluting with methanol/dichloromethane, and recrystallization from ethyl acetate/hexanes provided 27 mg of the title compound, m.p. 142°–143° C.

Example 57

5,11-Dihydro-11-ethyl-5-methyl-8-[2-(4-carbomethoxyphenyl)ethyl]-6H-dipyrido[3,2-b:2',3'-e][1,4]diazepin-6-one 5,11-dihydro-11-ethyl-8-ethynyl-5-methyl-6H-dipyrido[3,2-b:2',3'-e][1,4]diazepin-6-one (0.1 g, 0.36 mmol) was coupled with methyl 4-iodobenzoate (0.1 g, 0.38 mmol) by a procedure analogous to that described in Example 51b to give 79 mg of an olefinic coupled product, 5,11-Dihydro-11-ethyl-5-methyl-8-[2-(4-methoxycarbonylphenyl)ethen-1-yl]-(-6H-dipyrido[3,2-b:2',3'-e][1,4]diazepin-6-one. Hydrogenation as described in Example 56 afforded 22 mg of the title compound, m.p. 172°–173° C. (ethyl acetate/hexanes).

Example 58

5,11-Dihydro-11-ethyl-5-methyl-8-[2-(4-tolyl)ethyl]-6H-dipyrido[3,2-b:2',3'-e][1,4]diazepin-6-one; and

Example 59

2-Chloro-5,11-dihydro-11-ethyl-5-methyl-8-[2-(4-tolyl)ethyl]-6H-dipyrido[3,2-b:2',3'-e][1,4]diazepin-6-one a) 2-Chloro-5,11-dihydro-11-ethyl-5-methyl-8-(4-tolyl)ethynyl]-6H-dipyrido[3,2-b:2',3'-e][1,4]diazepin-6-one To a solution of 2-chloro-5,11-dihydro-11-ethyl-8-ethynyl-5-methyl-6H-dipyrido[3,2-b:2',3'-e][1,4]diazepin-6-one (obtained from 8-bromo-2-chloro-5,11-dihydro-11-ethyl-5-methyl -6H -dipyrido[3,2-b:2',3'-e][1,4]diazepin-6-one by procedures analogous to those described in Example 51a) (0.2 g, 0.64 mmol), 4-iodotoluene (0.14 g, 0.64 mmol), triethylamine (0.2 mL, 1.4 mmol), and BHT (1 crystal) in N-methylpyrrolidinone was added bis(triphenylphosphine)palladium(II) chloride (44 mg), followed by copper(I) iodide (18 mg). The reaction mixture was stirred at room temperature under argon for 4.5 hours. The reaction mixture was diluted with water and extracted with ethyl acetate. The organic layer was washed with saturated aqueous sodium chloride, dried over magnesium sulfate, and concentrated. Purification by flash chromatography, eluting with ethyl acetate/hexanes, gave 0.19 g of the title compound.

b) 2-Chloro-5,11-dihydro-11-ethyl-5-methyl-8-[2-(4-tolyl)ethyl]-6H-dipyrido[3,2-b:2',3'-e][1,4]diazepin-6-one By a procedure analogous to that described in Example 34, 2-chloro-5,11-dihydro-11-ethyl-5-methyl-8-(4-tolyl) ethynyl-(-6H-dipyrido[3,2-b:2',3'-e][1,4]diazepin-6-one (0.19 g, 0.47 mmol) was hydrogenated to give 10 mg of the compound of Example 58, m.p. 120°–122° C. (ethyl acetate/hexanes), and 6 mg of the compound of Example 59, m.p. 120°–122° C. (ethyl acetate/petroleum ether).

Example 60

2-Chloro-5,11-dihydro-11-ethyl-5-methyl-8-[2-(3-tolyl)ethyl]-6H-dipyrido[3,2b:2',3'-e][1,4]diazepin-6-one The title compound, m.p. 100°–102° C. (diethyl ether/petroleum ether), was prepared from 2-chloro-5,11-dihydro-11-ethyl-8-ethynyl-5-methyl-6H-dipyrido[3,2-b:2',3'-e][1, 4]diazepin-6H -one and 3-iodotoluene by procedures analogous to those described in Example 58a–b.

Example 61

2-Chloro-5,11-dihydro-11-ethyl-5-methyl-8-[2-(2-tolyl)ethyl]-6H-dipyrido[3,2b:2',3'-e][1,4]diazepin-6-one; and

Example 62

5,11-Dihydro-11-ethyl-5-methyl-8-[2-(2-tolyl)ethyl]-6H-dipyrido[3,2-b:2',3'-e][1,4]diazepin-6-one By a procedure analogous to that described in Example 58b, 0.15 g of 2-chloro-5,11-dihydro-11-ethyl-5-methyl-8-(2-tolyl)ethynyl-(-6H-dipyrido[3,2-b:2',3'-e][1,4]diazepin-6-one (prepared from 2-chloro-5,11-dihydro-11-ethyl-8-ethynyl-5-methyl-6H-dipyrido[3,2-b:2',3'-e][1,4]diazepin-6-one and 2-iodotoluene by a procedure analogous to that described in Example 58a) was hydrogenated to give 9 mg of the compound of Example 61, m.p. 180°–182° C. (ethyl acetate/hexanes), and 15 mg of the compound of Example 62, m.p. 151°–152° C. (ethyl acetate/hexanes).

Example 63

8-[2-(2-Aminophenyl)ethyl]-2-chloro-5,11-dihydro-11-ethyl-5-methyl-6H-dipyrido[3,2-b:2',3'-e][1,4]diazepin-6-one; and

Example 64

8-[2-(2-Aminophenyl)ethyl]-5,11-dihydro-11-ethyl-5-methyl-6H-dipyrido[3,2-b:2',3'-e][1,4]diazepin-6-one By a procedure analogous to that described in Example 58b, 0.13 g of 2-chloro-5,11-dihydro-11-ethyl-5-methyl-8-(2-nitrophenyl)ethynyl-6H-dipyrido[3,2-b:2',3'-e][1,4]diazepin-6-one (prepared from 2-chloro-5,11-dihydro-11-ethyl-8-ethynyl-5-methyl-6H-dipyrido[3,2-b:2',3'-e][1,4]diazepin-6-one and 1-bromo-2-nitrobenzene by a procedure analogous to that described in Example 58a) was hydrogenated to give 6 mg of the compound of Example 63, m.p. 159°–161° C. (ethanol/hexanes), and 17 mg of the compound of Example 64, m.p. 157°–158° C. (ethanol/hexanes).

Example 65

5,11-Dihydro-11-ethyl-5-methyl-8-[2-(2-methylpyrid-4-yl)ethyl]-6H-dipyrido[3,2-b:2',3'-e][1,4]diazepin-6-onea) 4-Nitro-2-picoline To a solution of 4-nitro-2-picoline N-oxide (11 g, 71.5 mmol) in chloroform at 0° C. under argon was added a solution of $PCl_3$ (33 mL, 0.37 mmol) in chloroform. The reaction mixture was stirred at room temperature for 3 hours. The reaction mixture was poured onto ice, neutralized with ammonium hydroxide, and extracted with dichloromethane. Concentration afforded a yellow solid, which was washed with diethyl ether-petroleum ether to provide 7.8 g (79%) of the title compound, m.p. 35° C.

b) 4-Bromo-2-picoline

A mixture of 4-nitro-2-picoline (1.0 g, 7.2 mmol) and acetyl bromide (3 mL) was heated at reflux under argon for 11 hours. The reaction mixture was poured onto ice and neutralized with sodium bicarbonate. The product was extracted with ethyl acetate and purification by flash chromatography (elution with ethyl acetate-hexanes) afforded the title compound (0.62 g, 50%) as an oil.

c) 2-Chloro-5,11-dihydro-11-ethyl-5-methyl-8-[trans-2-(2-methylpyrid-4-yl)ethen-1-yl]-6H -dipyrido[3,2-b:2',3'-e][1,4]diazepin-6-one By a procedure analogous to that described in Example 51b, 48 mg (0.15 mmol) of 2-chloro-5,11-dihydro-11-ethyl-8-ethynyl-5-methyl-6H-dipyrido[3,2-b:2',3'-e][1,4]diazepin-6-one coupled with 4-bromo-2-picoline (31 mg, 0.15 mmol) to provide 51 mg (83%) of the title compound.

d) 5,11-Dihydro-11-ethyl-5-methyl-8-[2-(2-methylpyrid-4-yl)ethyl]-6H-dipyrido[3,2-b:2',3'-e][1,4]diazepin-6-one Hydrogenation of 2-chloro-5,11-dihydro-11-ethyl-5-methyl-8-[trans-2-(2-methylpyrid-4-yl) ethen-1-yl]-6H-dipyrido[3,2-b:2',3'-e][1,4]diazepin-6-one (50 mg, 0.12 mmol) at 90% afforded primarily the des-chloro title compound (12 mg, 27%), m.p. 128°–129° C. (diethyl ether-petroleum ether).

Example 66

2-Chloro-5,11-dihydro-11-ethyl-5-methyl-8-[2-(2-methylpyrid-4-yl)ethyl]-6H-dipyrido[3,2-b:2',3'-e][1,4]diazepin-6-one 2-Chloro-5,11-dihydro-11-ethyl-5-methyl-8-[trans-2-(2-methylpyrid-4-yl)ethen-1-yl]-6H -dipyrido[3,2-b:2',3'-e][1,4]diazepin-6-one (50 mg, 0.12 mmol) was hydrogenated according to the procedure described in Example 3b to afford 18 mg (37%) of the title compound, m.p. 94°–96° C. (diethyl ether-petroleum ether).

Example 67

2-Chloro-5,11-dihydro-11-ethyl-5-methyl-8-[2-(2-hydroxymethyl-4-pyridyl)ethyl]-6H -dipyrido[3,2-b:2',3'-e][1,4]diazepin-6-one a) 4-Bromo-2-picoline N-oxide 4-Nitro-2-picoline N-oxide (1.0 g, 6.5 mmol) was treated with acetyl bromide (3.5 mL, 47 mmol) as described in Example 65b to provide the title compound (0.38 g, 31%) as an orange-brown oil.

b) 2-Chloro-5,11-dihydro-11-ethyl-5-methyl-8-(N-oxo-2-methylpyrid-4-yl)ethynyl-6H-dipyrido[3,2-b:2',3'-e][1,4]diazepin-6-one 2-Chloro-5,11-dihydro-11-ethyl-8-ethynyl-5-methyl-6H-dipyrido[3,2-b:2',3'-e][1,4]diazepin-6-one (0.2 g, 0.64 mmol) was coupled with 4-bromo-2-picoline N-oxide (0.12 g, 0.64 mmol) by a procedure analogous to that described in Example 51b to provide the title compound (0.26 g, 95%).

c) 2-Chloro-5,11-dihydro-11-ethyl-5-methyl-8-(2-hydroxymethylpyrid-4-yl)ethynyl-6H-dipyrido[3,2-b:2',3'-e][1,4]diazepin-6-one The product of Example 67b (0.26 g, 0.61 mmol) was dissolved in acetic anhydride (5 mL) and heated at 105° C. in a sealed tube. After 3.5 hours, excess acetic anhydride was removed by rotary evaporation, the residue was neutralized with aq. sodium bicarbonate, and the product was extracted with ethyl acetate. The organic layer was concentrated, the residue was dissolved in 12 mL of methanol, and a solution of $K_2CO_3$ (0.18 g, 1.3 mmol) in 1 mL of water was added. After 30 min, the reaction mixture was concentrated, and the residue was diluted with dichloromethane, filtered, and concentrated. Purification by flash chromatography (elution with methanol-dichloromethane) afforded the title compound (0.07 g, 27%) as a yellow oil.

d) 2-Chloro-5,11-dihydro-11-ethyl-5-methyl-8-[2-(2-hydroxymethylpyrid-4-yl)ethyl]-6-H-dipyrido[3,2-b:2',3'-e][1,4]diazepin-6-one The product of Example 67c (66 mg, 0.16 mmol) was hydrogenated according to the procedure described in Example 3b to provide the title compound (34 mg, 50%), m.p. 133°–134.5° C. (diethyl ether-petroleum ether).

Example 68

2-Chloro-5,11-dihydro-11-ethyl-5-methyl-8-[2-(2-carbomethoxypyrid-4-yl)ethyl]-6H-dipyrido[3,2-b:2',3'-e][1,4]diazepin-6-one a) 2-Chloro-5,11-dihydro-11-ethyl-5-methyl-8-[2-(2-carboxypyrid-4-yl)ethyl]-6H-dipyrido[3,2-b:2',3'-e][1,4]diazepin-6-one By a procedure analogous to that described in Example 51b, 2-chloro-5,11-dihydro-11-ethyl-8-ethynyl-5-methyl-6H-dipyrido[3,2-b:2',3'-e][1,4]diazepin-6-one (0.83 g, 2.64 mmol) was coupled with 4-bromopicolinic acid (prepared by potassium permanganate oxidation of 4-bromo-2-picoline) (0.53 g, 2.62 mmol). The product was hydrogenated according to the procedure described in Example 3b to provide 0.4 g of the title compound as a mixture containing the corresponding des-chloro analog.

b) 2-Chloro-5,11-dihydro-11-ethyl-5-methyl-8-[2-(2-carbomethoxypyrid-4-yl)ethyl]-6H-dipyrido[3,2-b:2',3'-e][1,4]diazepin-6-one The product of Example 68a was dissolved in 50 mL of methanol containing a few drops of conc. sulfuric acid and the resultant solution was heated at reflux under argon for 15 hours. The reaction mixture was diluted with water, neutralized with sodium bicarbonate, and extracted with dichloromethane and ethyl acetate. Purification by flash chromatography, radial chromatography, and preparative TLC (elution with methanol-dichloromethane) afforded the title compound (0.20 g, 46%). A portion of this material was recrystallized (ethyl acetate-diethyl ether) to afford the pure product as off-white crystals, m.p. 149° C.

Example 69

2-Chloro-5,11-dihydro-11-ethyl-5-methyl-8-[2-(2-carboxamidopyrid-4-yl)ethyl]-6H-dipyrido[3,2-b:2',3'-e][1,4]diazepin-6-one The product of Example 68b (32 mg, 0.07 mmol) was dissolved in 5 mL of methanol and the solution was saturated with NH₃. After 6 hours, solvents were removed and the residue was purified by flash chromatography (elution with methanol-dichloromethane). Recrystallization (ethyl acetate-ethanol-hexanes) afforded the title compound (25 mg, 82%) as white crystals, m.p. 145°–147° C.

Example 70

2-Chloro-5,11-dihydro-11-ethyl-5-methyl-8-[2-(2-carboxypyrid-4-yl)ethyl]-6H-dipyrido[3,2b:2',3'-e][1,4]diazepin-6-one The product of Example 68b (0.15 g, 0.33 mmol) was dissolved in 30 mL of tetrahydrofuran, aq. lithium hydroxide (1.0M, 1.0 mL, 1.0 mmol) was added, and the reaction mixture was heated at reflux under argon. After 1 hour, additional lithium hydroxide (0.5 mL) was added and heating was continued for an additional 3 hours. The reaction mixture was concentrated, acidified with 2N hydrochloric acid, saturated with sodium chloride, and extracted with chloroform-ethanol (3: 1). Concentration afforded a yellow foam, which was recrystallized (ethanol-hexanes) to provide the title compound (58 mg, 40%) as a pale yellow solid, m.p. 118°–120° C.

Example 71

2-Chloro-5,11-dihydro-11-ethyl-5-methyl-8-[2-(2-aminopyrid-4-yl)ethyl]-6H-dipyrido[3,2-b:2',3'-e][1,4]diazepin-6-one To a solution of 2-chloro-5,11-dihydro-11-ethyl-5-methyl-8-[2-(2-carboxypyrid-4-yl)ethyl]-6H-dipyrido[3,2-b:2',3'-e][1,4]diazepin-6-one (92 mg, 0.21 mmol) and Et₃N (0.03 mL, 0.22 mmol) in t-butanol (20 mL) was added diphenylphosphoryl azide (0.046 g, 0.21 mmol). The reaction mixture was heated at reflux under argon for 16 hours. Solvents were removed by rotary evaporation, and the residue was dissolved in ethyl acetate, washed with saturated aq. sodium bicarbonate, dried (magnesium sulfate), and concentrated. The residue was treated with 2N hydrochloric acid in ethanol at 25°–50° C. for 30 hours. The reaction mixture was concentrated, basified with 6N sodium hydroxide, and extracted with ethyl acetate. Purification by flash chromatography (elution with methanol-dichloromethane) and recrystallization (diethyl ether-petroleum ether) afforded 14 mg (16%) of the title compound, m.p. 95° C. (dec).

Example 72

2-Chloro-5,11-dihydro-11-ethyl-5-methyl-8-[2-(2-hydroxypyrid-4-yl)ethyl]-6H-dipyrido[3,2-b:2',3'-e][1,4]diazepin-6-one The product of Example 71 (14 mg, 0.03 mmol) was dissolved in conc. sulfuric acid (0.06 mL) and water (0.5 mL), and the resultant solution was cooled to 0° C. Sodium nitrite (2.9 mg, 0.04 mmol) was added, and the reaction mixture was warmed to room temperature. After 40 min, the product was extracted with ethyl acetate and recrystallized (ethyl acetate-hexanes) afforded the title compound (4.5 mg, 32%) as beige crystals, m.p. 243°–244° C.

Example 73

5,11-Dihydro-11-ethyl-2-fluoro-5-methyl-8-[2-(3-quinolyl)ethyl]-6H-dipyrido[3,2-b:2',3'-e][1,4]diazepin-6-one By a procedure analogous to that described in Example 51b, 60 mg (0.20 mmol) of 5,11-dihydro-11-ethyl-8-ethynyl-2-fluoro-5-methyl-6H-dipyrido[3,2-b:2',3'-e][1,4]diaepin-6-one [prepared from 8-bromo-5,11-dihydro-11-ethyl-2-fluoro-5-methyl-6H-dipyrido[3,2-b:2',3'-e][1,4]diazepin-6-one (see Example 38) by a route analogous to that described in Example 51a] was coupled with 3-bromoquinoline. Hydrogenation of the resultant acetylene was accomplished as described in Example 3b to provide 6 mg of the title compound, m.p. 154°–156° C. (petroleum ether).

Examples illustrating synthetic Method D

Example 74

2-Chloro-5,11-dihydro-11-ethyl-4-methyl-8-(2-phenylethyl)-6H-dipyrido[3,2-b:2',3'-e][1,4]diazepin-6-one; and

Example 75

3-Bromo-2-chloro-5,11-dihydro-11-ethyl-4-methyl-8-(2-phenylethyl)-6H-dipyrido[3,2-b:2',3'-e][1,4]diazepin-6-one a) (E)- and (Z)-(2-phenylethenyl)tributylstannane To a solution of phenylacetylene (1.02 g) and azobisisobutyronitrile (15 mg) in 10 mL of tetrahydrofuran at 65°–70° C. was added dropwise over 20 min tributyltin hydride (2.9 mL). When addition was complete, solvent was removed at reduced pressure and the residue was purified by reverse phase flash chromatography, eluting with dichloromethane/acetonitrile, to give 0.92 g of the title compounds as a mixture of (E)- and (Z)-isomers.

b) 3-Bromo-2-chloro-5,11-dihydro-11-ethyl-4-methyl-8-(2-phenylethen-1-yl)-6H-dipyrido[3,2-b:2',3'-e][1,4]diazepin-6-one To a solution of 2-chloro-3,8-dibromo-5,11-dihydro-11-ethyl-4-methyl-6H-dipyrido[3,2-b:2',3'-e][1,4]diazepin-6-one (0.224 g), tris(dibenzylideneacetone)dipalladium(0) (10.7 mg), and triphenylarsine (21.4 mg) in 2 mL of tetrahydrofuran under argon was added a mixture of (E)- and (Z)-(2-phenylethenyl)tributylstannane (0.20 g). The reaction mixture was allowed to stand at 50° C. overnight. Solvent was removed, and the residue was purified by flash chromatography, eluting with ethyl acetate/hexanes, to give 115 mg of the title compound, as a mixture of (E)- and (Z)-isomers.

c) 3-Bromo-2-chloro-5,11-dihydro-11-ethyl-4-methyl-8-(2-phenylethen-1-yl)-6H-dipyrido[3,2-b:2',3'-e][1,4]diazepin-6-one (109 mg) was dissolved in 5 mL of acetic acid. Formic acid (1 mL) and 10% palladium on carbon (37 mg) were added and the reaction mixture was stirred overnight under argon. Ammonium formate (0.86 g) was added and stirring was continued for an additional 6 hours. The reaction mixture was filtered, diluted with ethyl acetate, and washed with 6% sodium hydroxide. The organic layer was dried over sodium sulfate, filtered, and concentrated. Purification by flash chromatography, eluting with ethyl acetate/dichloromethane, afforded 7 mg of the compound of Example 74, m.p. 180°–183° C. (isopropyl ether), and 8 mg of the compound of Example 75, m.p. 231°–233° C. (ethyl acetate).

Example 76

5,11-Dihydro-11-ethyl-4-methyl-8-(2-phenylethyl)-6H-dipyrido[3,2-b:2',3'-e][1,4]diazepin-6-one 3-Bromo-2-chloro-5,11-dihydro-11-ethyl-4-methyl-8-(2-phenylethen-1-yl)-6H-dipyrido[3,2-b:2',3'-e][1,4]diazepin- 6-one (0.22 g) was dissolved in 20 mL of methanol, and ammonium formate (2.0 g) and 10% palladium on carbon (0.13 g) were added. The reaction mixture was stirred at room temperature under argon for 6 d. Additional ammonium formate (1.5 g) was added, and the reaction mixture was stirred for an additional 2 d. The reaction mixture was filtered and diluted with ethyl acetate. The organic layer was washed with water, dried over sodium sulfate, and concentrated to give 98 mg of the title compound, which was recrystallized from ethyl acetate/isopropyl ether, to give 51 mg. m.p. 174°–175° C.

Example 77

5,11-Dihydro-11-ethyl-8-(2-phenylethyl)-6H-dipyrido[3,2-b:2',3'-e][1,4]diazepin-6-one By a procedure analogous to that described in Example 74b, 5,11-dihydro-11-ethyl-8-bromo-6H-dipyrido[3,2-b:2',3'-e][1,4]diazepin-6-one (0.17 g) was coupled with a mixture of (E)- and (Z)-(2-phenylethenyl)tributylstannane (0.23 g) in the presence of tris(dibenzylideneacetone)dipalladium (0) and triphenylarsine. The product was dissolved in methanol and hydrogenated over 10% palladium on carbon under 50 p.s.i. of hydrogen for 24 hours. The reaction mixture was filtered through Celite and concentrated. Purification of the residue by flash chromatography, eluting with ethyl acetate/chloroform, afforded 68 mg of the title compound, which crystallized from ethyl acetate/isopropyl ether, m.p. 183°–184° C.

Example 78

8-Benzyl-5,11-dihydro-11-ethyl-5-methyl-6H-dipyrido[3,2-b:2',3'-e][1,4]diazepin-6-one a) Benzyltributyltin To a solution of benzylmagnesium chloride (2.0M in tetrahydrofuran, 1.32 mmol) in 5 mL of tetrahydrofuran at −78° C. under argon was added tributyltin chloride (0.36, 1.27 mmol). After 15 min, the reaction mixture was allowed to warm to room temperature. After 3 hours, solvent was removed, and the residue was purified by flash chromatography, eluting with dichloromethane/hexanes, to give 0.45 g of a clear, colorless oil.

b) 8-Benzyl-5,11-dihydro-11-ethyl-5-methyl-6H-dipyrido[3,2-b:2',3'-e][1,4]diazepin-6-one To a solution of 5,11-dihydro-11-ethyl-8-iodo-5-methyl-6H-dipyrido[3,2-b:2',3'-e][1,4]diazepin-6-one (0.3 g, 0.79 mmol), bis(triphenylphosphine)palladium(II) chloride (18 mg, 0.03 mmol), and 2,6-di-tert-butyl-4-methylphenol (1 crystal) in 5 mL of N,N-dimethylformamide was added benzyltributylstannane (0.36 g, 0.94 mmol). The resultant reaction mixture was heated at 100° C. under argon for 5 hours. An aqueous solution of potassium fluoride was added and the mixture was stirred for 5 hours. The product was extracted with dichloromethane and purified by flash chromatography, eluting with ethyl acetate/dichloromethane, to give 20 mg of the title compound as an oil.

Example 79

5,11-Dihydro-11-ethyl-5-methyl-8-(3-phenylpropyl)-6H-dipyrido[3,2-b:2',3'-e][1,4]diazepin-6-one A solution of naphthalene (0.65 g, 5.07 mmol) in 2 mL of tetrahydrofuran was added to lithium wire (35 mg, 5.04 mmol), and the mixture was stirred overnight at room temperature under argon. A solution of zinc chloride in tetrahydrofuran (0.5M, 5.25 mL, 2.63 mmol) was then added. After 20 min, 1-bromo-3-phenylpropane (0.18 mL, 1.15 mmol) was added, and the reaction mixture was stirred at room temperature for 4.5 hours. Unreacted zinc was allowed to settle, and the supernatant was added by cannula to a solution of 5,11-dihydro-11-ethyl-8-iodo-5-methyl-6H-dipyrido[3,2-b:2',3'-e][1,4]diazepin-6-one (0.22 g, 0.58 mmol) and tetrakis(triphenylphosphine)palladium(0) (70 mg, 0.06 mmol) in 3 mL of tetrahydrofuran. The reaction mixture was allowed to stir overnight at room temperature under argon. The reaction was quenched by the addition of saturated aqueous ammonium chloride, and the product was extracted with ethyl acetate. The organic layer was washed with saturated aqueous sodium chloride, dried over magnesium sulfate, and concentrated. Purification by flash chromatography, eluting with ethyl acetate/dichloromethane, and recrystallization from ethyl acetate/hexanes afforded 16 mg of the title compound as off-white crystals, m.p. 100°–102° C.

Examples illustrating synthetic Method E

Example 80

2-chloro-5,11-dihydro-11-ethyl-8-formyl-5-methyl-6H-dipyrido[3,2-b:2',3'-e][1,4]diazepin-6-one a) 2-chloro-5,11-dihydro-11-ethyl-5-methyl-8-vinyl-6H-dipyrido[3,2-b:2',3'-e]diazepin-6-one A solution of 8-bromo-2-chloro-5,11-dihydro-11-ethyl-5-methyl-6H-dipyrido[3,2-b:2',3'-e][1,4]diazepin-6-one (4.50 g, 12.2 mmol) in N,N-dimethylformamide (50 mL) was treated with tetrakis(triphenylphosphine)palladium(0) (0.28 g, 24 mmol) followed by vinyltributyltin (3.8 mL, 12.9 mmol) and heated to 90° C. with stirring. After 2.5 hours the mixture was poured into water and extracted with dichloromethane (4×100 mL) and ethyl acetate (2×100 mL). The combined organics were washed with 15% aqueous ammonium hydroxide (2×100 mL) and brine (2×100 mL) then dried over sodium sulfate, concentrated and purified quickly by flash chromatography (gradient hexanes to ethyl acetate) to give the title compound (100%), suitable for use in the next reaction.

b) 2-chloro-5,11-dihydro-11-ethyl-8-formyl-5-methyl-6H-dipyrido[3,2-b:2',3'-e][1,4]diazepin-6-one The 2-chloro-5,11-dihydro-11-ethyl-5-methyl-8-vinyl-6H-dipyrido[3,2-b:2',3'-e][1,4]diazepin-6-one (2.34 g, 7.43 mmol) was dissolved in 1:1 dichloromethane/methanol (40 mL) and cooled to −78° C. This solution was then saturated with ozone and a stream ozone was bubbled through for 10 minutes while stirring. The mixture was warmed to ambient temperature and quenched with excess dimethylsulfide. The mixture was then concentrated and the resulting residue was purified by flash chromatography (gradient of hexanes to 1:1 hexanes/ethyl acetate) to give the title compound (1.9 g, 81%), m.p. 199°–201° C.

Example 81

2-chloro-5,11-dihydro-11-ethyl-8-hydroxymethyl-5-methyl-6H-dipyrido[3,2-b:2',3'-e][1,4]diazepin-6-one To a solution of 2-chloro-5,11-dihydro-11-ethyl-8-formyl-5-methyl-6H-dipyrido[3,2-b:2',3'-e][1,4]diazepin-6-one (0.5822 g, 1.84 mmol) in tetrahydrofuran (20 mL) was added water (0.1 mL) followed by sodium borohydride (0.0695 g, 1.84 mmol). The mixture was stirred for 0.5 hour then diluted with brine (20 mL) and extracted with dichloromethane (3×30 mL). The combined organics were dried, concentrated and the residue was purified by flash chromatography (gradient hexanes to ethyl acetate to yield the title compound (0.52 g, 89%), m.p. 166°–168° C.

Example 82

2-chloro-8-chloromethyl-5,11-dihydro-11-ethyl-5-methyl-6H-dipyrido[3,2-b:2',3'-e][1,4]diazepin-6-one The 2-chloro-5,11-dihydro-11-ethyl-8-hydroxymethyl-5-methyl-6H-dipyrido[3,2-b:2',3'-e][1,4]diazepin-6-one (0.52 g, 1.6 mmol) was dissolved in chloroform (10 mL) and treated with thionyl chloride (0.12 mL, 1.6 mmol) followed by triethylamine (0.23 mL, 1.6 mmol). After 0.5 hours stirring the mixture was made alkaline with 15% aqueous sodium hydroxide, diluted with brine (10 mL) and the organic layer was separated. The aqueous layer was then extracted with dichloromethane (2×20 mL). The combined organics were dried over sodium sulfate, filtered, concentrated and the residue was purified by flash chromatography (gradient hexanes to 1:1 hexanes/ethyl acetate) to give the title compound (0.51 g, 93%), m.p. 133°–134° C.

Example 83

5,11-dihydro-11-ethyl-2-fluoro-8-formyl-5-methyl-6H-dipyrido[3,2-b:2',3'-e][1,4]diazepin-6-one Using a procedure analogous to that described in Example 80 the title compound, m.p. 133°–134° C., was prepared from 8-bromo-5,11-dihydro-11-ethyl-2-fluoro-5-methyl-6H-dipyrido[3,2-b:2',3'-e][1,4]diazepin-6-one. The yield was 72% of theory.

Example 84

5,11-dihydro-11-ethyl-2-fluoro-8-hydroxymethyl-5-methyl-6H-dipyrido[3,2-b:2',3'-e][1,4]diazepin-6-one Using a procedure analogous to that described in Example 81 the title compound, m.p. 40° C. (foam), was prepared from 5,11-dihydro-11-ethyl-2-fluoro-8-formyl-5-methyl-6H-dipyrido[3,2-b:2',3'-e][1,4]diazepin-6-one. The yield was quantitative.

Example 85

2-chloro-5,11-dihydro-11-ethyl-8-(β-hydroxy)ethyl-5-methyl-6H-dipyrido[3,2-b:2',3'-e][1,4]diazepin-6-one and Example 86

2-chloro-5,11-dihydro-11-ethyl-8-(α-hydroxy)ethyl-5-methyl-6H-dipyrido[3,2-b:2',3'-e][1,4]diazepin-6-one The 2-chloro-5,11-dihydro-11-ethyl-5-methyl-8-vinyl-6H-dipyrido[3,2-b:2',3'-e][1,4]diazepin-6-one (1.40 g, 4.45 mmol) was dissolved tetrahydrofuran (20 mL) and treated with borane-tetrahydrofuran complex (1.0M in tetrahydrofuran, 8.9 mL, 8.9 mmol). After 2 hours the mixture was treated dropwise with water (5 mL). Then 15% aqueous sodium hydroxide (5 mL) and 30% aqueous hydrogen peroxide was added and the mixture was warmed to 40° C. for 2 hours. The cooled solution was extracted with dichloromethane (3×20 mL) and ethyl acetate (3×50 mL). The combined organics were washed with brine, dried over sodium sulfate, concentrated and the mixture of regioisomers were separated by flash chromatography (1:1 hexanes/ethyl acetate to ethyl acetate gradient) to give 2-chloro-5,11-dihydro-11-ethyl-8-(β-hydroxy)ethyl-5-methyl-6H-dipyrido[3,2-b:2',3'-e][1,4]diazepin-6-one (0.52 g, 35%), m.p. 57°–59° C., and 2-chloro-5,11-dihydro-11-ethyl-8-(α-hydroxy)ethyyl-5-methyl-6H-dipyrido[3,2-b:2',3'-e][1,4]diazepin-6-one (0.15 g, 10%), m.p. 65°–67° C.

Examples illustrating synthetic Method F

Example 87

2-chloro-5,11-dihydro-11-ethyl-5-methyl-8-(phenylamino)methyl-6H-dipyrido[3,2-b:2',3'-e][1,4]diazepin-6-one The 2-chloro-5,11-dihydro-11-ethyl-8-formyl-5-methyl-6H-dipyrido[3,2-b:2',3'-e][1,4]diazepin-6-one (0.50 g, 0.16 mmol) was dissolved/suspended in methanol (2 mL) and treated with sodium cyanoborohydride (0.030 g, 0.47 mmol) followed by aniline (0.043 mL, 4.7 mmol). The mixture was stirred for 5 minutes then acetic acid (0.020 mL, 0.35 mmol) was added. After an additional 3 hours at room temperature the mixture was made alkaline with 15% sodium hydroxide and the white suspension was extracted with dichloromethane (3×10 mL). The combined organics were washed with brine, dried over sodium sulfate, and concentrated. The residue was purified by column chromatography then chromatotron (hexane to 1:1 hexanes/ethyl acetate gradient) to give the title compound (0.031 g, 50%), m.p. 79°–80° C.

Example 88

8-(3-aminophenylamino)methyl-2-chloro-5,11-dihydro-11-ethyl-5-methyl-6H-dipyrido[3,2-b:2',3'-e][1,4]diazepin-6-one Using a procedure analogous to that described in Example 87 the title compound, m.p. 188°–90° C., was prepared from 2-chloro-5,11-dihydro-11-ethyl-8-formyl-5-methyl-6H-dipyrido[3,2-b:2',3'-e][1,4]diazepin-6-one and m-phenylenediamine. The yield was 31% of theory.

Examples illustrating synthetic Method G

Example 89

2-chloro-5,11-dihydro-11-ethyl-8-hydroxy-5-methyl-6H-dipyrido[3,2-b:2',3'-e[]1,4]diazepin-6-one The 2-chloro-5,11-dihydro-11-ethyl-8-formyl-5-methyl-6H-dipyrido[3,2-b:2',3'-e][1,4]diazepin-6-one (1.02 g, 3.22 mmol) was dissolved in dichloromethane (10 mL) and treated with m-chloroperbenzoic acid (80% wt., 1.04 g, 4.83 mmol). The mixture was stirred for 16 hours then treated with methanol and stirred for 8 hours more. The mixture was diluted with saturated aqueous sodium bicarbonate (20 mL) and extracted with dichloromethane (3×25 mL). The combined organics were washed with saturated aqueous sodium bicarbonate (2×20 mL), dried over sodium sulfate, concentrated and the residue was purified by flash chromatography (hexanes to ethyl acetate gradient) to give the title compound (0.37 g, 38%), m.p. 236°–237° C. The product could be recrystallized from hexanes/ethyl acetate.

Examples illustrating synthetic Method H

Example 90

2-chloro-5,11-dihydro-11-ethyl-5-methyl-8-phenylmethoxy-6H-dipyrido[3,2-b:2',3'-e][1,4]diazepin-6-one The 2-chloro-5,11-dihydro-11-ethyl-8-hydroxy-5-methyl-6H-dipyrido[3,2-b:2',3'-e][1,4]diazepin-6-one (0.052 g, 0.17 mmol) was dissolved in tetrahydrofuran and treated with excess sodium hydride (60% wt.) followed by benzyl bromide (0.04 mL, 0.34 mmol). After 24 hours stirring the mixture was cooled to 0° C. and the excess sodium hydride was quenched by the dropwise addition of water and the resulting solution was extracted with dichloromethane (3×20 mL) The combined organics were dried over magnesium sulfate, concentrated and the residue was purified by chromatography (hexanes to 1:1 hexanes/ethyl acetate gradient) followed by crystallization from hexanes to give the title compound (0.035 g, 52%), m.p. 159°–160° C.

Example 91

5,11-dihydro-11-ethyl-2-fluoro-5-methyl-8-((N-oxo-pyrid-4-yl)oxy)methyl-6H-dipyrido[3,2-b:2',3'-e][1,4]diazepin-6-one 5,11-dihydro-11-ethyl-2-fluoro-8-hydroxymethyl-5-methyl-6H-dipyrido[3,2-b:2',3'-e][1,4]diazepin-6-one (0.084 g, 0.28 mmol) was dissolved in tetrahydrofuran (10 mL) and was treated with excess sodium hydride. After 5 minutes stirring the 4-nitropyridine N-oxide (0.058 g, 0.42 mmol) was added and the mixture was stirred for 24 hours. The reaction mixture was then diluted with saturated aqueous bicarbonate (10 mL) and extracted with dichloromethane (4×20 mL). The combined organics dried over sodium sulfate, concentrated and the residue was purified by preparative thin layer chromatography (TLC) (10% methanol/dichloromethane eluting twice) followed by crystallization from ethyl acetate/hexanes to give the title compound (0.076 g, 69%), m.p. 194°–196° C.

Example 92

2-chloro-5,11-dihydro-11-ethyl-5-methyl-8-(N-oxo-pyrid-4-yloxy)methyl-6H-dipyrido[3,2-b:2',3'-e][1,4]diazepin-6-one Using a procedure analogous to that described in Example 91 the title compound, m.p. 208°–210° C., was prepared from 2-chloro-5,11-dihydro-11-ethyl-8-hydroxymethyl-5-methyl-6H-dipyrido[3,2-b:2',3'-e][1,4]diazepin-6-one. The yield was 86% of theory.

Example 93

2-chloro-5,11-dihydro-11-ethyl-8-(2-methylpyrid-4-yloxy)methyl-5-methyl-6H-dipyrido[3,2-b:2',3'-e][1,4]diazepin-6-one Using a procedure analogous to that described in Example 91, except potassium hydride was employed as the base instead of sodium hydride, the title compound, m.p. 163°–164° C., was prepared from 2-chloro-5,11-dihydro-11-ethyl-8-hydroxymethyl-5-methyl-6H-dipyrido-[3,2-b:2',3'-e][1,4]diazepin-6-one and 4-nitro-2-picoline. The yield was 69% of theory.

Example 94

2-chloro-5,11-dihydro-11-ethyl-5-methyl-8-(N-oxo-2-methylpyrid-4-yloxy)methyl-6H-dipyrido[3,2-b:2',3'-e][1,4]diazepin-6-one Using a procedure analogous to that described in Example 91, except potassium hydride was employed as the base instead of sodium hydride, the title compound, m.p. 190°–192° C., was prepared from 2-chloro-5,11-dihydro-11-ethyl-8-hydroxymethyl-5-methyl-6H-dipyrido[3,2-b:2',3'-e][1,4]diazepin-6-one and 4-nitro-2-picoline N-oxide. The yield was 41% of theory.

Example 95

2-chloro-5,11-dihydro-11-ethyl-5-methyl-8-(N-oxo-2-trifluoromethylpyrid-4-yloxy)methyl-6H-dipyrido[3,2-b:2',3'-e][1,4]diazepin-6-one Using a procedure analogous to that described in Example 91, except potassium hydride was employed as the base instead of sodium hydride, the title compound, m.p. 105°–108° C., was prepared from 2-chloro-5,11-dihydro-11-ethyl-8-hydroxymethyl-5-methyl-6H-dipyrido[3,2-b:2',3'-e][1,4]diazepin-6-one and 4-nitro-2-trifluoromethylpyridine N-oxide. The yield was 36% of theory.

Example 96

2-chloro-5,11-dihydro-11-ethyl-5-methyl-8-[2-(N-oxo-pyrid-4-yloxy)ethyl]-6H-dipyrido[3,2-b:2',3'-e[]1,4]diazepin-6-one a) 2-chloro-5,11-dihydro-11-ethyl-8-hydroxyethyl-5-methyl-6H-dipyrido[3,2-b:2'3'diazepin-6-one A solution of 8-bromo-2-chloro-5,11-dihydro-11-ethyl-5-methyl-6H-dipyrido[3,2-b:2',3'-e][1,4]diazepin-6-one (4.50 g, 12.2 mmol) in N,N-dimethylformamide (45 mL) was treated sequentially with tetrakis(triphenylphosphine)palladium(0) (0.28 g, 24 mmol) and allyltributyltin (3.8 mL, 12.2 mmol) and heated to 80° C. with stirring. The reaction was monitored by NMR analysis of aliquots. When the reaction was complete (several hours) the excess N,N-dimethylformamide and tin byproducts were removed in vacuo. The resulting residue was dissolved in 1:1 dichloromethane/methanol (45 mL) and cooled to −78° C. This solution was then saturated with ozone and a stream ozone was bubbled through for 20 minutes while stirring. The mixture was warmed to ambient temperatures and quenched with excess dimethylsulfide. The solvent was then removed in vacuo, the residue was dissolved in tetrahydrofuran (50 mL) and treated with excess sodium borohydride. After 2 hours the stirred mixture was quenched with brine, diluted with water (10 mL) and dichloromethane (100 mL). The organic layer was separated and the aqueous was extracted with dichloromethane (100 mL). The combined organics were dried over sodium sulfate, filtered and concentrated. The residue was purified by flash chromatography (gradient of 1:1 hexanes/ethyl acetate to ethyl acetate) to yield the title compound (1.5 g, 37%).

b) 2-chloro-5,11-dihydro-11-ethyl-5-methyl-8-((1-oxo-pyridin-4-yl)oxy)ethyl-6H-dipyrido[3,2-b:2',3'-e][1,4]diazepin-6-one Using a procedure analogous to that described in Example 91, except potassium hydride was employed as the base instead of sodium hydride, the title compound, m.p. 173°–174° C., was prepared from 2-chloro-5,11-dihydro-11-ethyl-8-hydroxyethyl-5-methyl-6H-dipyrido[3,2-b:2',3'-e][1,4]diazepin-6-one and 4-nitropyridine N-oxide. The yield was 42% of theory.

Example 97

5,11-dihydro-11-ethyl-5-methyl-8-((1-oxo-pyridin-4-yl)oxy)methyl-6H-dipyrido[3,2-b:2',3'-e][1,4]diazepin-6-one a) 5,11-dihydro-11-ethyl-8-formyl-5-methyl-6H-dipyrido[3,2-b:2',3'-e][1,4]diazepin-6-one Using a procedure analogous to that described in Example 80, the title compound, was prepared from 8-iodo-5,11-dihydro-11-ethyl-5-methyl-6H-dipyrido[3,2-b:2',3'-e][1,4]diazepin-6-one and vinyltributyltin. The yield was 57% of theory.

b) 5,11-dihydro-11-ethyl-8-hydroxymethyl-5-methyl-6H-dipyrido[3,2-b:2',3'-e][1,4]diazepin-6-one Using a procedure analogous to that described in Example 81, except the purification by chromatography was omitted, the title compound, was prepared from 5,11-dihydro-11-ethyl-8-formyl-5-methyl-6H-dipyrido[3,2-b:2',3'-e][1,4]diazepin-6-one. The yield was 83% of theory.

c) 5,11-dihydro-11-ethyl-5-methyl-8-((1-oxo-pyridin-4-yl)oxy)methyl-6H-dipyrido[3,2-b:2',3'-e][1,4]diazepin-6-one Using a procedure analogous to that described in Example 91, except potassium hydride was employed as the base instead of sodium hydride, the title compound, m.p. 218°–219° C., was prepared from 5,11-dihydro-11-ethyl-8-hydroxymethyl-5-methyl-6H-dipyrido[3,2-b:2',3'-e][1,4]diazepin-6-one and 4-nitropyridine N-oxide. The yield was 61% of theory.

Examples illustrating synthetic Method I

Example 98

2-chloro-5,11-dihydro-11-ethyl-5-methyl-8-(3-nitrophenylamino)methyl-6H-dipyrido[3,2-b:2',3'-e][1,4]diazepin-6-one 3-Nitrophenol (0.0413 g, 0.297 mmol) in dimethyl sulfoxide (2 mL) was treated with potassium tert-butoxide (1.0M in tetrahydrofuran, 0.312 mL, 0.312 mmol). To the resulting stirred dark red solution was added 2-chloro-8-chloromethyl-5,11-dihydro-11-ethyl-5-methyl-6H-dipyrido[3,2-b:2',3'-e][1,4]diazepin-6-one (0.100 g, 0.297 mmol) and the mixture was stirred an additional 2 hours. The mixture was diluted with ethyl acetate (50 mL) washed with brine, water, and brine (25 mL each). The organics were dried over sodium sulfate, concentrated and the residue was purified by flash chromatography (dichloromethane to 1:1 dichloromethane/ethyl acetate gradient) to give the title compound (0.124 g, 95%), m.p. 171°–172° C.

Example 99

8-(3-aminophenyloxy)methyl-2-chloro-5,11-dihydro-11-ethyl-5-methyl-6H-dipyrido[3,2-b:2',3'-e][1,4]diazepin-6-one The 2-chloro-5,11-dihydro-11-ethyl-5-methyl-8-(3-nitrophenylamino)methyl-6H-dipyrido[3,2-b:2',3'-e][1,4]diazepin-6-one (0.080 g, 0.18 mmol) was dissolved in acetic acid (5 mL) and treated with a solution of stannous chloride dihydrate (0.154 g, 0.68 mmol) in concentrated hydrochloric acid (2 mL). After stirring for 17 hours the resulting mixture was made alkaline with 50% aqueous sodium hydroxide and extracted with dichloromethane (8×20 mL). The combined organics were dried over sodium sulfate, concentrated and the residue was purified by flash chromatography (hexanes to 1:1 hexanes/ethyl acetate gradient) to the title compound (0.046 g, 62%), m.p. 148°–149° C.

Example 100

2-chloro-5,11-dihydro-11-ethyl-5-methyl-8-(phenyloxy)methyl-6H-dipyrido[3,2-b:2',3'-e][1,4]diazepin-6-one Using a procedure analogous to that described in Example 98, except sodium bis(trimethylsilyl)amide was employed as the base instead of potassium tert-butoxide, the title compound, m.p. 140°–141° C., was prepared from 2-chloro-8-chloromethyl-5,11-dihydro-11-ethyl-5-methyl-6H-dipyrido[3,2-b:2',3'-e][1,4]diazepin-6-one and phenol. The yield was 78% of theory.

Example 101

2-chloro-5,11-dihydro-11-ethyl-8-(3-fluorophenyl)methyl-5-methyl-6H-dipyrido[3,2-b:2',3'-e][1,4]diazepin-6-one Using a procedure analogous to that described in Example 98, the title compound, m.p. 104°–105° C., was prepared from 2-chloro-8-chloromethyl-5,11-dihydro-11-ethyl-5-methyl-6H-dipyrido[3,2-b:2',3'-e][1,4]diazepin-6-one and 3-fluorophenol. The yield was 70% of theory.

Example 102

2-chloro-5,11-dihydro-11-ethyl-8-(2-fluorophenyloxy)methyl-5-methyl-6H-dipyrido[3,2-b:2',3'-e][1,4]diazepin-6-one Using a procedure analogous to that described in Example 98, the title compound, m.p. 109°–110° C., was prepared from 2-chloro-8-chloromethyl-5,11-dihydro-11-ethyl-5-methyl-6H-dipyrido[3,2-b:2',3'-e][1,4]diazepin-6-one and 2-fluorophenol. The yield was 52% of theory.

Example 103

2-chloro-5,11-dihydro-11-ethyl-8-(4-fluorophenyloxy)methyl-5-methyl-6H-dipyrido[3,2-b:2',3'-e][1,4]diazepin-6-one Using a procedure analogous to that described in Example 98, the title compound, m.p. 143°–144° C., was prepared from 2-chloro-8-chloromethyl-5,11-dihydro-11-ethyl-5-methyl-6H-dipyrido[3,2-b:2',3'-e][1,4]diazepin-6-one and 4-fluorophenol. The yield was 57% of theory.

Example 104

2-chloro-5,11-dihydro-11-ethyl-8-(3-hydroxyphenyl)methyl-5-methyl-6H-dipyrido[3,2-b:2',3'-e][1,4]diazepin-6-one Resorcinol (0.082 g, 0.74 mmol) in dimethyl sulfoxide (1 mL) was treated with potassium tert-butoxide (1.0M in tetrahydrofuran, 0.15 mL, 0.15 mmol). The resulting stirred solution was treated with 2-chloro-8-chloromethyl-5,11-dihydro-11-ethyl-5-methyl-6H-dipyrido[3,2-b:2',3'-e][1,4]diazepin-6-one (0.050 g, 0.14 mmol) in dimethyl sulfoxide (1 mL) and the mixture was stirred an additional 16 hours. The mixture was diluted with ethyl acetate (50 mL) washed with brine, water, and brine (15 mL each). The organics were dried over sodium sulfate, concentrated and the residue was purified by flash chromatography (hexanes to 1:1 hexanes/ethyl acetate gradient) followed by crystallization from hexanes to give the title compound (0.031 g, 51%), m.p. 219°–220° C.

Example 105

2-chloro-5,11-dihydro-11-ethyl-8-(4-hydroxyphenyloxy)methyl-5-methyl-6H-dipyrido[3,2-b:2',3'-e][1,4]diazepin-6-one Using a procedure analogous to that described in Example 104, the title compound, m.p. 199°–200° C., was prepared from 2-chloro-8-chloromethyl-5,11-dihydro-11-ethyl-5-methyl-6H-dipyrido[3,2-b:2',3'-e][1,4]diazepin-6-one and hydroquinone. The yield was 67% of theory.

Example 106

2-chloro-5,11-dihydro-11-ethyl-8-(2-hydroxyphenyloxy)methyl-5-methyl-6H-dipyrido[3,2-b:2',3'-e][1,4]diazepin-6-one Using a procedure analogous to that described in Example 104, the title compound, m.p. 172°–173° C., was prepared from 2-chloro-8-chloromethyl-5,11-dihydro-11-ethyl-5-methyl-6H-dipyrido[3,2-b:2',3'-e][1,4]diazepin-6-one and catechol. The yield was 58% of theory.

Example 107

2-chloro-5,11-dihydro-11-ethyl-5-methyl-8-(3-pyridyloxy)methyl-6H-dipyrido[3,2-b:2',3'-e][1,4]diazepin-6-one Using a procedure analogous to that described in Example 98, the title compound, m.p. 183°–184° C., was prepared from 2-chloro-8-chloromethyl-5,11-dihydro-11-ethyl-5-methyl-6H-dipyrido[3,2-b:2',3'-e][1,4]diazepin-6-one and 3-hydroxypyridine. The yield was 72% of theory.

Example 108

2-chloro-5,11-dihydro-11-ethyl-8-(3-methoxyphenyloxy)methyl-5-methyl-6H-dipyrido[3,2-b:2',3'-e][1,4]diazepin-6-one Using a procedure analogous to that described in Example 98, the title compound, m.p. 95°–97° C., was prepared from 2-chloro-8-chloromethyl-5,11-dihydro-11-ethyl-5-methyl-6H-dipyrido[3,2-b:2',3'-e][1,4]diazepin-6-one and 3-methoxyphenol. The yield was 54% of theory.

Example 109

2-chloro-5,11-dihydro-11-ethyl-8-(4-(methoxycarbonyl)phenyloxy)methyl-5-methyl-6H-dipyrido[3,2-b :2',3'-e][1,4]diazepin-6-one Using a procedure analogous to that described in Example 98, the title compound, m.p. 196°–197° C., was prepared from 2-chloro-8-chloromethyl5,11-dihydro-11-ethyl-5-methyl-6H-dipyrido[3,2-b:2',3'-e][1,4]diazepin-6-one and methyl 4-hydroxybenzoate. The yield was 45% of theory.

Example 110

2-chloro-5,11-dihydro-11-ethyl-8-(2-(methyoxycarbonyl)phenyloxy)methyl-5-methyl-6H-dipyrido[3,2-b:2',3'-e][1,4]diazepin-6-one Using a procedure analogous to that described in Example 98, the title compound, m.p. 155°–156° C., was prepared from 2-chloro-8-chloromethyl-5,11-dihydro-11-ethyl-5-methyl-6H-dipyrido[3,2-b:2',3'-e][1,4]diazepin-6-one and methyl salicylate. The yield was 57% of theory.

Example 111

2-chloro-5,11-dihydro-11-ethyl-8-((3-(methoxycarbonyl)phenyloxy)methyl-5-methyl-6H-dipyrido[3,2-b:2',3'-e][1,4]diazepin-6-one Using a procedure analogous to that described in Example 98, the title compound, m.p. 163°–164° C., was prepared from 2-chloro-8-chloromethyl-5,11-dihydro-11-ethyl-5-methyl-6H-dipyrido[3,2-b:2',3'-e][1,4]diazepin-6-one and methyl 3-hydroxybenzoate. The yield was 90% of theory.

Example 112

2-chloro-5,11-dihydro-11-ethyl-8-(3-(carboxy)phenyloxy)methyl-5-methyl-6H-dipyrido[3,2-b:2',3'-e][1,4]diazepin-6-one 2-chloro-5,11-dihydro-11-ethyl-8-((3-(methoxycarbonyl)phenyloxy)methyl-5-methyl-6H-dipyrido[3,2-b:2',3'-e][1,4]diazepin-6-one (0.023 g, 0.051 mmol) was dissolved in tetrahydrofuran (1 mL) and treated with aqueous lithium hydroxide (1M, 2 mL, 2 mmol). The reaction was stirred until no starting material was detected by TLC. The mixture was then acidified to pH=6 with saturated aqueous ammonium chloride then extracted with dichloromethane (3×20 mL). The combined organics were dried over sodium sulfate, concentrated and the residue was recrystallized from hexanes/ethyl acetate to give the title compound (0.015 g, 67%), m.p. 181°–182° C.

Example 113

8-(3-(aminocarbonyl)phenyloxy)methyl-2-chloro-5,11-dihydro-11-ethyl-5-methyl-6H-dipyrido[3,2-b:2',3'-e][1,4]diazepin-6-one The 2-chloro-5,11-dihydro-11-ethyl-8-((3-(methoxycarbonyl)phenyloxy)methyl-5-methyl-6H-dipyrido[3,2-b:2',3'-e][1,4]diazepin-6-one (0.033 g, 0.073 mmol) was dissolved in tetrahydrofuran (5 mL) and treated with aqueous lithium hydroxide (1.0M, 0.073 mL, 0.073 mmol). After 16 hours the mixture was diluted with saturated aqueous ammonium chloride (15 mL), extracted with ethyl acetate (2×20 mL), dried over sodium sulfate and concentrate. The residue was azeotropically dried from benzene (50 mL)and used directly. The residue was dissolved in dichloromethane (10 mL) and was treated with oxalyl chloride (0.063 mL, 0.72 mmol) followed by a catalytic amount of N,N-dimethylformamide (0.004 mL). The mixture was stirred for 0.5 hour then concentrated in vacuo, redissolved in dichloromethane (10 mL) and treated with anhydrous ammonia (gas) and stirred for 5 minutes more. The mixture was then diluted with ethyl acetate (15 mL), washed with brine (2×10 mL), dried over sodium sulfate, concentrated and the residue was purified by chromatography (hexanes to ethyl acetate gradient to give the title compound (0.025 g, 79%), m.p. 96°–98° C.

Example 114

2-chloro-5,11-dihydro-11-ethyl-8-(4-indolyloxy)methyl-5-methyl-6H-dipyrido[3,2-b:2',3'-e][1,4]diazepin-6-one Using a procedure analogous to that described in Example 98, the title compound, m.p. 183°–185° C., was prepared from 2-chloro-8-chloromethyl-5,11-dihydro-11-ethyl-5-methyl-6H-dipyrido[3,2-b:2',3'-e][1,4diazepin-6-one and 4-hydroxyindole. The yield was 14% of theory.

Example 115

2-chloro-5,11-dihydro-11-ethyl-8-(5-indolyloxy)methyl-5-methyl-6H-dipyrido[3,2-b:2',3'-e][1,4]diazepin-6-one Using a procedure analogous to that described in Example 98, the title compound, m.p. 176°–178° C., was prepared from 2-chloro-8-chloromethyl-5,11-dihydro-11-ethyl-5-methyl-6H-dipyrido[3,2-b:2',3'-e][1,4]diazepin-6-one and 5-hydroxyindole. The yield was 22% of theory.

Example 116

2-chloro-5,11-dihydro-11-ethyl-5-methyl-8-(N-methylphenylamino)methyl-6H-dipyrido[3,2-b:2',3'-e][1,4]diazepin-6-one The 2-chloro-8-chloromethyl-5,11-dihydro-11-ethyl-5-methyl-6H-dipyrido[3,2-b:2',3'-e][1,4]diazepin-6-one (0.050 g, 0.15 mmol) was dissolved in N-methylaniline (1 mL) and stirred for 3 days. The mixture was purified by column chromatography (hexanes to ethyl acetate gradient) to give the title compound (0.025 g, 41%), m.p. 55°–57° C., foam.

Example 117

2-chloro-5,11-dihydro-11-ethyl-5-methyl-8-(phenylthio)methyl-6H-dipyrido[3,2-b:2',3'-e][1,4]diazepin-6-one To a solution of thiophenol (0.16 mL, 1.6 mmol) in N,N-dimethylformamide (15 mL) was treated with sodium hydride (60% wt, 62 mg, 1.6 mmol). After stirring 15 minutes the 2-chloro-8-chloromethyl-5,11-dihydro-11-ethyl-5-methyl-6H-dipyrido[3,2-b:2',3'-e][1,4]diazepin-6-one (0.50 g, 1.5 mmol) was added and the mixture was stirred for 18 hours more. The excess thiolate was quenched with methanol and the mixture was diluted with aqueous sodium bicarbonate and extracted with dichloromethane. The organics were dried over sodium sulfate, filtered, concentrated and the residue was purified by flash chromatography (hexanes/ethyl acetate) and recrystallization from hexanes/ethyl acetate to give the title compound (0.378 g, 62%), m.p. 92°–93° C.

Example 118

2-chloro-5,11-dihydro-11-ethyl-5-methyl-8-(phenylsulfonyl)methyl-6H-dipyrido[3,2-b:2',3'e][1,4]diazepin-6-one and

Example 119

2-chloro-5,11-dihydro-11-ethyl-5-methyl-8-(phenylsulfinyl)methyl-6H-dipyrido[3,2-b:2',3'-e][1,4]diazepin-6-one The 2-chloro-5,11-dihydro-11-ethyl-5-methyl-8-(phenylthio)methyl-6H-dipyrido[3,2-b:2',3'-e][1,4]diazepin-6-one (0.070 g, 0.17 mmol) was dissolved in dichloromethane (2.5 mL), cooled to 0° C. and treated with m-chloroperbenzoic acid (60% wt., 0.059 g, 0.21 mmol). After 1 hour the mixture was diluted with dichloromethane (20 mL) and washed with saturated aqueous sodium bicarbonate. The organic phase was dried, concentrated and the resulting residue was purified by preparative thin layer chromatography to give 2-chloro-5,11-dihydro-11-ethyl-5-methyl-8-(phenylsulfonyl)methyl-6H-dipyrido[3,2-b:2',3'-e][1,4]diazepin-6-one (0.029 g, 39%), m.p. 98°–100° C., and 2-chloro-5,11-dihydro-11-ethyl-5-methyl-8-(phenylsulfinyl)methyl-6H-dipyrido[3,2-b:2',3'-e][1,4]diazepin-6-one (0.008 g, 11% m.p. 96°–98° C.

Example 120

2-chloro-5,11-dihydro-11-ethyl-5-methyl-8-(pyrid-4-ylthio)methyl-6H-dipyrido[3,2-b:2',3'-e][1,4]diazepin-6-one Using a procedure analogous to that described in Example 117, the title compound, m.p. 140°–142° C., was prepared from 2-chloro-8-chloromethyl-5,11-dihydro-11-ethyl-5-methyl-6H-dipyrido[3,2-b:2',3'-e][1,4]diazepin-6-one and 4-mercaptopyridine. The yield was 79% of theory.

Example 121

2-chloro-5,11-dihydro-11-ethyl-5-methyl-8-(pyrimidinyl-2-thio)methyl-6H-dipyrido[3,2-b:2',3'-e][1,4]diazepin-6-one Using a procedure analogous to that described in Example 98, the title compound, m.p. 163°–164° C., was prepared from 2-chloro-8-chloromethyl-5,11-dihydro-11-ethyl-5-methyl-6H-dipyrido[3,2-b:2',3'-e][1,4]diazepin-6-one and 6-mercaptopyrimidine. The yield was 69% of theory.

Example 122

2-chloro-5,11-dihydro-11-ethyl-5-methyl-8-(1H-pyrazolo[3,4-d]pyrimidine-4-ylthio)methyl-6H-dipyrido[3,2-b:2',3'-e][1,4]diazepin-6-one Using a procedure analogous to that described in Example 98, the title compound, m.p. 128°–130° C., was prepared from 2-chloro-8-chloromethyl-5,11-dihydro-11-ethyl-5-methyl-6H-dipyrido[3,2-b:2',3'-e][1,4]diazepin-6-one and 3-mercapto-1H-pyrazolo[3,4-d]pyrimidine. The yield was 75% of theory.

Example 123

2-chloro-5,11-dihydro-11-ethyl-5-methyl-8-(purin-6-ylthio)methyl-6H-dipyrido[3,2-b:2',3'-e][1,4]diazepin-6-one Using a procedure analogous to that described in Example 98, the title compound, m.p. 148°–151° C., was prepared from 2-chloro-8-chloromethyl-5,11-dihydro-11-ethyl-5-methyl-6H-dipyrido[3,2-b:2',3'-e][1,4]diazepin-6-one and 6-mercaptopurine. The yield was 67% of theory.

Examples illustrating synthetic Method J

Example 124

2-Chloro-5,11-dihydro-11-ethyl-5-methyl-8-(pyrid-4-yloxy)methyl-6H-dipyrido[3,2-b:2',3'-e][1,4]diazepin-6-one The 2-chloro-5,11-dihydro-11-ethyl-5-methyl-8-(N-oxo-pyrid-4-yloxy)methyl-6H-dipyrido[3,2-b:2',3'-e][1,4]diazepin-6-one (0.099 g, 0.24 mmol) in chloroform (20 mL) was treated with phosphorus trichloride (0.025 mL, 0.29 mmol) and stirred for 2 hours. The mixture was then made alkaline with 15% aqueous sodium hydroxide and the organic layer was separated. The aqueous layer was extracted with dichloromethane (3×20 mL) and the combined organics were dried over sodium sulfate and concentrated in vacuo to give quantitatively the title compound, m.p. 169°–170° C.

Example 125

5,11-dihydro-11-ethyl-2-fluoro-5-methyl-8-(pyrid-4-yloxy)methyl-6H-dipyrido[3,2-b:2',3'-e][1,4]diazepin-6-one Using a procedure analogous to that described in Example 124, except the product was purified by crystallization from ethyl acetate/hexanes, the title compound, m.p. 146°–148° C., was prepared from 5,11-dihydro-11-ethyl-2-fluoro-5- methyl-8-(N-oxo-pyrid-4-yloxy)methyl-6H-dipyrido[3,2-b:2',3'-e][1,4]diazepin-6-one. The yield was 81% of theory.

Example 126

2-chloro-5,11-dihydro-11-ethyl-5-methyl-8-(2-trifluoromethylpyrid-4-yloxy)methyl-6H-dipyrido[3,2-b;2',3'-e][1,4]diazepin-6-one Using a procedure analogous to that described in Example 124, except the product was purified by preparative thin layer chromatography (5% methanol/dichloromethane) and further purified by precipitation from ethyl acetate solution with hexanes, the title compound, m.p. 170°-171° C., was prepared from 2-chloro-5,11-dihydro-11-ethyl-5-methyl-8-(N-oxo-2-trifluoromethylpyrid-4-yloxy)methyl-6H-dipyrido[3,2-b:2',3'-e][1,4]diazepin-6-one. The yield was 67% of theory.

Example 127

2-chloro-5,11-dihydro-11-ethyl-5-methyl-8-[2-(pyrid-4-yloxy)ethyl]-6H-dipyrido[3,2-b:2',3'-e][1,4]diazepin-6-one Using a procedure analogous to that described in Example 124, except the product was purified by preparative thin layer chromatography (5% methanol/dichloromethane) and further purified by precipitation from ethyl acetate solution with hexanes, the title compound was prepared from 2-chloro-5,11-dihydro-11-ethyl-5-methyl-8-(N-oxo-pyrid-4-yloxy)ethyl-6H-dipyrido[3,2-b:2',3'-e][1,4]diazepin-6-one. The yield was 74% of theory.

Example 128

5,11-dihydro-11-ethyl-5-methyl-8-(pyrid-4-yloxy)ethyl-6H-dipyrido[3,2-b:2',3'-e][1,4]diazepin-6-one Using a procedure analogous to that described in Example 124, except the product was purified by preparative thin layer chromatography (5% methanol/dichloromethane) and further purified by precipitation from ethyl acetate solution with hexanes, the title compound, m.p. 164°-165° C., was prepared from 5,11-dihydro-11-ethyl-5-methyl-8-(N-oxo-pyrid-4-yloxy)methyl-6H-dipyrido[3,2-b:2',3'-e][1,4]diazepin-6-one. The yield was 83% of theory.

EXAMPLE A

Capsules or Tablets

| | A-1 | | A-2 |
|---|---|---|---|
| Ingredients | Quantity | Ingredients | Quantity |
| Compound of Ex. 3 | 250 mg | Compound of Ex. 3 | 50 mg |
| Starch | 160 mg | Dicalcium Phosphate | 160 mg |
| Microcryst. Cellulose | 90 mg | Microcrys. Cellulose | 90 mg |
| Na Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of Example 3 is blended into a powder mixture with the premixed excipient materials as identified above with the exception of the lubricant. The lubricant is then blended in and the resulting blend compressed into tablets or filled into hard gelatin capsules.

EXAMPLE B

Parenteral Solutions

| Ingredients | Quantity |
|---|---|
| Compound of Example 3 | 500 mg |
| Tartaric acid | 1.5 g |
| Benzyl Alcohol | 0.1% by weight |
| Water for injection | q.s. to 100 mL |

The excipient materials are mixed with the water and thereafter the compound of Example 3 is added. Mixing is continued until the solution is clear. The pH of this solution is adjusted to 3.0 and is then filtered into the appropriate vials or ampoules and sterilized by autoclaving.

EXAMPLE C

Nasal Solutions

| Ingredients | Quantity |
|---|---|
| Compound of 3 | 100 mg |
| Citric acid | 1.92 g |
| Benzalkonium chloride | 0.025% by weight |
| EDTA | 0.1% by weight |
| Polyvinyl alcohol | 10% by weight |
| Water | q.s. to 100 mL |

The excipient materials are mixed with the water and thereafter the compound of Example 3 is added and mixing is continued until the solution is clear. The pH of this solution is adjusted to 4.0 and is then filtered into the appropriate vials or ampoules.

We claim:

1. A compound of formula 1

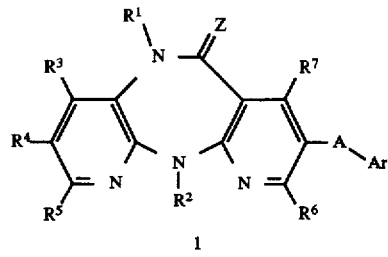

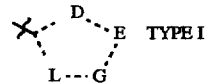

Ar =  or

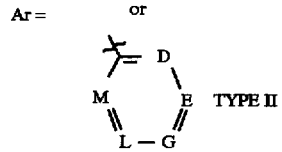

wherein,

A is a connecting chain of 1 to 3 atoms, wherein one of the atoms is oxygen, phosphorous or sulfur (optionally oxidized or unoxidized), or nitrogen (unsubstituted or substituted with methyl or acetyl), and the remaining atoms are carbon; or, all of the atoms are carbon atoms, wherein two of the atoms form an unsaturated alkynyl or cis- or trans-alkenyl bond, or all of the atoms are connected by single bonds and one of the atoms is optionally unsubstituted or substituted with oxo, methyl, hydroxy, amino, or halogen wherein halogen is defined as fluoro, chloro bromo or iodo; or, A is a connecting chain of 2 atoms, wherein one of the atoms is nitrogen (unsubstituted or substituted with methyl) or oxygen, and the adjacent position is carbonyl; or, A is a 1,2-disubstituted cyclopropyl or oxiranyl ring;

D, E, G, and L form a five-membered heteroaromatic ring of type I, wherein the dotted bonds represent either double or single bonds depending on the valency of the atoms, either D or E is nitrogen (unsubstituted or substituted with methyl, ethyl, or acetyl), oxygen, or sulfur, and the three remaining positions are carbon, wherein one or two of these carbon atoms are optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, one of D, E, G, and L is nitrogen, one is oxygen or sulfur, and the two remaining positions are carbon optionally unsubstituted or substituted with alkyl, alkyloxy, or alkylmercapto of 1 to 4 carbon atoms, trifluoromethyl, hydroxymethyl, hydroxyethyl, halogen, acetyl, methoxy or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, two of D, E, G, and L are nitrogen (wherein one of the nitrogen atoms is unsubstituted or substituted with methyl, ethyl, acetyl, mono- or dimethylaminosulfonyl, methoxy- or ethoxycarbonyl, aminocarbonyl, alkylaminocarbonyl, or phenylaminocarbonyl), and the two remaining positions are carbon optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, two of D, E, G, and L are nitrogen, one is oxygen or sulfur, and the remaining position is carbon optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, three of D, E, G, and L are nitrogen (wherein one of the nitrogen atoms is unsubstituted or substituted with methyl, ethyl, acetyl, mono- or dimethylaminosulfonyl, methoxy- or ethoxycarbonyl, aminocarbonyl, alkylaminocarbonyl, or phenylaminocarbonyl), and the remaining position is carbon optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, D, E, G, and L are nitrogen, wherein one of the nitrogen atoms is unsubstituted or substituted with methyl, ethyl, acetyl, mono- or dimethylaminosulfonyl, methoxy- or ethoxycarbonyl, aminocarbonyl, alkylaminocarbonyl, or phenylaminocarbonyl; or, D is nitrogen (wherein the nitrogen atom is unsubstituted or substituted with methyl, ethyl, acetyl, mono- or dimethylaminosulfonyl, methoxy- or ethoxycarbonyl, aminocarbonyl, alkylaminocarbonyl, or phenylaminocarbonyl), oxygen, or sulfur, L is carbon (optionally unsubstituted or substituted with methyl or ethyl) or nitrogen, and E and G together form one side of a fused phenyl or pyridyl ring (which is either unsubstituted or substituted by alkyl, alkyloxy, or alkylmercapto of 1 to 4 carbon atoms, amino, hydroxy, carboxy, or aminocarbonyl); or, D is carbon (optionally unsubstituted or substituted with methyl or ethyl) or nitrogen, E is nitrogen (wherein the nitrogen atom is unsubstituted or substituted with methyl, ethyl, acetyl, mono- or dimethylaminosulfonyl, methoxy- or ethoxycarbonyl, aminocarbonyl, alkylaminocarbonyl, or phenylaminocarbonyl), oxygen, or sulfur, G and L together form one side of a fused phenyl or pyridyl ring (which is either unsubstituted or substituted by alkyl, alkyloxy, or alkylmercapto of 1 to 4 carbon atoms, amino, hydroxy, carboxy, or aminocarbonyl); or, D, E, G, L and M form a six-membered aromatic ring of type II, wherein D, E, G, L, and M are carbon, of which one or two of these carbon atoms are optionally unsubstituted or substituted with methyl, ethyl, trifluoromethyl, hydroxymethyl, hydroxyethyl, halogen, acetyl, acetyloxy, methoxy- or ethoxycarbonyl, carboxy, hydroxy, amino, methyl- or ethylamino, acetamido, ureido, methylsulfonamido, alkyloxy of 1 to 4 carbon atoms, methyl- or ethylmercapto, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, D, E, G, L and M are carbon, wherein D and E form one side of a fused phenyl, pyridyl, pyrrolyl, thienyl, or furanyl ring (which is either unsubstituted or substituted by alkyl, alkyloxy, or alkylmercapto of 1 to 4 carbon atoms, amino, hydroxy, carboxy, or aminocarbonyl) and one of G, L, or M is optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, D, E, G, L and M are carbon, wherein E and G form one side of a fused phenyl, pyridyl, pyrrolyl, thienyl, or furanyl ring (which is either unsubstituted or substituted by alkyl, alkyloxy, or alkylmercapto of 1 to 4 carbon atoms, amino, hydroxy, carboxy, or aminocarbonyl) and one of D, L, or M is optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, D, E, G, L and M form a six-membered heteroaromatic ring of type II, wherein one of D, E, or G is nitrogen (optionally unoxidized or oxidized to the corresponding N-oxide), and the four remaining positions are carbon, of which one of these carbon atoms is optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro, and of which a second of these carbon atoms is optionally unsubstituted or substituted with methyl, ethyl, hydroxy, or amino; or, one of D, E, or G is nitrogen, L and M form one side of a fused phenyl, pyridyl, pyrrolyl, thienyl, or furanyl ring (which is either unsubstituted or substituted by alkyl, alkyloxy, or alkylmercapto of 1 to 4 carbon atoms, amino, hydroxy, carboxy, or aminocarbonyl), and the remaining two positions are carbon, of which one of these carbon atoms is optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, one of D, E or M is nitrogen, G and L form one side of a fused phenyl, pyridyl, pyrrolyl, thienyl, or furanyl ring (which is either unsubstituted or substituted by alkyl, alkyloxy, or alkylmercapto of 1 to 4 carbon atoms, amino, hydroxy, carboxy, or aminocarbonyl), and the remaining two positions are carbon, of which one of these carbon atoms is optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, D is nitrogen, E and G form one side of a fused phenyl, pyridyl, pyrrolyl, thienyl, or furanyl ring (which is either unsubstituted or substituted by alkyl, alkyloxy, or alkylmercapto of 1 to 4 carbon atoms, amino, hydroxy, carboxy, or aminocarbonyl), and the remaining two positions are carbon, of which one of these carbon atoms is optionally unsubstituted or substituted with alkyl, alkyloxy, or alkylmercapto of 1 to 4 carbon atoms, trifluoromethyl, hydroxymethyl, hydroxyethyl, halogen, acetyl, methoxy- or ethoxycarbonyl, carboxy, hydroxy, amino, methyl- or ethylamino, acetamido, ureido, methylsulfonamido, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, two of D, E, G, L, and M are nitrogen, and the three remaining positions are carbon, of which one of these carbon atoms is optionally unsubstituted or substituted with methyl, ethyl, trifluoromethyl, hydroxy, acetoxy, hydroxymethyl, hydroxyethyl, halogen, acetyl, methoxy- or ethoxycarbonyl, carboxy, hydroxy, amino, methyl- or ethylamino, acetamido, ureido, methylsulfonamido, alkyloxy of 1 to 4 carbon atoms, methyl- or ethylmercapto, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro, and of which a second of these carbon atoms is optionally unsubstituted or substituted with methyl, ethyl, hydroxy, or amino; or, two of D, E, and G are nitrogen, and L and M together form one side of a fused phenyl, pyridyl, imidazolyl, pyrazolyl, or triazolyl ring (the carbon atoms of which are either unsubstituted or substituted by alkyl, alkyloxy, or alkylmercapto of 1 to 4 carbon atoms, amino, hydroxy, carboxy, or aminocarbonyl); or, two of D, L, and M are nitrogen, and E and G together form one side of a fused phenyl, pyridyl, imidazolyl, pyrazolyl, or triazolyl ring (the carbon atoms of which are either unsubstituted or substituted by alkyl, alkyloxy, or alkylmercapto of 1 to 4 carbon atoms, amino, hydroxy, carboxy, or aminocarbonyl);

$R^1$ is hydrogen, alkyl of 1 to 6 carbon atoms, fluoroalkyl of 1 to 6 carbon atoms and 1 to 3 fluorine atoms, alkenylmethyl or alkynylmethyl of 3 to 6 carbon atoms, aryl or arylmethyl (wherein the aryl moiety is phenyl, thienyl or furanyl, which is either unsubstituted or substituted by methyl, methoxy or halogen), alkanoyl or thioalkanoyl of 2 to 4 carbon atoms, alkylsulfonyl of 1 to 4 carbon atoms, mono- or dimethylaminosulfonyl, aminosulfonyl, aminocarbonyl, mono- or di-alkylaminocarbonyl wherein each alkyl moiety contains 1 to 2 carbon atoms, aminoethyl, mono- or di-alkylaminoethyl wherein each alkyl moiety contains 1 to 2 carbon atoms, alkyloxyalkyl or alkylthioalkyl of 2 to 4 carbon atoms, alkyloxycarbonyl wherein the alkyl moiety contains 1 to 4 carbon atoms, alkenyloxycarbonyl wherein the alkenyl moiety contains 2 to 4 carbon atoms, hydroxy, alkyloxy of 1 to 4 carbon atoms, cyano, amino, mono- or di-alkylamino wherein each alkyl moiety contains 1 to 4 carbon atoms, aminocarbonylmethyl, mono- or di-alkylaminocarbonylmethyl wherein the alkyl moiety contains 1 to 2 carbon atoms;

Z is oxygen, sulfur, =NCN or a group of the formula =NOR$^8$ wherein R$^8$ is alkyl of 1 to 3 carbon atoms;

$R^2$ is hydrogen, alkyl of 1 to 6 carbon atoms, fluoroalkyl of 1 to 6 carbon atoms and 1 to 3 fluorine atoms, cycloalkyl of 3 to 6 carbon atoms, oxetanyl, thietanyl, tetrahydrofuranyl, tetrahydrothienyl, tetrahydropyranyl, tetrahydrothiopyranyl, alkenylmethyl or alkynylmethyl of 3 to 6 carbon atoms, alkyloxyalkyl or alkylthioalkyl of 2 to 5 carbon atoms, alkanoyl or thioalkanoyl of 2 to 5 carbon atoms, cyano, cyanoalkyl of 2 to 5 carbon atoms, hydroxyalkyl or acyloxyalkyl wherein the alkyl moiety contains 2 to 6 carbon atoms and the acyl moiety contains 2 to 3 carbon atoms, oxazolyl, isoxazolyl, thiazolyl, aryl or arylmethyl (wherein the aryl moiety is phenyl, thienyl or furanyl, which is either unsubstituted or substituted by alkyl or alkyloxy of 1 to 3 carbon atoms, hydroxy or halogen), or alkyloxycarbonylmethyl wherein the alkyl moiety contains 1 to 5 carbon atoms;

$R^3$ is alkyl of 1 to 6 carbon atoms, alkenyl or alkynyl of 2 to 6 carbon atoms, trihalomethyl, hydroxyalkyl of 1 to 6 carbon atoms, alkyloxyalkyl or alkylthioalkyl of 2 to 6 carbon atoms, or halogen;

$R^4$ is hydrogen, methyl, or halogen, and $R^5$ is hydrogen; or, $R^3$ and $R^5$ are each hydrogen and $R^4$ is methyl or halogen; or $R^3$ and $R^4$ are each hydrogen and $R^5$ is alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxyalkyl or alkylthioalkyl of 2 to 6 carbon atoms, aryloxy(or thio)methyl (wherein the aryl moiety is phenyl, thienyl or furanyl, which is either unsubstituted or substituted by alkyl or alkyloxy of 1 to 3 carbon atoms, hydroxy or halogen), arylmethyloxy(or thio)methyl or arylethyloxy(or thio)methyl (wherein the aryl moiety is phenyl, thienyl or furanyl, which is either unsubstituted or substituted by alkyl or alkyloxy of 1 to 3 carbon atoms, hydroxy or halogen), alkyloxycarbonylalkyl wherein the alkyl moieties each contain 1 to 2 carbon atoms, carboxyalkyl or cyanoalkyl wherein the alkyl moieties each contain 1 to 5 carbon atoms, mono- or di-alkylaminocarbonylalkyl wherein the alkyl moieties each contain 1 to 2 carbon atoms, hydroxy, mercapto, alkyloxy or alkylthio of 1 to 5 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkyloxycarbonyl wherein the alkyl moiety contains 1 to 3 carbon atoms, mono- or di-alkylaminocarbonyl wherein each alkyl moiety contains 1 to 3 carbon atoms, aminoalkyl of 1 to 4 carbon atoms, mono- or di-alkylamino wherein each alkyl moiety contains 1 to 3 carbon atoms mono- or di-alkylaminoalkyl wherein each alkyl moiety contains 1 to 3 carbon atoms, N-pyrrolidino, N-piperidino, N-morpholino, aryl or arylalkyl (wherein the aryl moiety is phenyl, pyridyl, or a 5-membered heteroaromatic ring which is either unsubstituted or substituted by alkyl or alkyloxy of 1 to 3 carbon atoms, hydroxy, amino, or halogen, and the alkyl moiety contains 1 to 3 carbon atoms which may be unsubstituted or substituted with a methyl, hydroxy, or amino groups), halogen, cyano, nitro, azido or carboxy; or, $R^5$ is hydrogen and $R^3$ and $R^4$ are joined to form a cycloalkyl with a 3 or 4 carbon bridge; or, $R^3$ is hydrogen and $R^4$ and $R^5$ are joined to form a cycloalkyl with a 3 or 4 carbon bridge; or, $R^3$, $R^4$, and $R^5$ are each hydrogen;

$R^6$ and $R^7$ are each hydrogen;

or a pharmaceutically acceptable salt thereof.

2. A compound of formula 1, as set forth in claim 1, wherein,

A is a connecting chain of 1 to 3 atoms, wherein one of the atoms is oxygen, nitrogen (unsubstituted or substituted with methyl or acetyl), or sulfur (optionally oxidized or unoxidized), and the remaining atoms are carbon; or, all of the atoms are carbon atoms, wherein two of the atoms form a cis-alkenyl bond or all of the atoms are connected by single bonds and one of the atoms is optionally unsubstituted or substituted with oxo, methyl, hydroxy, halogen, or amino; or, A is an amide, wherein the nitrogen atom (unsubstituted or substituted with methyl) is attached to the tricyclic skeleton and the carbonyl is attached to the 5- or 6-membered aromatic ring; or, A is a cis-1,2-disubstituted cyclopropyl or oxiranyl ring;

D, E, G, and L form a five-membered heteroaromatic ring of type I, wherein the dotted bonds represent either double or single bonds depending on the valency of the atoms, either D or E is nitrogen (unsubstituted or substituted with methyl, ethyl, or acetyl), and the three remaining positions are carbon, wherein one or two of these carbon atoms are optionally unsubstituted or substituted with alkyl, alkyloxy, or alkylmercapto of 1 to 3 carbon atoms, amino, hydroxy, carboxy, or aminocarbonyl; or, one of D, E, G, and L is nitrogen, one is oxygen or sulfur, and the two remaining positions are carbon, wherein one of the carbon atoms is optionally unsubstituted or substituted with alkyl, alkyloxy, or alkylmercapto of 1 to 3 carbon atoms, amino, hydroxy, carboxy, or aminocarbonyl; or, two of D, E, G, and L are nitrogen (wherein one of the nitrogen atoms is unsubstituted or substituted with methyl, ethyl, or acetyl), and the two remaining positions are carbon, wherein one of the carbon atoms is optionally unsubstituted or substituted with alkyl, alkyloxy, or alkylmercapto of 1 to 3 carbon atoms, amino, hydroxy, carboxy, or aminocarbonyl; or, two of D, E, G, and L are nitrogen, one is oxygen or sulfur, and the remaining position is carbon, optionally unsubstituted or substituted with alkyl, alkyloxy, or alkylmercapto of 1 to 3 carbon atoms, amino, hydroxy, carboxy, or aminocarbonyl; or, three of D, E, G, and L are nitrogen (wherein one of the nitrogen atoms is unsubstituted or substituted with methyl, ethyl, or acetyl), and the remaining position is carbon, optionally unsubstituted or substituted with alkyl, alkyloxy, or alkylmercapto of 1 to 3 carbon atoms, amino, hydroxy, carboxy, or aminocarbonyl; or, D, E, G, and L are nitrogen, wherein one of the nitrogen atoms is unsubstituted or substituted with methyl, ethyl, acetyl; or, D is nitrogen (wherein the nitrogen atom is unsubstituted or substituted with methyl, ethyl, or acetyl), oxygen, or sulfur, L is carbon or nitrogen, and E and G together form one side of a fused phenyl or pyridyl ring (which is optionally unsubstituted or substituted with alkyl, alkyloxy, or alkylmercapto of 1 to 3 carbon atoms, amino, hydroxy, carboxy, or aminocarbonyl; or, D is carbon or nitrogen, E is nitrogen (wherein the nitrogen atom is unsubstituted or substituted with methyl, ethyl, or acetyl), oxygen, or sulfur, G and L together form one side of a fused phenyl or pyridyl ring (which is optionally unsubstituted or substituted with alkyl, alkyloxy, or alkylmercapto of 1 to 3 carbon atoms, amino, hydroxy, carboxy, or aminocarbonyl; or, D, E, G, L and M form a six-membered aromatic ring of type II, wherein D, E, G, L, and M are carbon, of which one of these carbon atoms is optionally unsubstituted or substituted with methyl, ethyl, amino, methyl- or ethylamino, acetamido, acetyl, acetyloxy, hydroxy, halogen, trifluoromethyl, hydroxymethyl, methoxy, ethoxy, methyl- or ethylmercapto, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, or cyano, and of which a second of these carbon atoms is optionally unsubstituted or substituted with methyl or ethyl; or, D, E, G, L and M are carbon, wherein D and E form one side of a fused phenyl, pyridyl, pyrrolyl, thienyl, or furanyl ring (which is either unsubstituted or substituted by alkyl, alkyloxy, or alkylmercapto of 1 to 3 carbon atoms, amino, hydroxy, carboxy, or aminocarbonyl) and one of G, L, or M is optionally unsubstituted or substituted with alkyl, alkyloxy, or alkylmercapto of 1 to 3 carbon atoms, amino, methyl- or ethylamino, hydroxy, halogen, trifluoromethyl, hydroxymethyl, methoxy- or ethoxycarbonyl, or aminocarbonyl; or, D, E, G, L and M are carbon, wherein E and G form one side of a fused phenyl, pyridyl, pyrrolyl, thienyl, or furanyl ring (which is either unsubstituted or substituted by alkyl, alkyloxy, or alkylmercapto of 1 to 3 carbon atoms, amino, hydroxy, carboxy, or aminocarbonyl) and one of D, L, or M is optionally unsubstituted or substituted with alkyl, alkyloxy, or alkylmercapto of 1 to 3 carbon atoms, amino, methyl- or ethylamino, hydroxy, halogen, trifluoromethyl, hydroxymethyl, methoxy- or ethoxycarbonyl, or aminocarbonyl; or, D, E, G, L and M form a six-membered heteroaromatic ring of type II, wherein one of D, E, or G is nitrogen (optionally unoxidized or oxidized to the corresponding N-oxide), and the four remaining positions are carbon, of which one of these carbon atoms is optionally unsubstituted or substituted with methyl, ethyl, amino, methyl- or ethylamino, acetamido, acetyl, acetyloxy, hydroxy, halogen, trifluoromethyl, hydroxymethyl, methoxy, ethoxy, methyl- or ethylthio, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, or cyano, and of which a second of these carbon atoms is optionally unsubstituted or substituted with methyl or ethyl; or, one of D, E, or G is nitrogen, L and M form one side of a fused phenyl, pyridyl, pyrrolyl, thienyl, or furanyl ring (which is either unsubstituted or substituted by alkyl, alkyloxy, or alkylmercapto of 1 to 3 carbon atoms, amino, hydroxy, carboxy, or aminocarbonyl), and the remaining two positions are carbon, of which one of these carbon atoms is optionally unsubstituted or substituted with alkyl, alkyloxy, or alkylmercapto of 1 to 3 carbon atoms, amino, methyl- or ethylamino, hydroxy, halogen, trifluoromethyl, hydroxymethyl, methoxy- or ethoxycarbonyl, or aminocarbonyl; or, one of D, E or M is nitrogen, G and L form one side of a fused phenyl, pyridyl, pyrrolyl, thienyl, or furanyl ring (which is either unsubstituted or substituted by alkyl, alkyloxy, or alkylmercapto of 1 to 3 carbon atoms, amino, hydroxy, carboxy, or aminocarbonyl), and the remaining two positions are carbon, of which one of these carbon atoms is optionally unsubstituted or substituted with alkyl, alkyloxy, or alkylmercapto of 1 to 3 carbon atoms, amino, methyl- or ethylamino, hydroxy, halogen, trifluoromethyl, hydroxymethyl, methoxy- or ethoxycarbonyl, or aminocarbonyl; or, D is nitrogen, E and G form one side of a fused phenyl, pyridyl, pyrrolyl, thienyl, or furanyl ring (which is either unsubstituted or substituted by alkyl, alkyloxy, or alkylmercapto of 1 to 3 carbon atoms, amino, hydroxy, carboxy, or aminocarbonyl), and the remaining two positions are carbon, of which one of these carbon atoms is optionally unsubstituted or substituted with alkyl, alkyloxy, or alkylmercapto of 1 to 3 carbon atoms, amino, methyl- or ethylamino, hydroxy, halogen, trifluoromethyl, hydroxymethyl, methoxy- or ethoxycarbonyl, or aminocarbonyl; or, two of D, E, G, L, and M are nitrogen, and the three remaining positions are carbon, of which one of these carbon atoms is optionally unsubstituted or substituted with methyl, ethyl, amino, methyl- or ethylamino, acetamido, acetyl, acetyloxy, hydroxy, halogen, trifluoromethyl, hydroxymethyl, methoxy, ethoxy, methyl- or ethylthio, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, or cyano, and of which a second of these carbon atoms is optionally unsubstituted or substituted with methyl or ethyl; or, two of D, E, and G are nitrogen, and L and M together form one side of a fused phenyl, pyridyl, imidazolyl, pyrazolyl, or triazolyl ring (the carbon atoms of which are either unsubstituted or substituted by alkyl, alkyloxy, or alkylmercapto of 1 to 3 carbon atoms, amino, hydroxy, carboxy, or aminocarbonyl); or, two of D, L, and M are nitrogen, and E and G together form one side of a fused phenyl, pyridyl, imidazolyl, pyrazolyl, or triazolyl ring (the carbon atoms of which are either unsubstituted or substituted by alkyl, alkyloxy, or alkylmercapto of 1 to 3 carbon atoms, amino, hydroxy, carboxy, or aminocarbonyl);

$R^1$ is hydrogen, alkyl of 1 to 4 carbon atoms, fluoroalkyl of 1 to 4 carbon atoms and 1 to 3 fluorine atoms, cyclopropyl, alkenylmethyl or alkynylmethyl of 3 to 4 carbon atoms, 2-halo-2-propen-1-yl, alkanoyl of 2 to 3 carbon atoms, alkyloxyalkyl or alkylthioalkyl of 2 to 3 carbon atoms, or cyanoalkyl wherein the alkyl moiety contains 1 to 3 carbon atoms;

Z is oxygen, sulfur or a group of the formula $=NOR^9$ wherein $R^9$ is methyl or ethyl;

$R^2$ is hydrogen, alkyl of 1 to 5 carbon atoms, fluoroalkyl of 1 to 5 carbon atoms, cycloalkyl of 3 to 5 carbon atoms, oxetanyl, thietanyl, alkenylmethyl or alkynylmethyl of 3 to 5 carbon atoms, alkyloxyalkyl or alkylthioalkyl of 2 to 4 carbon atoms, alkanoyl of 2 to 4 carbon atoms, hydroxyalkyl of 2 to 5 carbon atoms, aryl or arylmethyl (wherein the aryl moiety is phenyl, thienyl or furanyl, which is either unsubstituted or substituted by alkyl or alkyloxy of 1 to 3 carbon atoms, hydroxy or halogen), or alkyloxycarbonylmethyl wherein the alkyl moiety contains 1 to 4 carbon atoms;

$R^3$ is alkyl of 1 to 6 carbon atoms, alkenyl or alkynyl of 2 to 6 carbon atoms, trihalomethyl, hydroxyalkyl of 1 to 6 carbon atoms, alkyloxyalkyl or alkylthioalkyl of 2 to 6 carbon atoms, or halogen;

$R^4$ is hydrogen, methyl, or halogen, and $R^5$ is hydrogen; or, $R^3$ and $R^5$ are each hydrogen and $R^4$ is methyl or halogen; or $R^3$ and $R^4$ are each hydrogen and $R^5$ is alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxyalkyl or alkylthioalkyl of 2 to 6 carbon atoms, aryloxy(or thio)methyl (wherein the aryl moiety is phenyl, thienyl or furanyl, which is either unsubstituted or substituted by alkyl or alkyloxy of 1 to 3 carbon atoms, hydroxy or halogen), arylmethyloxy(or thio) methyl or arylethyloxy(or thio)methyl (wherein the aryl moiety is phenyl, thienyl or furanyl, which is either unsubstituted or substituted by alkyl or alkyloxy of 1 to 3 carbon atoms, hydroxy or halogen), alkyloxycarbonylalkyl wherein the alkyl moieties each contain 1 to 2 carbon atoms, carboxyalkyl or cyanoalkyl wherein the alkyl moieties each contain 1 to 5 carbon atoms, mono- or di-alkylaminocarbonylalkyl wherein the alkyl moieties each contain 1 to 2 carbon atoms, hydroxy, mercapto, alkyloxy or alkylthio of 1 to 5 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkyloxycarbonyl wherein the alkyl moiety contains 1 to 3 carbon atoms, mono- or di-alkylaminocarbonyl wherein each alkyl moiety contains 1 to 3 carbon atoms, aminoalkyl of 1 to 4 carbon atoms, mono- or di-alkylamino wherein each alkyl moiety contains 1 to 3 carbon atoms mono- or di-alkylaminoalkyl wherein each alkyl moiety contains 1 to 3 carbon atoms, N-pyrrolidino, N-piperidino, N-morpholino, aryl or arylalkyl (wherein the aryl moiety is phenyl, pyridyl, or a 5-membered heteroaromatic ring which is either unsubstituted or substituted by alkyl or alkyloxy of 1 to 3 carbon atoms, hydroxy, amino, or halogen, and the alkyl moiety contains 1 to 3 carbon atoms which may be unsubstituted or substituted with a methyl, hydroxy, or amino groups), halogen, cyano, nitro, azido or carboxy; or, $R^5$ is hydrogen and $R^3$ and $R^4$ are joined to form a cycloalkyl with a 3 or 4 carbon bridge; or, $R^3$ is hydrogen and $R^4$ and $R^5$ are joined to form a cycloalkyl with a 3 or 4 carbon bridge; or, $R^3$, $R^4$, and $R^5$ are each hydrogen;

$R^6$ and $R^7$ are each hydrogen;

or a pharmaceutically acceptable salt thereof.

3. A compound of formula 1, as set forth in claim 1, wherein,

A is a connecting chain of 1 to 3 atoms, wherein one of the atoms is oxygen, nitrogen as —NH— or —NCH$_3$—, or sulfur as —S—, —SO—, or —SO$_2$—, and the remaining atoms are carbon as —CH$_2$—, with the proviso that any of the oxygen, nitrogen or sulfur atoms are not attached directly to the tricyclic nucleus; or A is —CH=CH— wherein the alkene is of cis stereochemistry; or —CH$_2$—, —CH$_2$CH$_2$—, —CH$_2$CH$_2$CH$_2$—, wherein one of the carbon atoms is optionally substituted by oxo, hydroxy, halogen or amino; or A is a 1,2-cis-disubstituted cyclopropyl or oxiranyl ring;

D, E, G, L and M form a six-membered aromatic ring of type II, wherein D, E, G, L, and M are carbon, of which one of these carbon atoms is optionally unsubstituted or substituted with methyl, ethyl, amino, methyl- or ethylamino, acetamido, acetamidomethyl, acetyl, acetyloxy, hydroxy, halogen, trifluoromethyl, hydroxymethyl, methoxy, ethoxy, methyl- or ethylthio, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, or cyano, and of which a second of these carbon atoms is optionally unsubstituted or substituted with methyl or ethyl; or, D, E, G, L and M form a six-membered heteroaromatic ring of type II, wherein one of D, E, or G is nitrogen (optionally unoxidized or oxidized to the corresponding N-oxide), and the four remaining positions are carbon, of which one of these carbon atoms is optionally unsubstituted or substituted with methyl or amino; and, $R^1$ is hydrogen, alkyl of 1 to 3 carbon atoms or allyl;

Z is oxygen;

$R^2$ is alkyl of 2 to 3 carbon atoms, or cycloalkyl of 3 to 4 carbon atoms;

$R^4$ is hydrogen, methyl, or chloro;

$R^3$ is hydrogen, methyl, trifluoromethyl, or chloro, with the proviso that $R^3$ is not trifluoromethyl or chloro when $R^4$ is chloro;

$R^5$ is hydrogen, fluoro, or chloro;

$R^6$ and $R^7$ are hydrogen;

a pharmaceutically acceptable salt thereof.

4. A compound selected from the group consisting of:
(a) 2-Chloro-5,11-dihydro-11-ethyl-5-methyl-8-[2-(pyrid-4-yl)ethyl]-6H-dipyrido[3,2-b:2',3'-e][1,4]diazepin-6-one;
(b) 5,11-Dihydro-11-ethyl-2-fluoro-5-methyl-8-[2-(pyrid-4-yl)ethyl]-6H-dipyrido[3,2-b:2',3'-e][1,4]diazepin-6-one;
(c) 2-Chloro-5,11-dihydro-11-ethyl-8-[2-hydroxy-2-(pyrid-4-yl)ethyl]-5-methyl-6H-dipyrido[3,2-b:2',3'-e][1,4]diazepin-6-one;
(d) 2-Chloro-5,11-dihydro-11-ethyl-8-[2-hydroxy-2-(N-oxo-pyrid-4-yl)ethyl]-5-methyl-6H-dipyrido[3,2-b:2'3'-e][1,4]diazepin-6-one;
(e) 5,11-Dihydro-11-ethyl-2-fluoro-8-[2-(N-oxo-pyrid-4-yl)ethyl]-5-methyl-6H-dipyrido[3,2-b:2',3'-e][1,4]diazepin-6-one; and
(f) 5,11-Dihydro-11-ethyl-2-fluoro-8-[2-hydroxy-2-(pyrid-4-yl)ethyl]-5-methyl-6H-dipyrido[3,2-b:2',3'-e][1,4] diazepin-6-one;

or a pharmaceutically acceptable salt thereof.

5. A compound selected from the group consisting of:
(a) 5,11-dihydro-11-ethyl-2-fluoro-5-methyl-8-((N-oxo-pyrid-4-yl)oxy)methyl-6H-dipyrido[3,2-b:2',3'-e][1,4] diazepin-6-one;
(b) 2-chloro-5,11-dihydro-11-ethyl-5-methyl-8-[2-(N-oxo-pyrid-4-yloxy)ethyl]-6H-dipyrido[3,2-b:2',3'-e][1,4] diazepin-6-one;
(c) 8-(3-aminophenyloxy)methyl-2-chloro-5,11-dihydro-11-ethyl-5-methyl-6H-dipyrido[3,2-b:2',3'-e][1,4]diazepin-6-one;
(d) 2-chloro-5,11-dihydro-11-ethyl-5-methyl-8-(phenylthio)methyl-6H-dipyrido[3,2-b:2',3'-e][1,4]diazepin-6-one;
(e) 2-chloro-5,11-dihydro-11-ethyl-5-methyl-8-(pyrid-4-ylthio)methyl-6H-dipyrido[3,2-b:2',3'-e][1,4]diazepin-6-one;

(f) 2-chloro-5,11-dihydro-11-ethyl-5-methyl-8-(pyrid-4-yloxy)methyl-6H-dipyrido[3,2-b:2',3'-e][1,4]diazepin-6-one;

(g) 5,11-dihydro-11-ethyl-2-fluoro-5-methyl-8-(pyrid-4-yloxy)methyl-6H-dipyrido[3,2-b:2',3'-e][1,4]diazepin-6-one;

i (h) 2-chloro-5,11-dihydro-11-ethyl-5-methyl-8-[2-(pyrid-4-yloxy)ethyl]-6H-dipyrido[3,2-b:2',3'-e][1,4]diazepin-6-one;

(i) 2-chloro-5,11-dihydro-11-ethyl-5-methyl-8-((N-oxo-pyrid-4-yl)methoxy)methyl-6H-dipyrido[3,2-b:2',3'-e][1,4]diazepin-6-one;

(j) 2-chloro-5,11-dihydro-11-ethyl-5-methyl-8-(pyrid-4-ylmethoxy)methyl-6H-dipyrido[3,2-b:2',3'-e][1,4]diazepin-6-one;

(k) 5,11-dihydro-11-ethyl-2-fluoro-5-methyl-8-[2-(N-oxopyrid-4-yloxy)ethyl]-6H-dipyrido[3,2-b:2',3'-e][1,4]diazepin-6-one;

(l) 8-(3-aminophenyloxy)methyl-5,11-dihydro-11-ethyl-2-fluoro-5-methyl-6H-dipyrido[3,2-b:2',3'-e][1,4]diazepin-6-one;

(m) 5,11-dihydro-11-ethyl-2-fluoro-5-methyl-8-(phenylthio)methyl-6H-dipyrido[3,2-b:2',3'-e][1,4]diazepin-6-one;

(n) 5,11-dihydro-11-ethyl-2-fluoro-5-methyl-8-(pyrid-4-ylthio)methyl-6H-dipyrido[3,2-b:2',3'-e][1,4]diazepin-6-one;

(o) 5,11-dihydro-11-ethyl-2-fluoro-5-methyl-8-[2-(pyrid-4-yloxy)ethyl]-6H-dipyrido[3,2-b:2',3'-e][1,4]diazepin-6-one;

(p) 5,11-dihydro-11-ethyl-2-fluoro-5-methyl-8-((N-oxopyrid-4-yl)methoxy)methyl-6H-dipyrido[3,2-b:2',3'-e][1,4]diazepin-6-one; and (q) 5,11-dihydro-11-ethyl-2-fluoro-5-methyl-8-(pyrid-4-ylmethoxy)methyl-6H-dipyrido[3,2-b:2',3'-e][1,4]diazepin-6-one;

or a pharmaceutically acceptable salt thereof.

6. 2-chloro-5,11-dihydro-11-ethyl-5-methyl8-[2-(N-oxopyrid-4-yloxy)ethyl]-6H-dipyrido[3,2-b:2',3'-e][1,4]diazepin-6-one; or a pharmaceutically acceptable salt thereof.

7. 2-chloro-5,11-dihydro-11-ethyl-5-methyl-8-(phenylthio)methyl-6H-dipyrido[3,2-b:2',3'-e][1,4]diazepin-6-one.

8. 2-chloro-5,11-dihydro-11-ethyl-5-methyl-8-[2-(pyrid-4-yloxy)ethyl]-6H-dipyrido[3,2-b:2',3'-e][1,4]diazepin-6-one.

9. A method for treating HIV-1 infection which comprises administering, to a human being infected by HIV-1, a therapeutically effective amount of a compound of formula 1, as set forth in claims 1, 2 or 3.

10. A pharmaceutical composition suitable for treating HIV-1 infection which comprises a therapeutically effective amount of a compound of formula 1, as set forth in claims 1, 2 or 3 and a pharmaceutically acceptable carrier.

* * * * *